US012667638B2

(12) United States Patent
Harrell et al.

(10) Patent No.: US 12,667,638 B2
(45) Date of Patent: Jun. 30, 2026

(54) PLUG-IN FRAGRANCE DIFFUSER, AND SYSTEMS AND METHODS FOR USING SAME

(71) Applicant: beautyAvenues, LLC, Reynoldsburg, OH (US)

(72) Inventors: Jason Harrell, Acworth, GA (US); Trent Hoverman, Westerville, OH (US); Patrick Guerin, Fairfield, IA (US); Richard Wisniewski, Blacklick, OH (US)

(73) Assignee: beautyAvenues, LLC, Reynoldsburg, OH (US)

( * ) Notice: Subject to any disclaimer, the term of this patent is extended or adjusted under 35 U.S.C. 154(b) by 1066 days.

(21) Appl. No.: 16/929,551

(22) Filed: Jul. 15, 2020

(65) Prior Publication Data

US 2021/0015955 A1    Jan. 21, 2021

Related U.S. Application Data

(60) Provisional application No. 63/013,816, filed on Apr. 22, 2020, provisional application No. 62/916,846, (Continued)

(51) Int. Cl.
*A61L 9/03*        (2006.01)
*A01M 1/20*        (2006.01)

(52) U.S. Cl.
CPC ............. *A61L 9/03* (2013.01); *A01M 1/2077* (2013.01); *A61L 2209/111* (2013.01); *A61L 2209/133* (2013.01)

(58) Field of Classification Search
CPC ................. A61L 9/03; A61L 2209/111; A61L 2209/133; A61L 2209/11; A61L 2209/12;
(Continued)

(56) References Cited

U.S. PATENT DOCUMENTS 6,792,199 B2    9/2004  Levine et al.
6,950,607 B2    9/2005  Chun
(Continued)

FOREIGN PATENT DOCUMENTS

CA        3087002        4/2018
CN        101954110        1/2011
(Continued)

OTHER PUBLICATIONS

U.S. Appl. No. 62/876,347, filed Jul. 19, 2019, Harrell (beautyAvenues LLC).

(Continued)

*Primary Examiner* — Qingzhang Zhou
(74) *Attorney, Agent, or Firm* — Andrus Intellectual Property Law, LLP

(57) ABSTRACT

A fragrance dispenser can comprise a housing having a socket portion and defining a receptacle configured to receive a bottle having a fragrance-producing liquid therein and a wick extending therefrom. A heater can be disposed proximate to the receptacle so that, when the bottle is received within the receptacle, the heater is disposed proximate to the wick. A controller can be configured to deliver electrical voltage (e.g., pulse-width-modulated voltage) to the heater. A user input device can be in communication with the controller.

7 Claims, 29 Drawing Sheets

Related U.S. Application Data filed on Oct. 18, 2019, provisional application No. 62/876,347, filed on Jul. 19, 2019.

(58) Field of Classification Search
CPC ................. A61L 9/037; A61L 2209/13; A61L 2209/134; A01M 1/2077; F21V 33/00; G03B 29/00; F21Y 2115/10
See application file for complete search history.

(56) References Cited

U.S. PATENT DOCUMENTS

| | | | |
|---|---|---|---|
| 7,223,361 B2 | 5/2007 | Kvietok | |
| 7,932,482 B2 | 4/2011 | Norwood et al. | |
| 7,981,367 B2 | 7/2011 | Kvietok et al. | |
| 8,016,207 B2 | 9/2011 | Kvietok et al. | |
| 8,061,628 B1 | 11/2011 | Kvietok et al. | |
| 8,074,970 B2 | 12/2011 | Pankhurst et al. | |
| 8,119,064 B2 | 2/2012 | Woo et al. | |
| 8,197,762 B2 | 6/2012 | Gasper | |
| 8,210,448 B2 | 7/2012 | Kvietok et al. | |
| 8,349,251 B2 | 1/2013 | Woo et al. | |
| 8,464,905 B2 | 6/2013 | Hoppe | |
| 8,651,395 B2 | 2/2014 | Kvietok et al. | |
| 8,750,693 B2 | 6/2014 | Sharma | |
| 8,807,390 B2 | 8/2014 | Saleh et al. | |
| 8,855,827 B2 | 10/2014 | Weening | |
| 8,891,947 B2 | 11/2014 | Neumann et al. | |
| 8,983,279 B2 | 3/2015 | Adair et al. | |
| 9,278,150 B2 | 3/2016 | Gruenbacher et al. | |
| 9,439,995 B2 | 9/2016 | Conroy et al. | |
| 9,460,404 B2 | 10/2016 | Chandler | |
| 9,486,552 B1 | 11/2016 | Ansley | |
| 9,669,125 B2 * | 6/2017 | Gasper | A61L 9/035 |
| 9,789,219 B2 | 10/2017 | Kelly | |
| 9,808,812 B2 | 11/2017 | Gruenbacher et al. | |
| 9,827,343 B2 | 11/2017 | Lima et al. | |
| 9,884,133 B2 | 2/2018 | Tebé Poves et al. | |
| 10,010,898 B2 | 7/2018 | Gasper | |
| 10,076,585 B2 | 9/2018 | Gruenbacher et al. | |
| 10,086,340 B2 | 10/2018 | Ansley | |
| 10,416,687 B2 | 9/2019 | Hasenoehrl | |
| 10,429,806 B2 | 10/2019 | Hasenoehrl | |
| 10,512,706 B2 | 12/2019 | Avidor | |
| 10,764,963 B2 | 9/2020 | Davis et al. | |
| 10,814,028 B2 | 10/2020 | Becker et al. | |
| 11,033,651 B2 | 6/2021 | Weening | |
| 11,865,233 B2 | 1/2024 | Sward | |
| 11,896,743 B2 | 2/2024 | Turner | |
| 2004/0067172 A1 | 4/2004 | Ehrlich | |
| 2005/0185392 A1 | 8/2005 | Walter et al. | |
| 2008/0056691 A1 | 3/2008 | Wingo | |
| 2008/0251598 A1 | 10/2008 | Ross | |
| 2010/0294852 A1 | 11/2010 | Banco | |
| 2011/0284653 A1 | 11/2011 | Butler | |
| 2012/0024974 A1 | 2/2012 | Grodsky | |
| 2013/0081541 A1 | 4/2013 | Hasenoehrl | |
| 2014/0034748 A1 * | 2/2014 | Adair | A61L 9/037 239/6 |
| 2014/0374402 A1 | 12/2014 | Cornelius | |
| 2016/0366874 A1 | 12/2016 | Caride | |
| 2017/0102156 A1 | 4/2017 | Hasenoehrl | |
| 2017/0173203 A1 | 6/2017 | Becker | |
| 2017/0274405 A1 * | 9/2017 | Lucas | B05B 17/0661 |
| 2017/0281819 A1 | 10/2017 | Jones et al. | |
| 2018/0078954 A1 | 3/2018 | Gruenbacher et al. | |
| 2019/0184050 A1 | 6/2019 | Hernandez | |
| 2019/0192717 A1 | 6/2019 | Harwig et al. | |
| 2019/0216967 A1 | 7/2019 | Turner et al. | |
| 2021/0015955 A1 | 1/2021 | Harrell et al. | |
| 2021/0213471 A1 | 7/2021 | Richard | |
| 2023/0331070 A1 | 10/2023 | Probst | |
| 2024/0042085 A1 | 2/2024 | Hasik | |
| 2024/0082448 A1 | 3/2024 | Beckstead | |
| 2024/0255338 A1 | 8/2024 | Davis | |
| 2024/0277882 A1 | 8/2024 | Altuna | |

FOREIGN PATENT DOCUMENTS

| | | | | |
|---|---|---|---|---|
| CN | 106456820 | 2/2017 | | |
| CN | 2020106945630 | 4/2018 | | |
| CN | 207400267 | 5/2018 | | |
| CN | 108472399 | 8/2018 | | |
| CN | 109789232 | 5/2019 | | |
| EP | 2384771 | * | 11/2011 | |
| EP | 2384771 A1 | | 11/2011 | |
| EP | 20186408.9 | | 4/2018 | |
| WO | WO-2004071935 A2 | * | 8/2004 | A01M 1/2061 |
| WO | WO 2006/105396 A1 | | 10/2006 | |
| WO | WO2006105396 | * | 10/2006 | |
| WO | 2008119068 A1 | | 10/2008 | |
| WO | 2009085170 A1 | | 7/2009 | |
| WO | WO 2014/087173 A1 | | 6/2014 | |
| WO | WO2014087173 | * | 6/2014 | |
| WO | WO2018/026932 | * | 2/2018 | |
| WO | WO 2018/026932 A1 | | 2/2018 | |
| WO | 2023159217 A1 | | 8/2023 | |

OTHER PUBLICATIONS

U.S. Appl. No. 62/916,846, filed Oct. 18, 2019, Harrell (beautyAvenues LLC).
U.S. Appl. No. 63/013,816, filed Apr. 22, 2020, Harrell (beautyAvenues LLC).
EPO Search Report for App. No. 20186408.9 dated Dec. 14, 2020.
Screenshot of "Wax Melt Warmer Electric Tart Warmer Plug in Pluggable Home Fragrance Diffuser" from https://www.amazon.com/Electric-Pluggable-Fragrance-Diffuser-Lantern/dp/B01ISMF00Y, visited Oct. 7, 2019.
Air Wick plug in Scented Oil. https://www.amazon.com/Air-Wick-Scented-Oil-Chamomile/dp/B01EHEIVI2. Captured Apr. 2, 2021.
Ambi Pur Air Freshener with Electric Diffuser. https://www.amazon.com/Ambipur-electric-freshener-tatami-21-5ml/dp/B00XI10ME2. Captured Apr. 2, 2021.
Glade Plug Ins Air Freshener Warmer. https://www.amazon.com/Glade-PlugIns-Scented-Freshener-Electric/dp/B011JA1NXM. Captured Apr. 2, 2021.
Febreze Plug Starter Kit. Https://www.amazon.com/Febreze-Plug-Starter-Kit/dp/B07H3JWQR3/?ref=asc_df_B07H3JWQR3/?tag=hyprod-20&linkCode=df0&hvadid=309782350753&hvpos=&hvnetw=g&hvrand=14623499202681711387&hvpone=&hvptwo=&hvqmt=&hvdev=c&hvdvcmdl=&hvlocint=&hvlocphy=9012104&hvtargid=pla-583313988166&psc=1&tag=&ref=&adgrpid=63334408722&hvpone=&hvptwo=&hvadid=309782350753&hvpos=&hvnetw=g&hvrand=14623499202681711387&hvqmt=&hvdev=c&hvdvcmdl=&hvlocint=&hvlocphy=9012104&hvtargid=pla-583313988166. Captured Apr. 2, 2021.
Second Office Action in Chinese Application No. 202010694563.0, dated Feb. 25, 2025, 7 pages.

\* cited by examiner

400

900

902

906

Bulb Level

LOW

Order new scent?

904

Current Offers:
3 for $24 refills

Diffusion Film

Acrylic plate - Front Side

Acrylic plate - Back Side w/ white dot printing

Reflecting Film

LED PCBA

600

600

PLUG-IN FRAGRANCE DIFFUSER, AND SYSTEMS AND METHODS FOR USING SAME

CROSS-REFERENCE TO RELATED APPLICATIONS

This application claims priority to and the benefit of U.S. Provisional Application No. 63/013,816, filed Apr. 22, 2020, U.S. Provisional Application No. 62/916,846, filed Oct. 18, 2019, and U.S. Provisional Application No. 62/876,347, filed Jul. 19, 2019, the entirety of each of which is incorporated herein by reference in its entirety.

FIELD

This invention relates to plug-in vapor emanation devices and systems and, more particularly, to devices and systems for diffusing one or more fragrances.

BACKGROUND

Plug-in wick-based vapor emanation systems are known in the art for dispersing into the air vapors of a variety of liquids. Such systems are often used in the home with liquids varying from insect repellent to air freshener. Typically, in such systems, one end of a wick is partially submerged in the liquid to be dispersed. The liquid is contained in a suitable container. The partially submerged portion of the wick absorbs the liquid, some of which diffuses by capillary or wicking action into the exposed, unsubmerged portion of the wick. The exposed portion of the wick is locally heated, often by means of a heating device that fits over the wick. This causes the liquid which has diffused into the exposed portion of the wick to evaporate into the surrounding air. Continual application of heat to the exposed portion of the wick results in an evaporation/absorption process that continues until the liquid is consumed.

One limitation of conventional wick-based vapor emanation systems is that the perceived smell of fragrance provided by conventional wick-based vapor emanation systems is non-uniform. One cause includes the fact that human sensory feedback suffers from olfactory fatigue. Additionally, conventional wick-based vapor emanation systems, when maintaining a constant wattage of the heating device, have non-linear dissipation rates, and the dissipation can vary based on the type of fragrance. Moreover, some fragrances change sensory characteristics when vaporized at different voltage levels.

Another limitation of conventional wick-based vapor emanation systems is that the dissipation rate cannot be controlled, leading to overwhelming fragrance levels for small spaces and weak fragrance levels for large, open spaces.

Accordingly, current plug-in wick-based vapor emanation systems lack various features that can be desirable.

SUMMARY

Described herein, in various aspects, is a fragrance dispenser comprising a housing having a socket portion and defining a receptacle configured to receive a bottle having a fragrance-producing liquid therein and a wick extending therefrom. A heater can be disposed proximate to the receptacle so that, when the bottle is received within the receptacle, the heater is disposed proximate to the wick. A controller can be in electrical communication with the heater. The controller can be configured to deliver pulse-width-modulated electrical voltage to the heater. The pulse-width-modulated electrical voltage can have a duty cycle. A user input device can be in communication with the controller. The user input device, upon receiving an input from a user, can cause the controller to change the duty cycle of the pulse-width-modulated electrical voltage. A plurality of lights can be in communication with the controller. The controller can be configured to illuminate one or more lights of the plurality of lights based on the duty cycle of the pulse-width-modulated electrical voltage. In further aspects, the controller can be configured to vary the intensity of one or more of the plurality of lights based on the duty cycle of the pulse-width-modulated electrical voltage.

A system can comprise a fragrance dispenser, a camera, and processor in communication with the camera and the controller, wherein the processor is configured to receive from the camera an image of an identifier that is associated with the bottle, and wherein the identifier is indicative of the type of fragrance-producing liquid in the bottle.

A system can comprise at least one diffuser and a remote computing device in communication with the at least one diffuser, wherein the remote device is configured to provide a user interface to a user, receive input from the user via the user interface, and in response to receiving the input from the user, perform an operation selected from the group of: adjusting a fragrance diffusion rate of the at least one diffuser, turning on the at least one diffuser, turning off the at least one diffuser.

Optionally, the dispenser can include an illuminating panel, a projector, and/or an illuminated cuff as further disclosed herein.

A fragrance dispenser can comprise a housing having a socket portion and defining a receptacle configured to receive a bottle having a fragrance-producing liquid therein and a wick extending therefrom. A heater can be disposed proximate to the receptacle so that, when the bottle is received within the receptacle, the heater is disposed proximate to the wick. The heater can have a variable power output. A controller can be in electrical communication with the heater. The controller can be configured to control the power output of the heater in accordance with a heat profile. The heat profile can comprise a first power output, a second power output that is greater than the first power output, and a third power output that is greater than the first and second power outputs. Each of the first, second, and third power outputs can have a duration ranging from 73 minutes to one week.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE DRAWINGS

These and other features of the preferred embodiments of the invention will become more apparent in the detailed description in which reference is made to the appended drawings wherein:

FIG. 19 further shows a projection from the projector.

DETAILED DESCRIPTION

Figure 1:
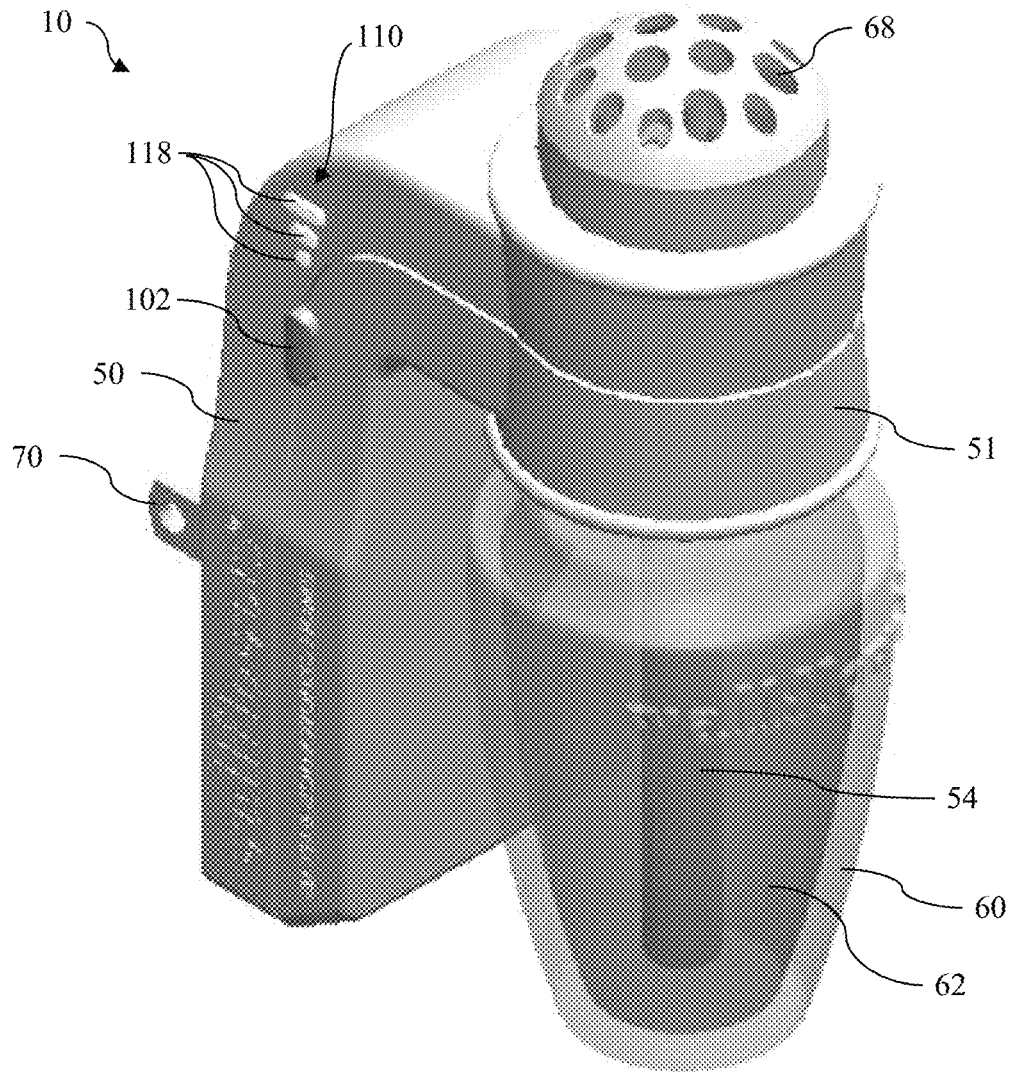
FIG. 1 is a perspective view of a diffuser according to embodiments disclosed herein.
Figure 2:
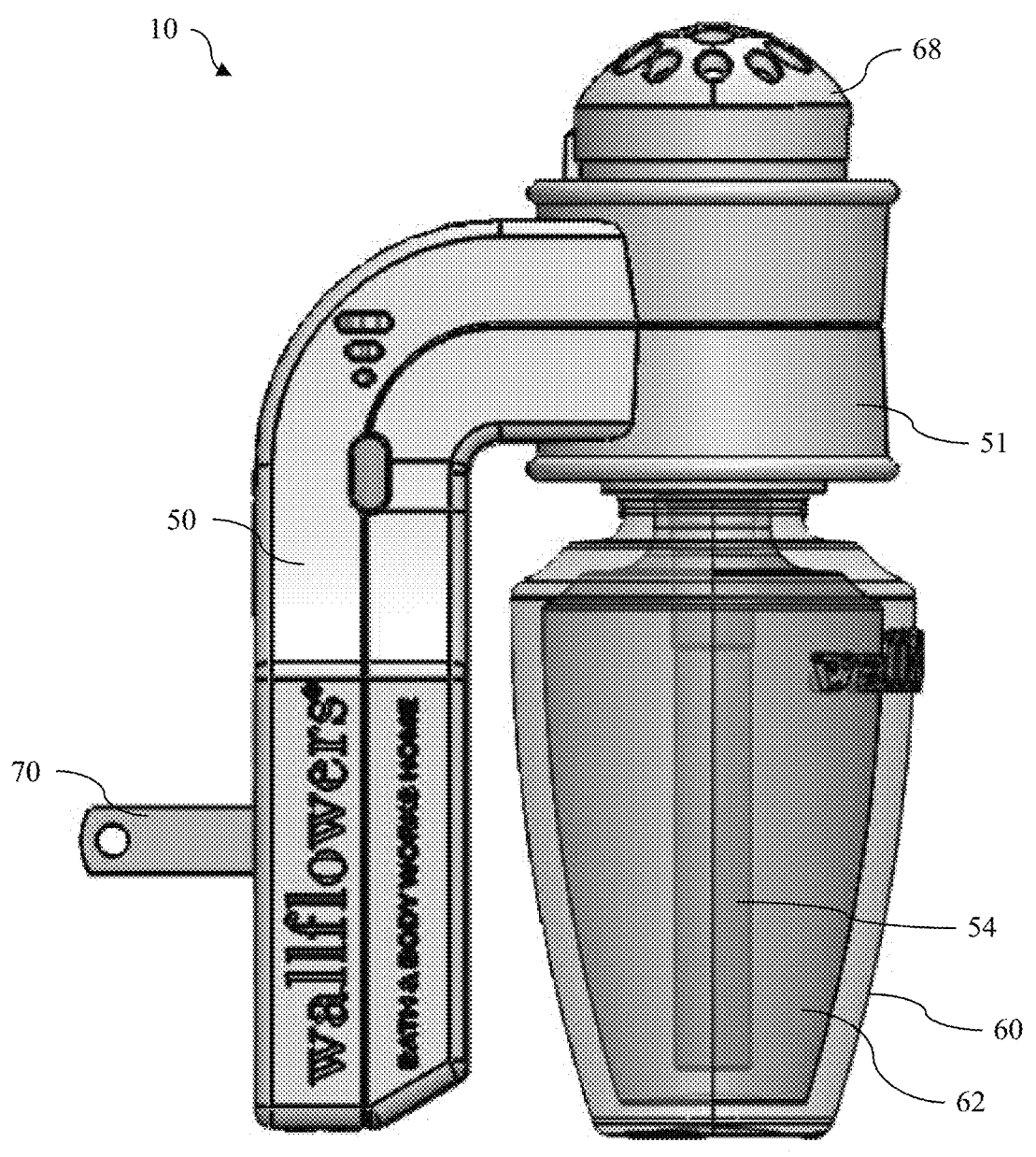
FIG. 2 is a side view of the diffuser as in FIG. 1.
Figure 3:
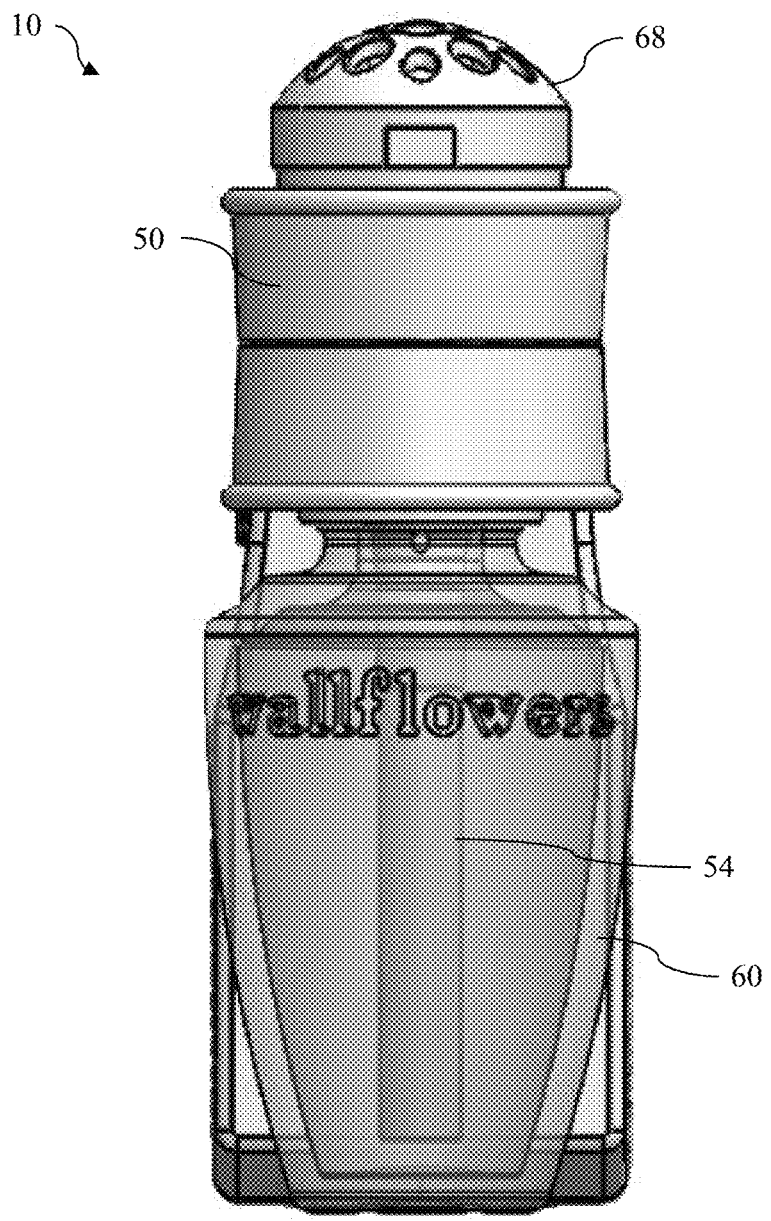
FIG. 3 is a front view of the diffuser as in FIG. 1.
Figure 4:
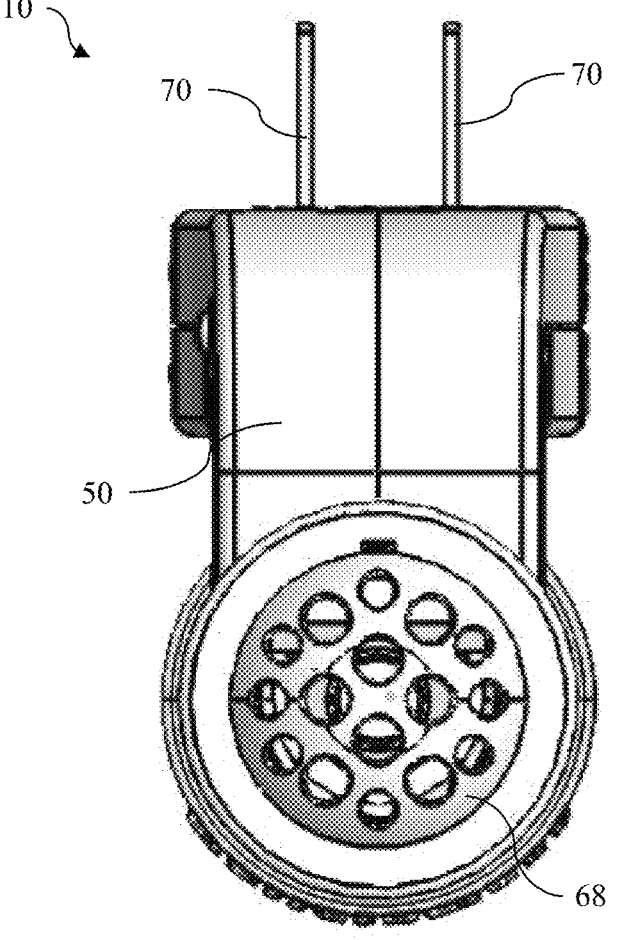
FIG. 4 is a top view of the diffuser as in FIG. 1.

The present invention now will be described more fully hereinafter with reference to the accompanying drawings, in which some, but not all, embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. It is to be understood that this invention is not limited to the particular methodology and protocols described, as such may vary. It is also to be understood that the terminology used herein is for the purpose of describing particular embodiments only, and is not intended to limit the scope of the present invention.

Many modifications and other embodiments of the invention set forth herein will come to mind to one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

As used herein the singular forms "a," "an," and "the" include plural referents unless the context clearly dictates otherwise. For example, use of the term "a sensor" can refer to one or more of such sensors, and so forth.

All technical and scientific terms used herein have the same meaning as commonly understood to one of ordinary skill in the art to which this invention belongs unless clearly indicated otherwise.

As used herein, the terms "optional" or "optionally" mean that the subsequently described event or circumstance may or may not occur, and that the description includes instances where said event or circumstance occurs and instances where it does not.

As used herein, the term "at least one of" is intended to be synonymous with "one or more of" For example, "at least one of A, B and C" explicitly includes only A, only B, only C, and combinations of each.

Ranges can be expressed herein as from "approximately" one particular value, and/or to "approximately" another particular value. When such a range is expressed, another aspect includes from the one particular value and/or to the other particular value. Similarly, when values are expressed as approximations, by use of the antecedent "approximately," it will be understood that the particular value forms another aspect. It will be further understood that the endpoints of each of the ranges are significant both in relation to the other endpoint, and independently of the other endpoint. Optionally, in some aspects, when values are approximated by use of the antecedent "approximately," it is contemplated that values within up to 15%, up to 10%, up to 5%, or up to 1% (above or below) of the particularly stated value can be included within the scope of those aspects.

The word "or" as used herein means any one member of a particular list and also includes any combination of members of that list.

It is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

The following description supplies specific details in order to provide a thorough understanding. Nevertheless, the skilled artisan would understand that the apparatus, system, and associated methods of using the apparatus can be implemented and used without employing these specific details. Indeed, the apparatus, system, and associated methods can be placed into practice by modifying the illustrated apparatus, system, and associated methods and can be used in conjunction with any other apparatus and techniques conventionally used in the industry.

Figure 5:
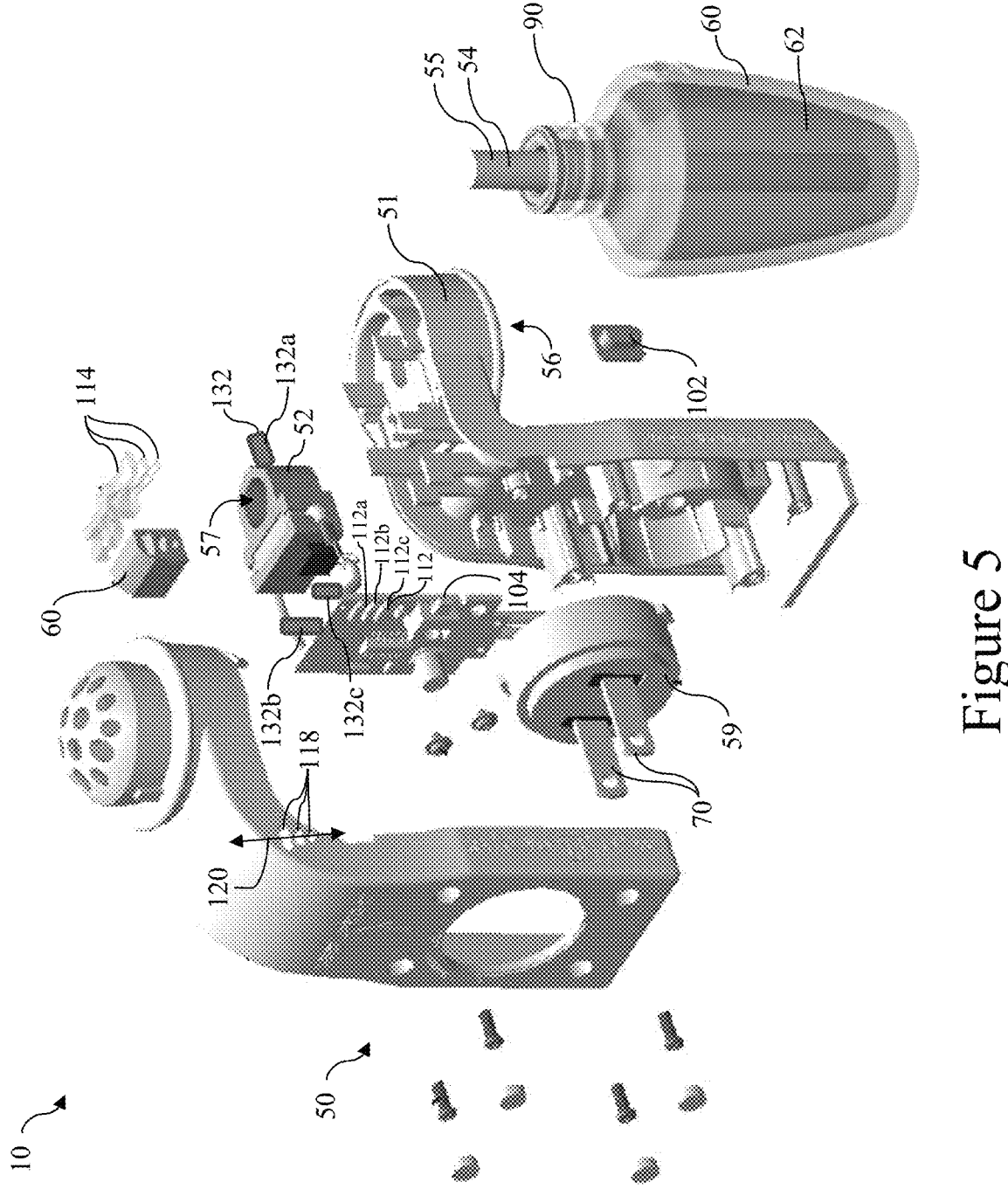
FIG. 5 is an exploded perspective view of the diffuser of FIG. 1.

Disclosed herein, in various aspects and with reference to FIGS. 1-5, is a plug-in fragrance diffuser/dispenser 10. As used herein, the terms "diffuser" and "dispenser" will be used interchangeably to refer to the same device. The scent diffuser 10 can comprise a multi-part plastic diffuser housing 50 containing a heater assembly 52 for heating an upper end 55 of a wick 54. The wick 54 can have a cylindrical shape (or other suitable shape), and the upper end 55 can be insertable into a hole 57 that extends through the heater assembly 52, as shown in FIG. 5. The diffuser housing 50 can include a receptacle (e.g., a socket 56, which can optionally be reverse threaded) which receives the upper reverse threaded neck end of a bottle 60 that contains a liquid 62 configured to produce an air freshening fragrance. As used herein, the term "bottle" refers to any container capable of containing a liquid that produces a fragrance as disclosed herein. Within this document, it should be understood that, in some contexts, the term "fragrance" refers to the scent produced as a result of the heating and vaporization of the liquid 62. However, in other contexts, it should be understood that the terms "liquid" and "fragrance" may be used interchangeably. The wick 54 can absorb the liquid 62 and bring it to the upper end 55 by capillary action like a sponge, where the liquid can be heated and vaporized by the heater assembly 52 to produce the fragrance.

Optionally, the bottle 60 can comprise a reverse screw thread 90 (FIG. 5). Thus, the bottle 60, when viewed from above, can be turned clock-wise to tighten it onto the housing 50 and counter-clock-wise to loosen and remove it. More generally, it is contemplated that the bottle 60 can comprise any structure that permits secure engagement with the housing 50. The socket 56, in a socket portion 51 of the housing 50, can hold the bottle in place with all but the neck of the bottle extending below the housing and being exposed so that it can be seen. In some aspects, the housing 50 can hold only one single bottle 60. In further aspects, the housing 50 can be configured to receive and dispense the fragrance from multiple bottles.

Optionally, the housing 50 can include a dome-shaped cover 68 having multiple holes in a pattern forming vapor outlets. The cover can optionally include a decorative upwardly and outwardly extending flange that mimics the leaves of a plant, the petals of a flower or other simulative shape. This shape can help conceal the dome, help dissipate the fragrance, and decorate the product as it rests near a wall, supported by a wall socket.

The device can be energized by receiving electricity through a pair of electrical plug blades 70 that are configured to be plugged into an electric wall outlet. Plug blades 70 can both supply electricity to, and support, the diffuser 10 in the wall outlet. A plug portion 59 of the housing 50 and the plug blades 70 can be made as one unit. Optionally, the plug portion 59 (with the plug blades 70) can be rotatable with respect to the remainder of the housing so that a user can select the orientation of the plug blades with respect to the remainder of the housing 50. In this way, the housing 50 can be oriented so that the bottle 60 hangs downwardly from the housing when the plug blades 70 are plugged into the wall.

The diffuser 10 can incorporate various other features disclosed in U.S. Pat. No. 6,236,807 to Richard Ruffolo et al., which granted May 22, 2001, and which is incorporated herein by reference in its entirety.

Although generally described and depicted herein as having a single heater and a single bottle, it is contemplated that the diffuser 10 can optionally comprise a plurality of bottles that contain respective liquids that are heated by one or more heater assemblies. Each bottle can be selectively secured to the housing of the diffuser 10 at a respective location (e.g., receptacle), with a respective wick positioned within each bottle. In some aspects, it is contemplated that a single heater can be configured to heat the liquid within each bottle. Alternatively, it is contemplated that a plurality of independently controllable heaters can be provided, with each heater associated with a location of a respective bottle. In embodiments in which multiple bottles are associated with the housing, it is contemplated that from two to 20 bottles can be provided. Accordingly, it is within the scope of the disclosed embodiments to provide a diffuser 10 having 1, 2, 3, 4, 5, 6, 7, 8, 9, 10, 11, 12, 13, 14, 15, 16, 17, 18, 19, or 20 bottles. Thus, when the following paragraphs disclose the modification or control of the output of a diffuser, it is contemplated that such modification or control can be applied to a single fragrance (in the case of a diffuser having a single bottle and a single fragrance) or to multiple fragrances (in the case of a diffuser having multiple bottles and multiple fragrances).

According to various embodiments, and as further disclosed herein, the diffuser 10 can comprise a controller 100 in electrical communication with the heater assembly 52.

Diffusers Using Pulse-Width-Modulated Electrical Voltage

Optionally, the controller 100 can be configured to regulate pulse-width-modulated (PWM) electrical voltage delivered to the heater assembly 52. It should be understood that the PWM electrical voltage can have a duty cycle defined as a percentage of time that the electrical voltage is on for a given cycle. A PWM electrical voltage with a higher duty cycle can cause the diffuser 10 to dispense the fragrance at a higher rate than a PWM electrical voltage with a lower duty cycle. References to the controller 100 providing electrical voltage to the heater assembly 52 should be understood to include any configuration by which the controller regulates electrical voltage. That is, it is not necessary that the controller itself output the electrical voltage to the heater assembly 52.

In exemplary aspects, the diffuser 10 can comprise a user input device in communication with the controller. Upon receiving an input from a user, the user input device can cause the controller 100 to change the duty cycle of the PWM electrical voltage. Optionally, the user input device can comprise a button 102 that actuates a momentary switch 104 in communication with the controller 100. Other examples of the user input device include a dial, a slide, and other switches as are known in the art. The controller 100 can, in response to actuation of the momentary switch 104, change the duty cycle of the electrical voltage provided to the heater assembly 52.

In one embodiment, the controller can output PWM electrical voltage at a plurality of different duty cycles, such as, for example and without limitation, two, three, four, five, or more different duty cycles. In exemplary aspects, the controller can output PWM electrical voltage at three different duty cycles. For example, the controller can output PWM electrical voltage with a duty cycle of 25%, 50%, or 100%, respectively corresponding with low, medium, and high settings. However, it is contemplated that other duty cycles can be used. For example, the low setting can correspond to a duty cycle ranging from about 10% to about 40%, the medium setting can correspond to a duty cycle ranging from about 35% to about 75%, and the high setting can correspond to a duty cycle ranging from about 70% to about 100%, with the duty cycle of the medium setting being greater than the duty cycle of the low setting and the duty cycle of the high setting being greater than the duty cycle of the medium setting. In some aspects, the duty cycles can regulate the power to the heater so that the low setting uses 1.8 W, the medium setting uses 2.0 W, and the high setting uses 2.7 W. However, other voltage outputs for each setting are possible. In some embodiments, the controller 100 can also be set to an "off" setting in which it provides little or no voltage to the heater. The modulation frequency can optionally range from about 1 kHz to about 100 kHz. It is contemplated that, by using a variable duty cycle, the heater and, thus, fragrance output, can be controlled without the use of a resistor-based voltage divider. In this way, the use of the variable duty cycle can reduce the power consumption and avoid excessive heat caused by a voltage divider. Moreover, elimination of the voltage divider can eliminate circuit complexity and reduce the minimum size of the housing 50. For example, the resistor circuit of the voltage divider produces excessive heat that requires a separate chamber or thermal barrier to isolate the heat from the wick, as well as a means for expelling heat. Thus, use of a voltage divider increases the required size for the housing. Additionally, an unexpected benefit of using PWM electrical voltage is that regardless of voltage differences from a wall outlet, the diffuser 10 can have consistent fragrance output. It should be understood that, because voltage levels can fluctuate from house to house, the fluctuating voltage levels can limit the predictability of the fragrance output. Such fluctuations are particularly noticeable in configurations where voltage dividers are used. In contrast, when PWM electrical voltage is used as disclosed herein, users can have a consistent fragrance output regardless of where they are located (even if there are significant differences in voltage levels among user locations).

When the diffuser 10 is plugged in, the controller can optionally default to one setting (e.g., the medium setting). When a user depresses the button 102 a first time (or otherwise activates a user input device a first time), the controller 100 can change the duty cycle to a different cycle. For example, after the user depresses the button 102 a first time, the controller 100 can change the duty cycle to the low setting. After depressing the button 102 a second time, the controller 100 can change the duty cycle to the "off" setting. After depressing the button 102 a third time, the controller 100 can change the duty cycle to the high setting. And after depressing the button 102 a fourth time, the controller 100 can change the duty cycle back to the medium setting. Although this specific sequence is disclosed, it is contemplated that other sequences of duty cycle changes are possible. For example, rather than starting at the medium setting, it is contemplated that the default setting can be the low setting, with each sequential press of the button (or other activation of the user input device) resulting in a transition to the medium setting, then the high setting, and then the "off" setting before the sequence repeats again. In further embodiments, the diffuser can exclude the "off" setting. Accordingly, in these embodiments, upon each sequential pressing of the button 102, the controller can be configured to change the duty cycle among the low, medium, and high settings (for example, from low to medium, from medium to high, and from high to low). In further embodiments, the diffuser can be configured to change the duty cycle to the low setting upon receiving a first button press, the medium setting upon receiving two button presses, and the high setting upon receiving three button presses.

The diffuser 10 can further comprise an indicator 110 that shows the controller's duty cycle setting. The indicator 110 can comprise a plurality of status lights (e.g., three LEDs 112). The LEDs 112 can emit light into respective light pipes 114 that are disposed in a housing 116. The light pipes 114 can deliver the light from the LEDs 112 through apertures 118, which can be defined within a status display portion of the housing. Optionally, the apertures 118 can be aligned along a vertical axis. The apertures 118 can have respective opening areas that increase in size along the axis (e.g., from the bottom to the top). In some aspects, the apertures 118 can each have a slot shape (i.e., semicircular opposing sides and linear portions extending between the semicircular opposing sides). The LEDs can illuminate in sequence so that at the low setting, only a first LED 112A is illuminated, at the medium setting, the first LED 112A and a second LED 112B are illuminated, and at the high setting, the first and second LEDs 112A, 112B and a third LED 112C are illuminated. Alternatively, it is contemplated that only a single light 112 can be illuminated during each respective duty cycle. Thus, in use, the lights 112 and the heating assembly 52 can be controlled with a single controller, which can reduce the required size of the housing 50 and decrease overall complexity of the circuitry as compared to a device requiring separate controllers to control the light and heating assembly. In providing pulse-width-modulated electrical voltage, the lights can be LEDs that can be variably illuminated, with the intensity of the lights varying based upon the variable duty cycle. It should be understood that if the heater assembly 52 was powered via a variable voltage instead of a variable duty cycle, the variable voltage could be insufficient to illuminate the LEDs.

In some embodiments, the diffuser 10 can comprise at least one nightlight 132 (optionally, a plurality of nightlights). In some embodiments, the at least one nightlight 132 of the diffuser 10 can comprise a forwardly emitting LED 132A, an upwardly emitting LED 132B, and/or a downwardly emitting LED 132C. In these embodiments, it is contemplated that the at least one nightlight 132 can extend outwardly from the housing 50 or emit light through respective openings in the housing 50. Additionally, or alternatively, in various other aspects, one or more LEDs can be positioned within, and thereby illuminate, the housing 50. The nightlight 132 can have an intensity that varies based on the duty cycle. For example, a high duty cycle can correspond to a high nightlight intensity, and a low duty cycle can correspond to a low nightlight intensity. In some embodiments, the nightlight 132 and the heating assembly 52 can be on the same circuit. That is, the same voltage can be provided to the nightlight 132 and the heating assembly 52. In some embodiments, the nightlight 132 can be connected in series with the heating assembly's resistor. In further embodiments, the nightlight 132 can be separately connected to the power source through a current limiting resistor. In this way, the nightlight 132 and heating assembly 52 can be controlled with a single controller, which can reduce the required size of the housing 50 and decrease overall complexity of the circuitry as compared to a device requiring separate controllers to control the light and heating assembly. In providing pulse-width-modulated electrical voltage, the nightlight 132 can be an LED that can be variably illuminated. It should be understood that if the heater assembly 52 was powered via a variable voltage instead of a variable duty cycle, the variable voltage could be insufficient to illuminate the LED of the nightlight. Although described herein as being connected in series with the resistor of the heating assembly, it is contemplated that the nightlight 132 can also be connected with the heating assembly in other configurations, such as a parallel connection. In further embodiments, the diffuser 10 can comprise a light detector 134 (e.g., a photodetector, such as a phototransistor, a photodiode, or photonic integrated circuit) that is configured to detect ambient light. The diffuser can be configured to turn on the nightlight 132 when the detected ambient light has dropped below a first threshold and turn off the nightlight 132 when the detected ambient light has risen above a second threshold. Further, the controller 100 can be configured to vary the nightlight's illumination intensity based on the detected ambient light. For example, the nightlight can be illuminated to a first intensity when the light detector detects no ambient light and a second, brighter intensity when the light detector detects some ambient light.

Additional Diffuser Features

Figure 6:
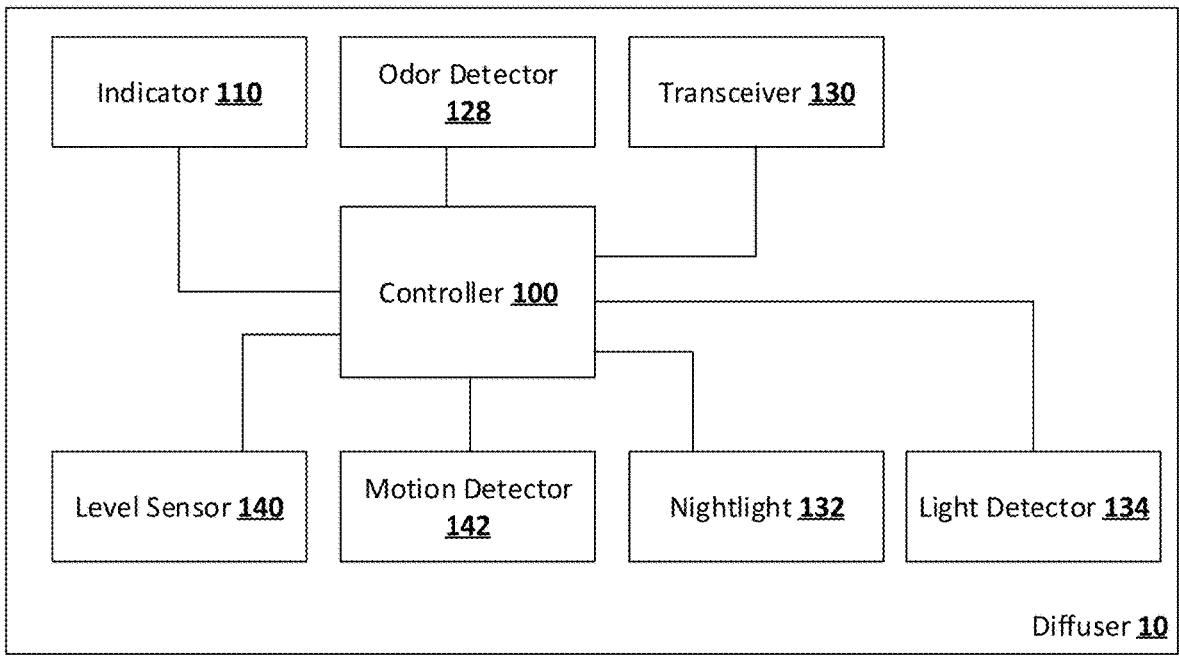
FIG. 6 is a schematic of the diffuser as in FIG. 1.

Referring to FIG. 6, the diffuser 10 can comprise an odor detector 128. Optionally, the odor detector 128 can comprise one or more of the following sensors: a gas sensor array; a chemiresistor; a metal-oxide semiconductor (MOSFET) device with a variable output signal that changes in response to the presence of charged particles; a conductive polymer sensor (e.g., polypyrrole); a tin-oxide gas sensor; a polymer composite sensor (e.g., including a conducting material such as carbon black); a quartz crystal microbalance sensor; or a surface acoustic wave (SAW) sensor. The diffuser 10 can be configured to dispense fragrance in response to the odor detector 128 detecting a foul odor. In some embodiments, the odor detector can detect a level or type of foul odor, and the controller can set the fragrance intensity based on the level or type of foul odor. For example, in exemplary aspects, it is contemplated that the controller 100 can be configured to increase a fragrance output for a predetermined period time after a foul odor is detected or to maintain an increased fragrance output for as long as a foul odor is continuously detected. In these aspects, it is further contemplated that the fragrance output can be reduced during periods when a foul odor is not detected or when the level of the foul odor is decreased.

The diffuser 10 can comprise a transceiver 130 that can communicate with a computing device, such as, for example, a smartphone, a tablet, a smartwatch, or the like. The computing device (e.g., smartphone or tablet) can interface via an application to enable a user to change the duty cycle of the PWM electrical voltage provided to the heater assembly. In further embodiments, the application can enable the user to turn the diffuser on and off. In yet further embodiments, the application can enable a user to schedule when the diffuser is on or off, and at what diffusion rates the fragrance is dispensed. For example, a user can schedule a diffuser at his or her house to dispense fragrance shortly before the user expects to arrive home. Similarly, a user can schedule a diffuser to turn off during periods of time when the user is expected to be out of the house.

According to various aspects, the diffuser 10 can be controlled through a cloud computing device 1014*a* that is accessed via an audio or voice assistant as is known in the art, such as, for example, a smart speaker (e.g., ALEXA or GOOGLE HOME speakers). In further aspects, the diffuser 10 can be controlled via visual signals, such as hand motions. For example, the diffuser 10 or a device controlling the diffuser 10 can comprise a camera that captures movement, and the movement can be compared to registered movements that cause the diffuser to respond. In still further aspects, the diffuser 10 can be controlled via a cloud computing device. The cloud computing device can have user settings that control the diffuser 10. In still further aspects, the cloud computing device can have user settings that are controlled by an audio or voice assistant, visual signals, web interface or smartphone or tablet app (or other application for a computing device). For example, the user settings can cause the diffuser to dispense on certain days of the week or days of the year, at certain times, etc.

In some embodiments, the remote computing device can control the nightlight(s) 132. For example, the application can provide the user with options for selecting the nightlight's brightness. Optionally, the application can provide the user with settings (e.g., high, medium, low, off) or provide a slider for selecting the brightness. In response to receiving a user selection, the controller can vary the PWM electrical voltage delivered to the nightlight 132. In further aspects, the application can enable the user to select the nightlight's color. For example, using RGB (red/green/blue) LEDs, the app can set the output level of each color of the RGB LEDs to create a full array of colors. Optionally, the LEDs can be set to specific hues or configured to change hues on a timed basis.

In some embodiments, the diffuser 10 can comprise a level (volume) sensor 140. The controller 100 can be configured to determine a level of liquid remaining in the bottle 60 based on a signal from the level sensor 140. In some embodiments, the level sensor 140 can detect whether the amount of liquid 62 is above or below a sensing level. As the amount of liquid 62 falls below the sensing level, the level sensor 140 can send a signal to the controller indicating that the level sensor is below the sensing level. In this way, the controller 100 can determine when the bottle 60 is empty or near empty. In further embodiments, the level sensor 140 can comprise a plurality of sensors spaced along the height of the bottle 60, and each sensor can determine if the liquid 62 is at or below the respective sensor's sensing level. Accordingly, the level sensor 140 can determine, based on which sensors are presently detecting the liquid 62, the approximate level of the liquid 62 in the bottle 60. It is contemplated that the level sensor 140 can comprise any conventional sensor that is capable of sensing a level of the liquid 62 or detecting when a level of the liquid 62 falls below a threshold volume. Such sensors are known to make use of a variety of sensing methods, including, for example and without limitation, changes in optical or electrical measurements. In still further embodiments, the computing device 1001 can be connected with a camera 1040. The computing device 1001 can communicate with the remote computing device 1014a to provide any data, including image data. The remote computing device 1014a can, in turn, communicate with the diffuser 10.

In further embodiments, the controller 100 can estimate the quantity of liquid in the bottle 60 based on its use. For example, the controller can approximate to the rate at which fragrance is emitted from the diffuser 10. The controller can account for duration of use and the rate at which fragrance is being diffused based on the duty cycle of the voltage delivered to the heater. In further embodiments, the controller can account for time during which the heater is off, as the fragrance can diffuse slowly in the absence of heat from the heater.

In still further embodiments, the controller can account for which type of liquid is in the bottle in determining the amount of remaining liquid. It is contemplated that different fragrances can diffuse at different rates. That is, some liquids can be used faster than others. Accordingly, in some embodiments, the controller can receive information from the computing device. Optionally, the computing device 1001 can be provided with a camera 1040, as further disclosed herein. For example, the computing device 1001 can be a smartphone or tablet having a camera. The computing device 1001 can use the camera 1040 and image recognition software to recognize an identifier on the bottle 60 (e.g., a barcode, a QR code, a string of characters, a unique pattern), the shape of the bottle 60, or packaging for the bottle 60 (e.g., a barcode on a box in which the bottle 60 is packaged). In still further embodiments, the computing device 1001 can receive an input from a user that identifies the type of fragrance bottle 60 installed in a given diffuser 10 (e.g., via a pick list in an application executed by the computing device).

In further embodiments, the estimating of remaining liquid in the diffuser can be performed by the computing device 1001. For example, the computing device 1001 can be in communication with a lookup table possessing information concerning the expected usage/diffusion rate of various fragrance-producing liquids. After the computing device 1001 detects an identifier of a type of fragrance bottle 60 or receives an input from a user identifying the type of fragrance bottle 60 installed in a given diffuser 60, the computing device 1001 can be configured to access the lookup table to determine the expected usage/diffusion rate of the identified type of liquid within the fragrance bottle 60. This expected usage/diffusion rate can then be used by the computing device to estimate the time when the level of liquid has fallen below a threshold value (factoring in the total time during which the diffuser is activated). In still further embodiments, the remote computing device 1014a can be configured to access the lookup table to determine the expected usage/diffusion rate of the identified type of liquid within the fragrance bottle 60. This expected usage/diffusion rate can then be used by the remote computing device 1014a to estimate the time when the level of liquid has fallen below a threshold value (factoring in the total time during which the diffuser is activated).

Systems Comprising Multiple Diffusers

Figure 7A:
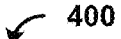
FIGS. 7A-7C are schematics of various network configurations including a plurality of diffusers as disclosed herein.
Figure 7A:
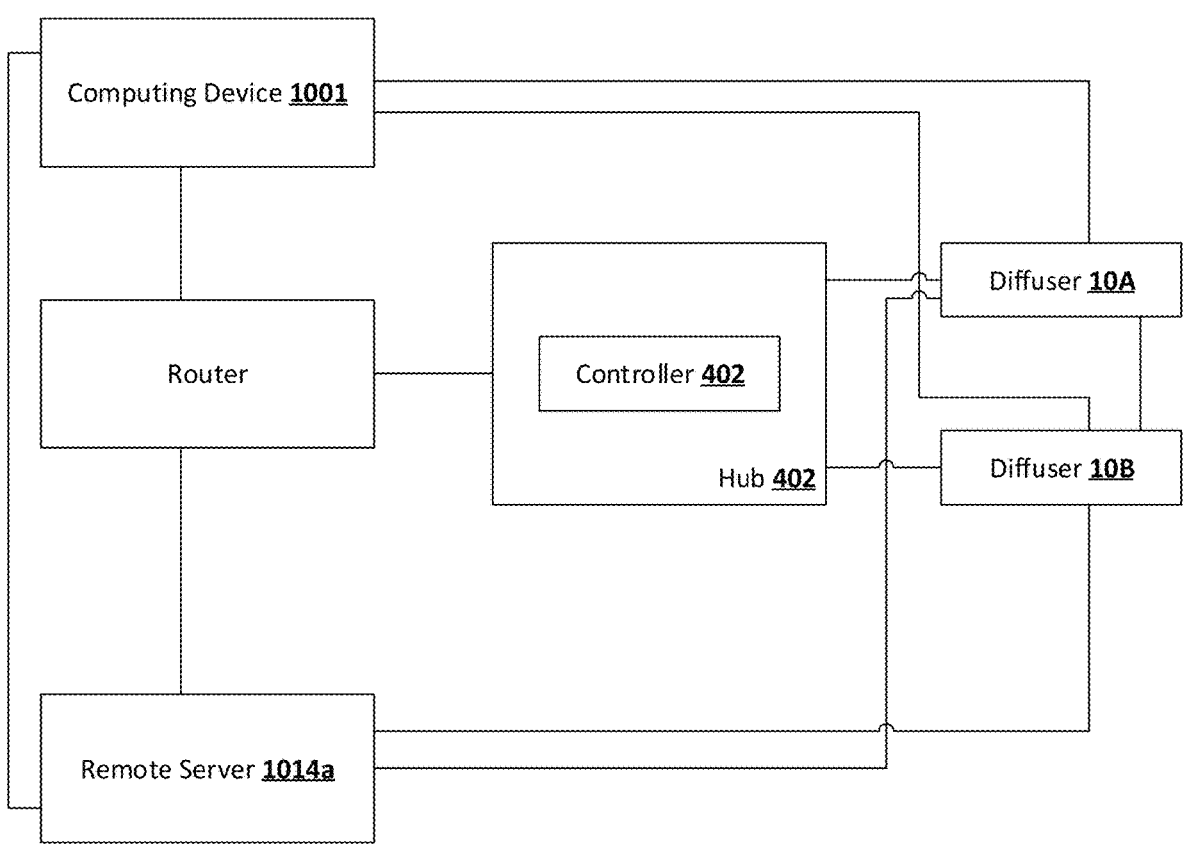
Figure 7B:
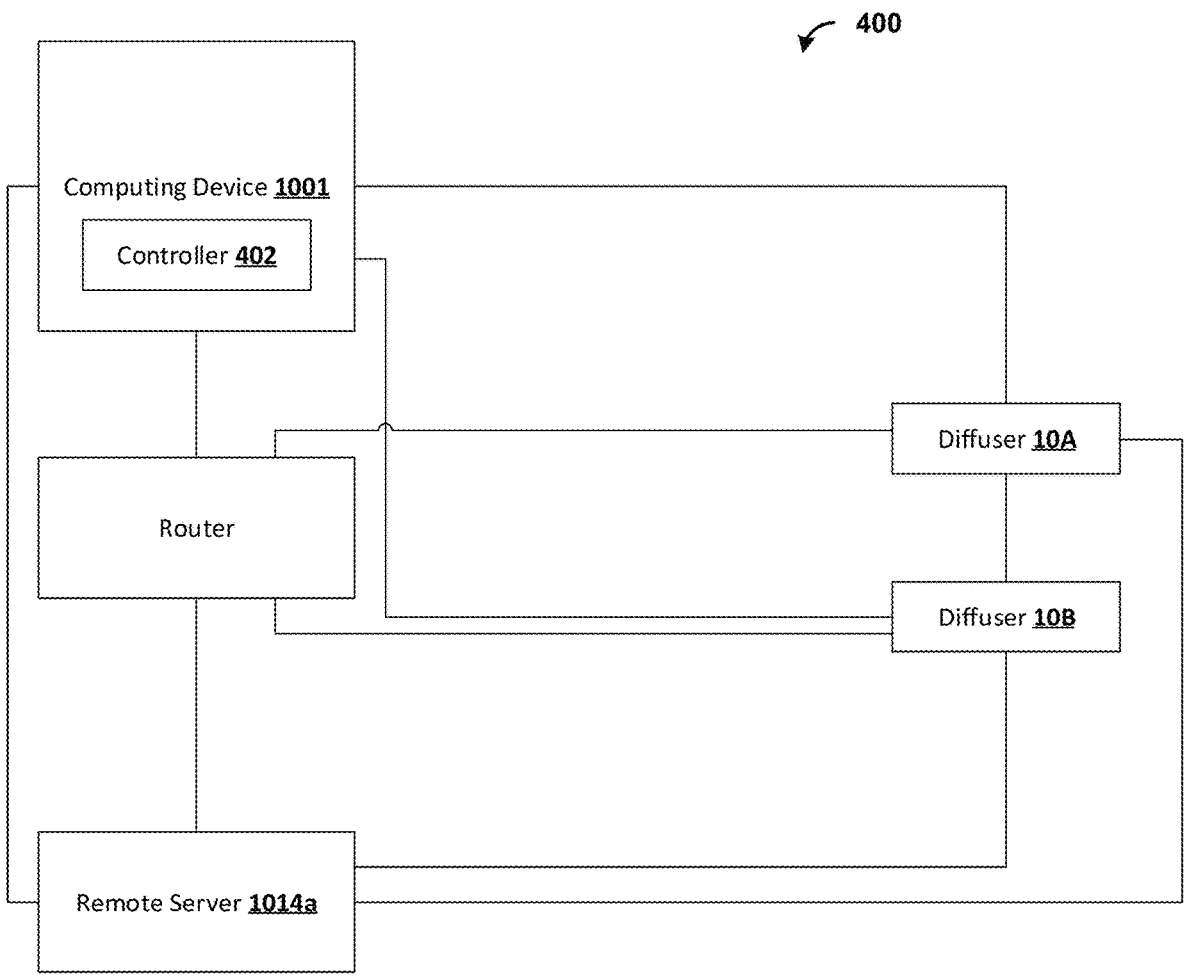
Figure 7C:
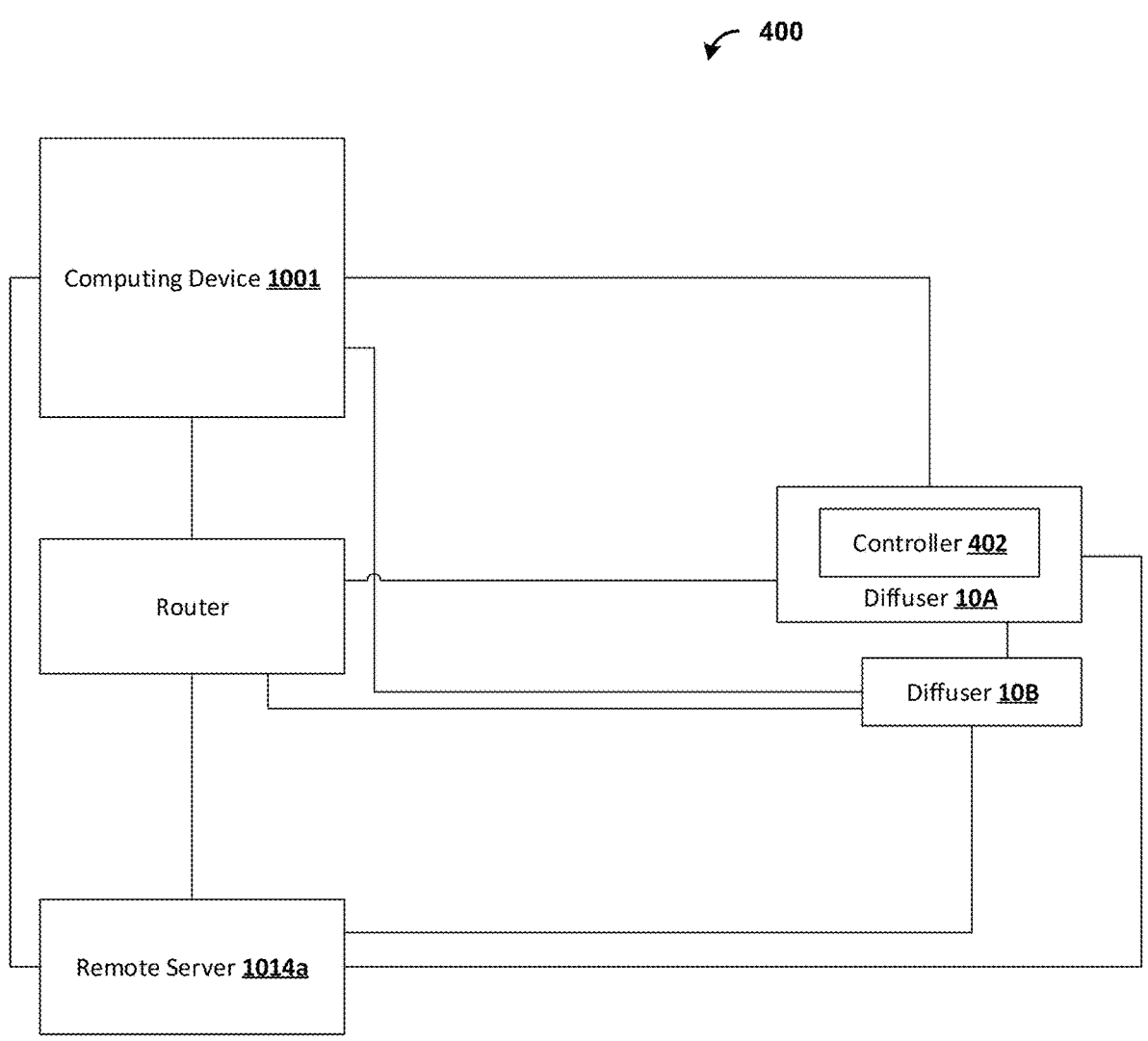

Referring to FIGS. 7A-7C, in some embodiments, a plurality of diffusers 10 can be integrated into a system 400. For example, the system 400 can comprise a first diffuser 10A and a second fragrance diffuser 10B. The system 400 can be networked through a controller 402. In some aspects, the controller 402 can serve as a coordinating controller that coordinates the output of each of the first diffuser 10A and the second diffuser 10B. In some embodiments, the controller 402 can be an independent hub 404 as shown in FIG. 7A.

In further embodiments, and as shown in FIG. 7B, the controller 402 is provided as a component of a remote computing device 1001, such as, for example and without limitation, a smartphone or a tablet. In these embodiments, it is contemplated that the controller 402 can be provided as a processor 1003 of the remote computing device 1001 as further disclosed herein. In further embodiments, and as shown in FIG. 7C, the controller 402 can be a controller 100 of one of the diffuser 10A and the second fragrance diffuser 10B, and the first and second diffusers 10A, 10B can be configured in a primary-secondary (e.g., master-slave) configuration. Accordingly, although the disclosure refers to the controller 402 as a separate hub, it is contemplated that some or all of the aspects of the controller 402 can be integrated into and performed through the controller 100 of a diffuser 10.

In some aspects, the diffusers 10A, 10B and the computing device 1001 can communicate directly, while in further aspects, the diffusers 10A, 10B and the computing device can communicate through a hub or router. The diffusers 10A, 10B can communicate with the computing device 1001 via various communication methods, including radio frequency communication, such as, by way of example, Bluetooth, 802.11 (Wi-Fi) protocols, or other point-to-point radiofrequency communication protocols. The devices can also communicate via public wireless networks using protocols such as CDMA, GSM, 3G, LTE, 4G, or other protocols known in the art. In yet another alternative exemplary embodiment, the devices can transmit information via nonradiofrequency methods, such as infrared (IR) communications. As one of skill in the art would understand, the devices can use any method of wired or wireless communication to transmit and receive an instruction or signal, including any optical, radio, or auditory frequency. In various aspects, the computing device 1001 can interface with a remote cloud computing device (e.g., remote server 1014a) and, through the remote cloud computing device, control the diffusers 10A, 10B. That is, the computing device 1001 can communicate with the remote server 1014a, and the remote server 1014a can, in turn, communicate with the controller 402.

The controller 402 can control the diffusion rate of each diffuser 10. In some embodiments, the controller 402 can control the output rate of the first diffuser 10A based on the output rate of the second diffuser 10B. For example, when the controller 402 determines that the fragrance-producing liquid of the second diffuser 10B has been depleted or decreased below a threshold level (e.g., after receiving a signal from the level sensor 140 of the second diffuser 10B), the controller 402 can increase the diffusion rate of the first diffuser 10A to maintain a desired (combined) output.

According to some aspects, the controller 402 can determine a relative spacing between the first diffuser 10A and the second diffuser 10B, and the controller can determine the output rate of the first diffuser 10A and/or the second diffuser 10B based the spacing between the first and second diffusers. Optionally, it is contemplated that the computing device 1001 can execute an application that permits optical measurement of a spacing between respective diffusers (using the camera of the computing device). In further aspects, a user can input spacing via an application on the computing device between the first diffuser 10A and the second diffuser 10B (e.g., ten feet, twenty feet, forty feet, etc.). In further embodiments, the controller 402 can use Wi-Fi or Bluetooth received signal strength indicator (RSSI) values to determine relative proximity to the respective diffusers. In further embodiments, the computer device 1001 can execute an application that permits TOF (Time of Flight) or infrared sensors to determine the spacing between respective diffusers (using sensors of the computing device.) In further embodiments, the computing device 1001 can execute an application that permits accelerator and GPS measurement to determine the spacing between respective diffusers (using sensors of the computing device.) According to further aspects, the controller 402 can determine room square footage or volumetric space in which a given diffuser is disposed and the room in which the diffuser is disposed. For example, a user can input the room size (either in total square feet or room dimensions) via the application executed by the computing device. The controller 402 can adjust the output rate of the diffuser based on such information. For example, the controller 402 can be configured to increase an output rate for larger rooms and to decrease an output rate for smaller rooms. In further embodiments, the computing device 1001 can execute an application that uses augmented reality measurements of the length and width of the room (using sensors of the computer device and application programming interfaces (APIs) that are available in the computing device's operating system) to determine the room size. In further embodiments, the controller 402 can execute ultrasound emissions to determine the size and space of the room. The controller 402 can adjust the output rate of the diffuser based on such room size and space of the room and/or the spacing between diffusers within the room (or other area). For example, the controller 402 can be configured to increase an output rate for larger rooms and to decrease an output rate for smaller rooms. As another example, for a room comprising three or more diffusers, it is contemplated that the diffusers that are closest together can have lower output rates than the more isolated diffuser(s) (that are spaced farther away from the more clustered diffusers), thereby maintaining a consistent distribution of fragrance throughout the room. Thus, if first and second diffusers are spaced apart by five feet and a third diffuser is spaced from the first and second diffusers by 15 to 20 feet, then it is contemplated that the output of the third diffuser can be increased and the outputs of the first and second diffusers can be decreased to achieve a desired (i.e., consistent or substantially consistent) distribution or intensity of fragrance throughout the room.

In some embodiments, the controller 402 can be configured to mix the outputs of the first diffuser 10A and the second diffuser 10B to produce a combined scent profile. The controller can receive inputs of the diffusers' respective fragrances. Optionally, in exemplary aspects, it is contemplated that the first fragrance and the second fragrance can be different from one another but combine to provide a complementary scent profile. In exemplary aspects, it is contemplated that the user can input a desired relative distribution of the respective fragrances, and the computing device can be configured to continuously adjust the output of the diffusers to maintain the desired distribution. In these aspects, it is further contemplated that the user can selectively adjust an intensity of the combined scent profile so that the outputs of the diffusers can be increased or decreased while still maintaining the desired relative distribution of the respective fragrances. In still further aspects, it is contemplated that predetermined "recipes" of combined fragrances can be downloaded by the computing device (through an application or online interface). In these aspects, following download of the recipe, the user can instruct the computing device to dispense fragrance in accordance with the recipe. Thus, in some aspects, it is contemplated that the same two fragrances can be provided in different proportions to produce different scent profiles. For example, it is contemplated that a plurality of different recipes can exist for a single pair of fragrances. In use, it is contemplated that the controller 402 can be configured to account for room size, diffuser spacing, diffusion rate, and other factors to selectively adjust the diffusion of fragrance to achieve a desired scent profile that is consistent with a downloaded recipe, a user-selected distribution, and/or a user-selected fragrance intensity. In some embodiments, a specific mix ratio can be provided to the controller 402. For example, a user can download a recommended mix ratio provided by a fragrance provider (e.g., manufacturer/seller) on the remote server 1014*a*. In further embodiments, the user can input a desired mix ratio.

In still further embodiments, the application can enable the user to set the dispenser 10 to respond in various ways according to various conditions. According to some aspects, a motion sensor can detect the presence of a person in a room, and the dispenser can turn on in response to the detection of the person in the room. Exemplary motion sensors can include passive infrared sensors, microwave sensors, ultrasonic transducers, video cameras, and/or gesture detectors (such as those using photodetectors in combination with infrared lighting elements), and combinations thereof. According to further aspects, the user can set the location of the dispenser 10. Using the dispenser's location, the system 400 can determine a proximity between the dispenser 10 and the remote computing device 1001. For example, when the remote computing device is a smartphone or tablet, it is contemplated that the proximity between the dispenser and the smartphone or tablet can be determined using the GPS of the smartphone or tablet. The system 400 can, based on proximity of the remote computing device and the dispenser 10, turn the dispenser on and off. For example, the system can turn the dispenser on when the remote computing device 1001 is within a certain radius of the dispenser 10 (or on the same local network (e.g., Wi-Fi network). In this way, a dispenser 10 at a user's home can turn on as the user, carrying the remote computing device 1001, approaches home. According to some aspects, at least one dispenser 10 of the system 400, or, optionally, all of the dispensers 10 of a system, can be controlled via a remote or local computing device. For example, a plurality of devices, including at least one dispenser 10 can be in communication via an Internet of things (IoT) network. The dispenser 10 can be configured to change a setting (e.g., turn on or off or change the fragrance output rate) based on a condition. Such IoT devices can include a smart speaker, a smart thermostat, or a smart lighting device (e.g., a smart bulb or smart lighting hub). For example, the IoT devices can have a nighttime mode or an away mode, in which the dispenser can be configured to turn off, and a daytime or at home mode, in which the dispenser can be configured to turn on. The IoT devices, including the dispenser(s) 10 can be configured to change a setting upon activation of another IoT controlled device (e.g., when a fan or HVAC system turns on). In further aspects, it is contemplated that the dispensers 10 can be controlled via cloud computing control.

Figure 9:
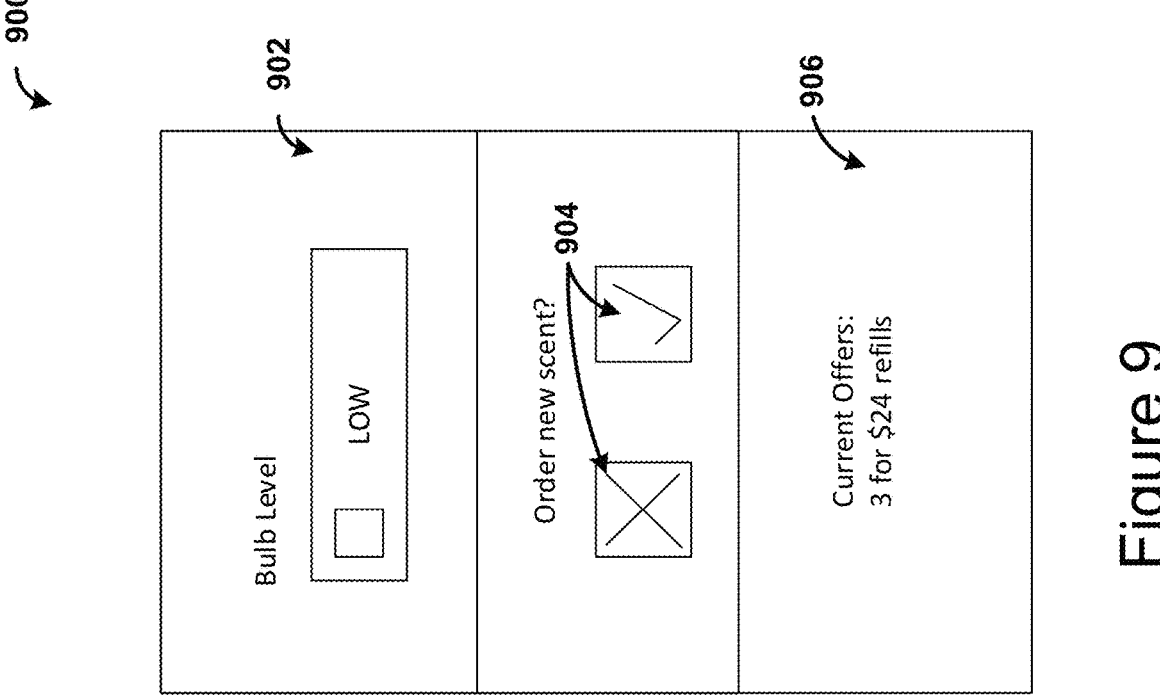
FIG. 9 is schematic depicting an exemplary interface on the computing device.

According to some aspects, upon receiving a signal that the bottle 60 of a given diffuser 10 is empty or has a level below a threshold (from the level sensor), the application can inform the user via a notification. Referring also to FIG. 9, the application can further recommend a fragrance through a user interface 900 on the computing device 1001 (e.g., smartphone or tablet) or other interface mechanism (such as an audio or video assistant as are known in the art), through either an application or browser that permits streamlined reordering of the fragrance. In some aspects, the application can recommend the same fragrance. In further aspects, the application can recommend a different fragrance based on the user's purchase history or a time of year. As one example, as a holiday approaches (e.g., Thanksgiving), the system 400 can recommend that holiday-themed fragrances (e.g., fragrances associated with Thanksgiving) be purchased. According to one embodiment, a user interface 900 can provide an indication 902 to the user that the fragrance is low. Optionally, the indication 902 can comprise an alert having text, a color change, a graphics change, an audible signal/alert, or combinations thereof. The user interface 900 can further provide the user with selectable buttons 904 (e.g., buttons defined on a touchscreen of a smart device) for purchasing or not purchasing more fragrance. The user interface 900 can additionally provide information 906 to the user, such as shopping deals associated with the purchase of more fragrance.

The system 400 can determine the number of diffusers in a given area (e.g., household, building, or portion of a building). The given area can be associated with a given account. For example, an account can be associated with a given area, and a plurality of diffusers can be associated with said account, thereby associating the plurality of diffusers with the given area. In use, it is contemplated that the controller 402 can be configured to adjust the relative fragrance outputs of the diffusers in the given area based upon the total number of diffusers in the area. In some aspects, a user can input the area of a room in which a diffuser, or a plurality of diffusers are located. The user can optionally input the ceiling height of the room. Further, the user can input the number of devices in the room. In further aspects, the controller can determine the room size using other methods as further disclosed herein (e.g., using ultrasonic sensors). Additionally, or alternatively, it is contemplated that the controller 402 can be configured to determine the total number of diffusers in communication with the controller. Using this information, the controller 402 can regulate the fragrance output.

According to some aspects, the system 400 can determine preferred fragrances or diffuser types for a given household or region. In further aspects, the system 400 can determine preferred fragrances or diffuser types based on the time of year or season. This information can be used for market research to determine preferred fragrances and diffuser types for different regions or households. Such information can be used to determine projected inventory for particular areas. Further, such information can be used to provide product recommendations to individual customers for improved customer experience.

Computing Device

Figure 8:
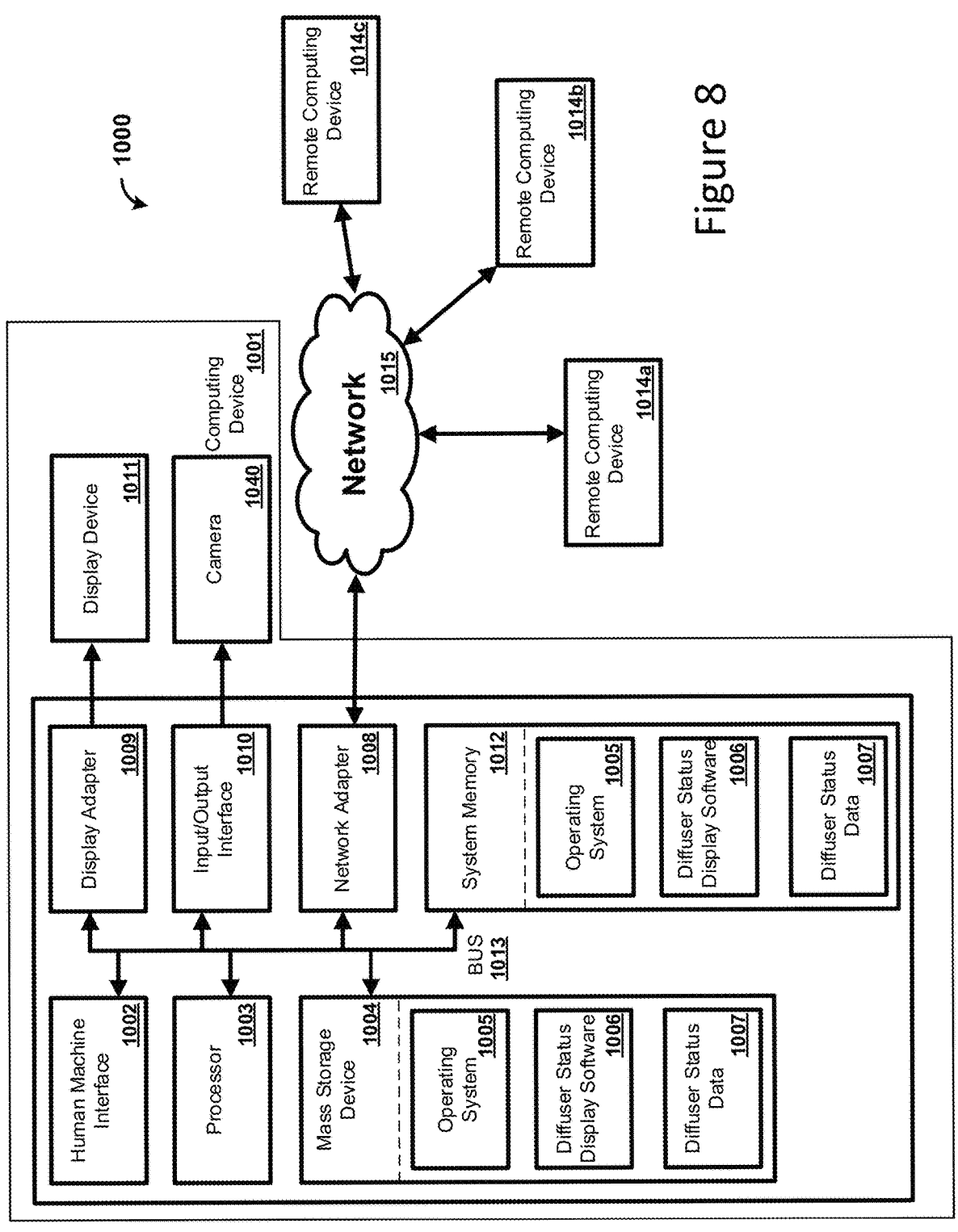
FIG. 8 is a schematic of a computing device for use with a diffuser as disclosed herein.

FIG. 8 shows a system 1000 including a computing device 1001 for use with the diffuser 10. In exemplary aspects, the computing device 1001 can be a smart device (e.g., smartphone, smart watch, activity tracker, smart apparel, smart accessory, or smart home hub) or a tablet. More generally, it is contemplated that the computing device 1001 can be any device or structure having one or more of the components disclosed herein. Additional examples of computing devices 1001 include personal computers, computing stations (e.g., workstations), and portable computers, such as laptop computers.

The computing device 1001 may comprise one or more processors 1003, a system memory 1012, and a bus 1013 that couples various components of the computing device 1001 including the one or more processors 1003 to the system memory 1012. In the case of multiple processors 1003, the computing device 1001 may utilize parallel computing.

The bus 1013 may comprise one or more of several possible types of bus structures, such as a memory bus, memory controller, a peripheral bus, an accelerated graphics bus, and a processor or local bus using any of a variety of bus architectures.

The computing device 1001 may operate on and/or comprise a variety of computer readable media (e.g., non-transitory). Computer readable media may be any available media that is accessible by the computing device 1001 and comprises, non-transitory, volatile and/or non-volatile media, removable and non-removable media. The system memory 1012 has computer readable media in the form of volatile memory, such as random access memory (RAM), and/or non-volatile memory, such as read only memory (ROM). The system memory 1012 may store data such as diffuser status data 1007 and/or program modules such as operating system 1005 and diffuser status display software 1006 that are accessible to and/or are operated on by the one or more processors 1003.

The computing device 1001 may also comprise other removable/non-removable, volatile/non-volatile computer storage media. The mass storage device 1004 may provide non-volatile storage of computer code, computer readable instructions, data structures, program modules, and other data for the computing device 1001. The mass storage device 1004 may be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EE-PROM), and the like.

Any number of program modules may be stored on the mass storage device 1004. An operating system 1005 and diffuser status display software 1006 may be stored on the mass storage device 1004. One or more of the operating system 1005 and diffuser status software 1006 (or some combination thereof) may comprise program modules and the diffuser status display software 1006. Diffuser status data 1007 may also be stored on the mass storage device 1004. Diffuser status data 1007 may be stored in any of one or more databases known in the art. The databases may be centralized or distributed across multiple locations within the network 1015.

A user may enter commands and information into the computing device 1001 via an input device (not shown). Such input devices comprise, but are not limited to, a keyboard, pointing device (e.g., a computer mouse, remote control), a microphone, a joystick, a scanner, tactile input devices such as gloves, and other body coverings, motion sensor, and the like. These and other input devices may be connected to the one or more processors 1003 via a human machine interface 1002 that is coupled to the bus 1013, but may be connected by other interface and bus structures, such as a parallel port, game port, an IEEE 1394 Port (also known as a Firewire port), a serial port, network adapter 1008, and/or a universal serial bus (USB).

A display device 1011 may also be connected to the bus 1013 via an interface, such as a display adapter 1009. It is contemplated that the computing device 1001 may have more than one display adapter 1009 and the computing device 1001 may have more than one display device 1011. A display device 1011 may be a monitor, an LCD (Liquid Crystal Display), light emitting diode (LED) display, television, smart lens, smart glass, and/or a projector. In addition to the display device 1011, other output peripheral devices may comprise components such as speakers (not shown) and a printer (not shown) which may be connected to the computing device 1001 via Input/Output Interface 1010. Any step and/or result of the methods may be output (or caused to be output) in any form to an output device. Such output may be any form of visual representation, including, but not limited to, textual, graphical, animation, audio, tactile, and the like. The display 1011 and computing device 1001 may be part of one device, or separate devices.

The computing device 1001 may operate in a networked environment using logical connections to one or more remote computing devices 1014*a,b,c*. A remote computing device 1014*a,b,c* may be a personal computer, computing station (e.g., workstation), portable computer (e.g., laptop, mobile phone, tablet device), smart device (e.g., smartphone, smart watch, activity tracker, smart apparel, smart accessory, or smart home hub), security and/or monitoring device, a server, a router, a network computer, a peer device, edge device or other common network node, and so on. Logical connections between the computing device 1001 and a remote computing device 1014*a,b,c* may be made via a network 1015, such as a local area network (LAN) and/or a general wide area network (WAN). Such network connections may be through a network adapter 1008. A network adapter 1008 may be implemented in both wired and wireless environments. Such networking environments are conventional and commonplace in dwellings, offices, enterprise-wide computer networks, intranets, and the Internet.

Application programs and other executable program components such as the operating system 1005 are shown herein as discrete blocks, although it is recognized that such programs and components may reside at various times in different storage components of the computing device 1001, and are executed by the one or more processors 1003 of the computing device 1001. An implementation of diffuser status display software 1006 may be stored on or sent across some form of computer readable media. Any of the disclosed methods may be performed by processor-executable instructions embodied on computer readable media.

In some embodiments, the computing device 1001 may be electronically connected to or include one or more imaging devices, for example a camera 1040 or depth sensor. For example, as further discussed herein, in some embodiments, the computing device 1001 can be a smartphone or tablet having the camera 1040 integrated therein.

Illuminating Panel

Figure 10:
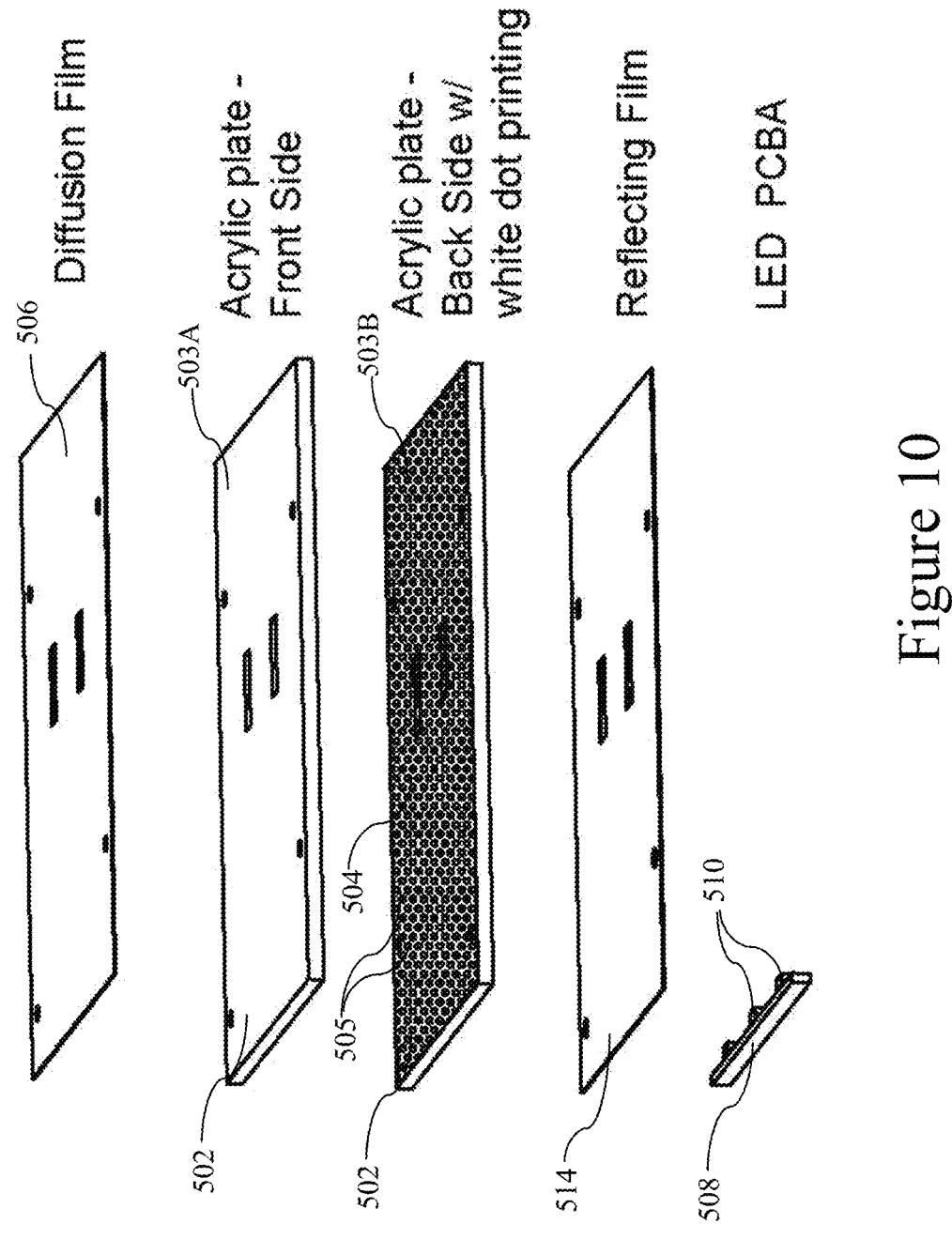
FIG. 10 is a perspective view of components of an illuminating plate in accordance with embodiments disclosed herein.
Figure 11:
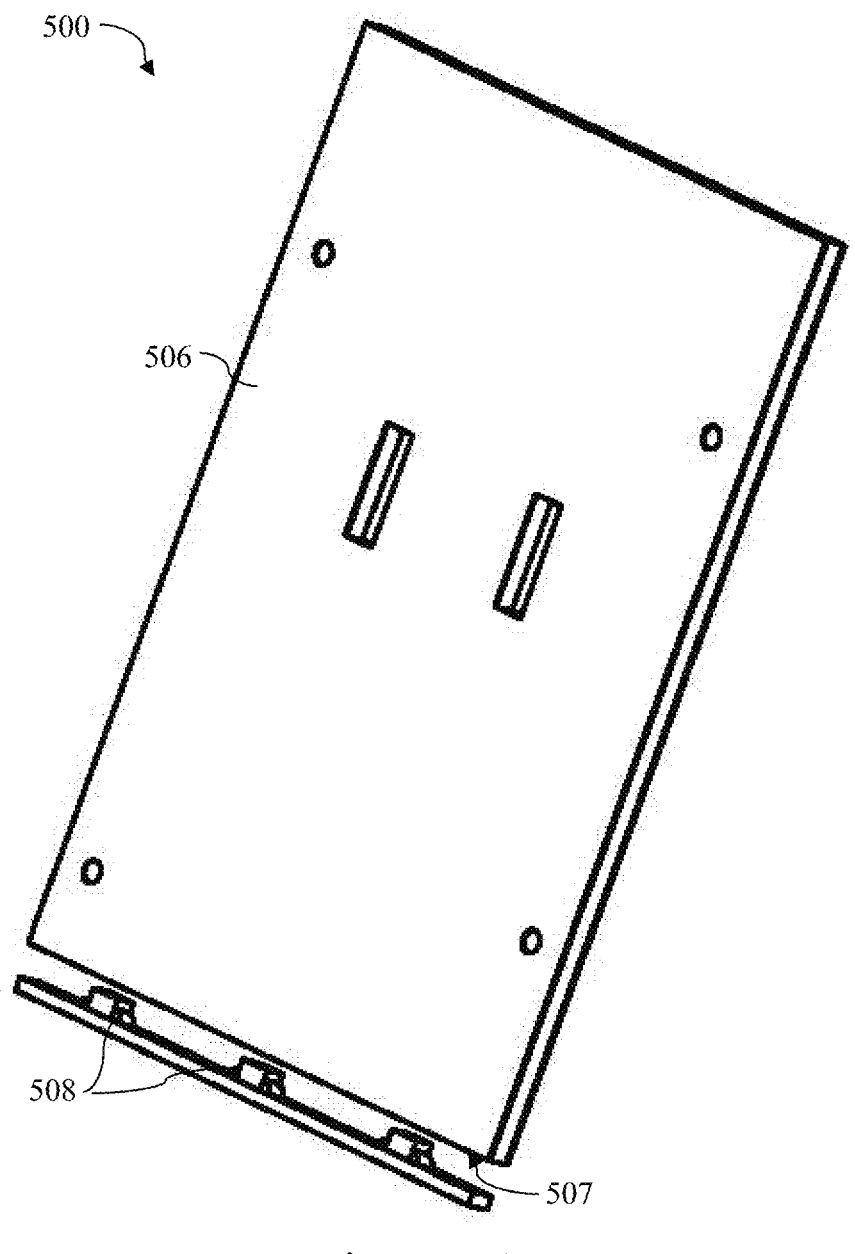
FIG. 11 is a perspective view of the illuminating plate of FIG. 10.
Figure 12:
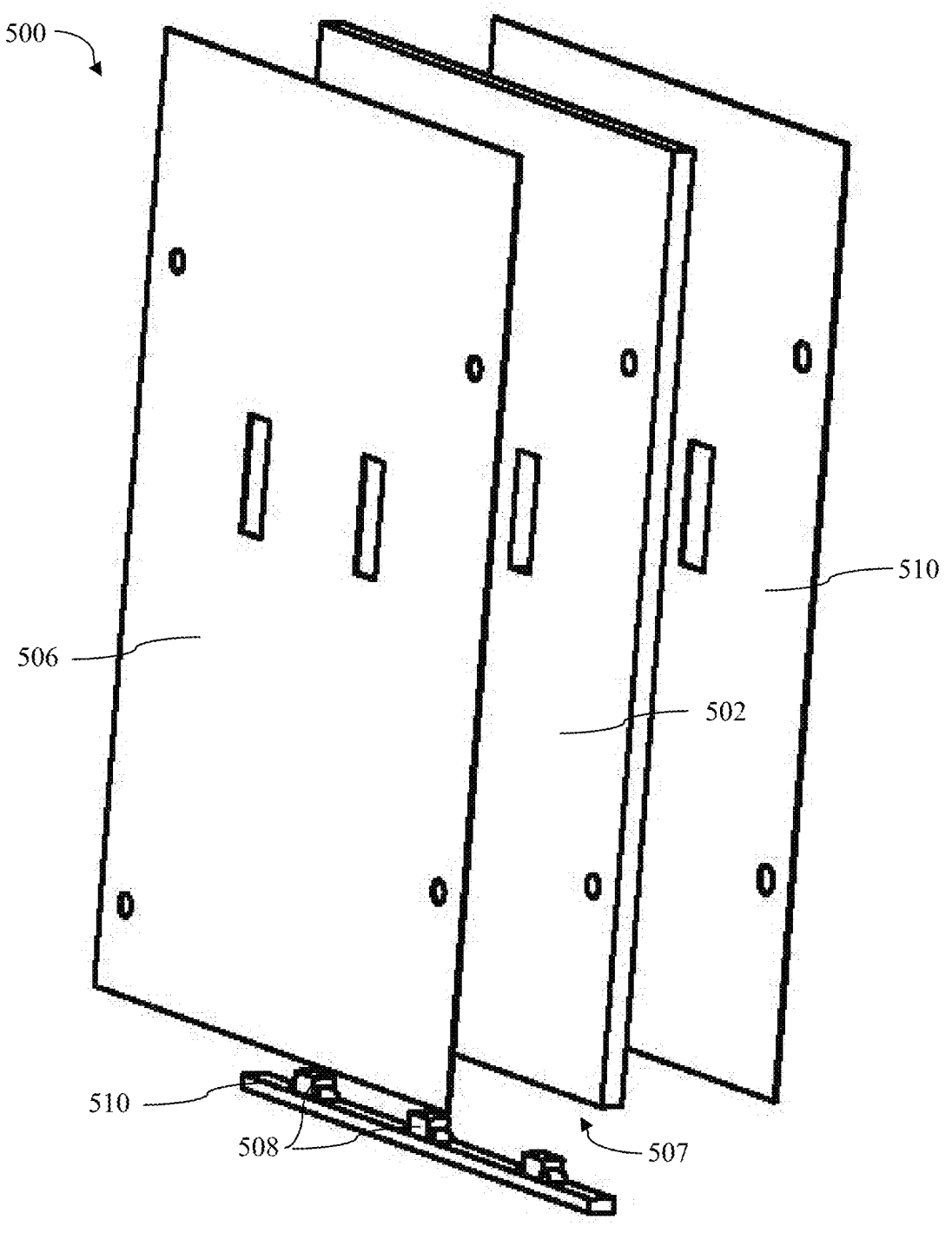
FIG. 12 is an exploded view of the illuminating plate of FIG. 10.

Referring to FIGS. 10-12, in some embodiments, the diffuser 10 (FIGS. 1-6 and 14) can comprise, or be coupled to, an illuminating panel 500. The illuminating panel 500 can be used to illuminate a pattern, shape, or object from behind the pattern, shape, or object. Conventional electroluminescent panels require high voltage alternating current. However, high voltage can limit attainability of UL certification. Accordingly, the illuminating panel 500 can be powered with low voltage lighting, such as, for example, LEDs as further disclosed herein.

As shown in FIG. 10, the illuminating panel 500 can comprise a (fully or partially) transparent plate 502 having a front side 503A and an opposed back side 503B. The transparent plate 502 can comprise, for example, glass or acrylic material(s). In some embodiments, the transparent plate 502 can be clear and 100% transparent. In further embodiments, the transparent plate can be colored. In still further embodiments, it is contemplated that the transparent plate 502 can be less than 100% transparent; however, it is further contemplated that substantially reduced transparency can reduce the illuminating aspects of the illuminating panel 500.

A reflective back surface 504 (e.g., a reflective plate, film, printed pattern, etc.) can attach to, or be positioned against, the back side 503B of the transparent plate 502. Optionally, the reflective back surface 504 can comprise a pattern of dots 505. "Dots," as used herein, should be understood to include areas of relatively high reflectivity intermixed with areas of comparatively low reflectivity. Optionally, some or all of the dots can be connected. The dots can have circular, rectangular, linear, hexagonal, or other suitable shapes. Optionally, the pattern of dots 505 can include a plurality of different shapes and/or a plurality of different sizes. The dots can optionally be white. The dots can be printed, or attached, to the back side 503B of the transparent plate 502 or printed/attached to a film or other layer that is attached or coupled to the back side of the transparent plate.

The dots 505 can cover a smaller surface area closer to the lighting (e.g., LEDs) and cover a larger surface area farther from the lighting (e.g., LEDs). For example, the dots can be larger and/or be more concentrated per given area in locations close to the lighting (e.g., LEDs) and can be smaller and/or be less concentrated per given area in locations farther from the lighting (e.g., LEDs). Optionally, the pattern of dots can include a progressive change (increase or decrease) in surface area coverage at a gradient in order to provide a consistent illumination intensity across the surface of the illuminating panel 500. For example, as shown in FIGS. 11-12, in an embodiment in which the illuminating panel 500 has a single illuminated edge 507, the dots 505 can cover a larger area at the end of the illuminating panel opposite the illuminated edge. In an embodiment having two opposing illuminated edges, the dots can cover a relatively larger area at the middle of the illuminating panel than near the two illuminated edges.

Optionally, as shown in FIG. 10, a second reflective surface 514 (e.g., a reflective film or a white film) can be positioned against the back surface of the transparent plate, behind the reflective back surface 504.

A diffusion film 506 or plate can attach to, or be positioned in front of, the front side of the transparent plate. One or more LEDs 508 or other suitable lights can illuminate one or more edges of the transparent plate. For example, an LED assembly 510 can attach to the illuminating panel 500. In exemplary aspects the LED assembly 510 can comprise a support bar and one or more LED receptacles that support the one or more LEDs 508. Optionally, the support bar can attach at an edge of the transparent plate 502 via an adhesive or via heat bonding. In further embodiments, the LED assembly 510 can be attached to a plate support structure.

Figure 14:
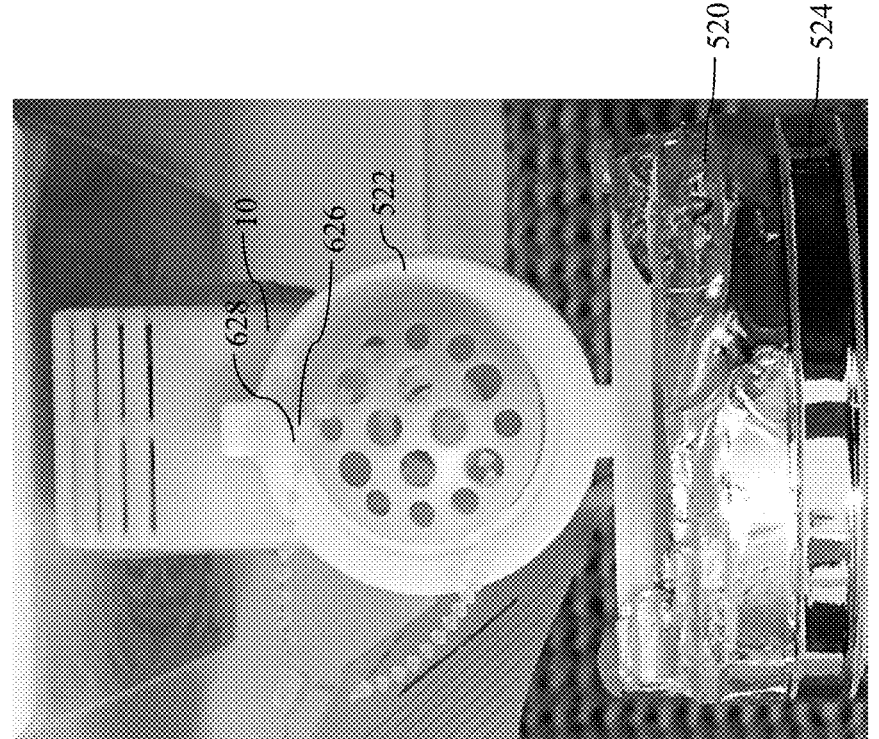
FIG. 14 is a top view of a diffuser having a display assembly attached thereto.
Figure 13:
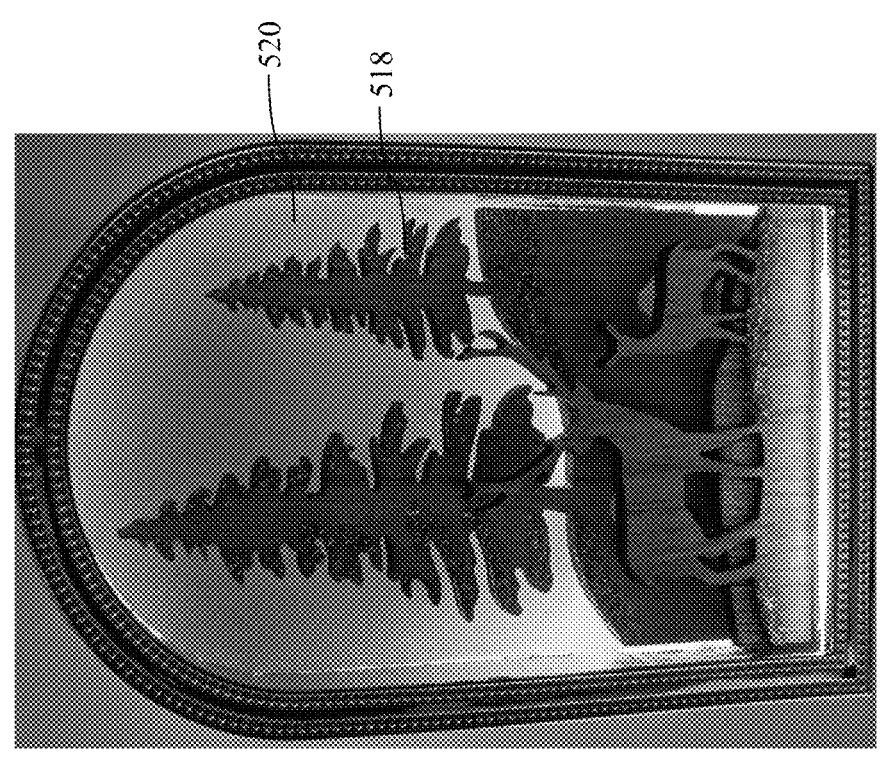
FIG. 13 is a front view of a display assembly that comprises an illuminating plate as in FIG. 10.
Figures 15, 16, 17:
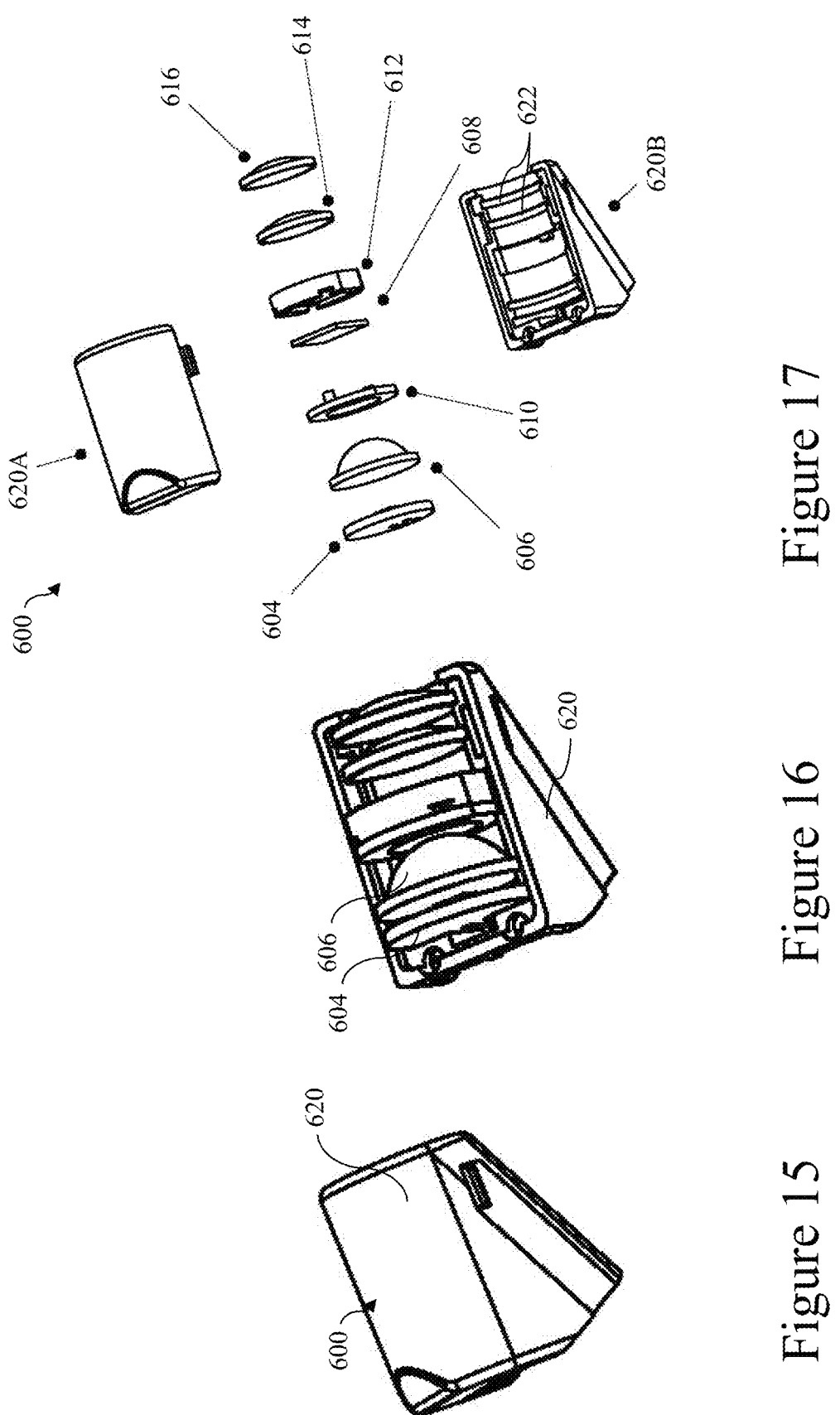
FIG. 15 is a top perspective view of a projector in accordance with embodiments disclosed herein.
FIG. 16 is a top perspective view of the projector of FIG. 15 with the upper case portion removed.
FIG. 17 is an exploded view of the projector of FIG. 15.
Figure 18:
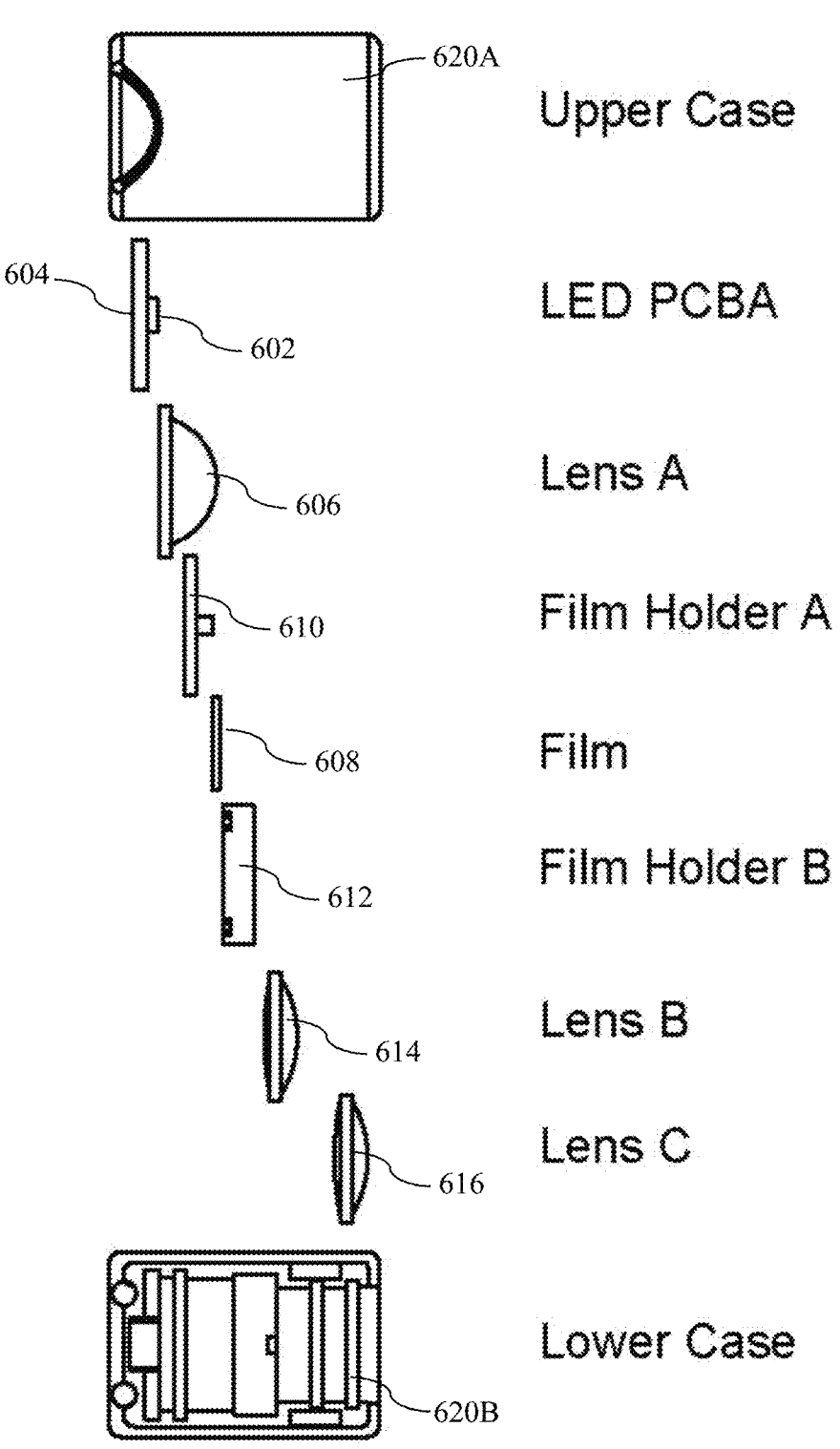
FIG. 18 is a perspective view of components of the projector of FIG. 15.
Figure 20:
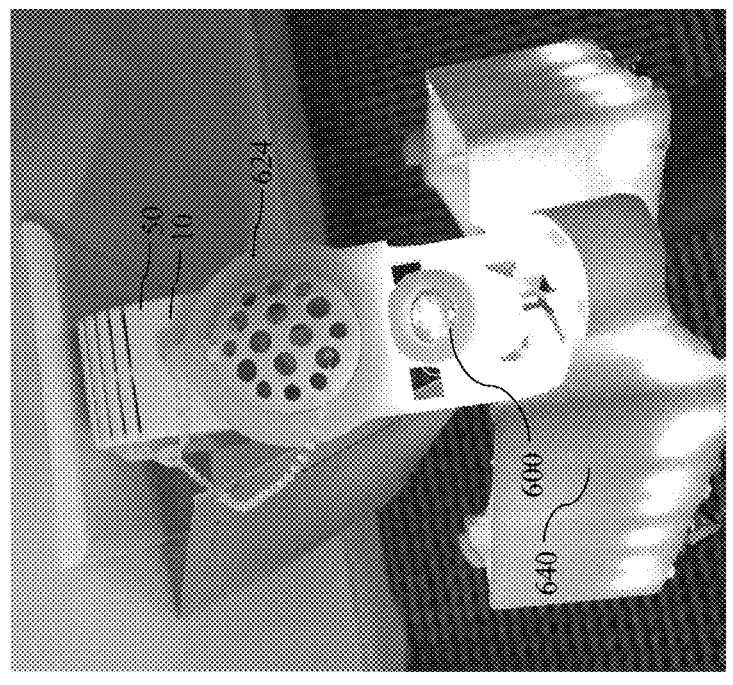
FIG. 20 is a top view of the diffuser as in FIG. 19.

Referring also to FIGS. 13-14, a pattern 518 can be positioned in front of the illuminating panel 500. In further embodiments, the pattern 518 can be applied to the front side of plate 502, applied to the front of the diffusion film 506, or applied to a separate film. The pattern 518 can comprise various elements, such as, for example, opaque portions, colored portions, transparent portions, translucent portions, cutouts that expose the illuminating panel 500, and combinations thereof. Optionally, the pattern can produce a desired artistic effect. For example, as shown in FIG. 13, the pattern can define a nature scene. Optionally, the pattern can be a three-dimensional pattern that is housed within an outer frame 524. Optionally, the outer frame can include a transparent cover that overlies the pattern and is in opposing relationship to the illuminating panel 500.

In some embodiments, a display assembly 520 can comprise an illuminating panel 500 and a pattern. The display assembly 520 can couple to the diffuser 10 via a collar 522 that extends around a portion of the diffuser. Optionally, the collar 522 can include at least one arm that is secured or attached to a rear plate that encloses the illuminating panel 500 within the frame. Electrical wires can extend from the dispenser, through the collar, and into the display assembly 520 to power the LEDs. Alternatively, it is contemplated that a power source can be positioned within the frame and electrically connected to the LEDs.

Projector

Referring to FIGS. 15-24, in some embodiments, the diffuser 10 can comprise, or be coupled to, a projector 600. Optionally, it is contemplated that the diffuser 10 can include both the projector 600 and an illuminating panel 500 (and display assembly 520) as disclosed herein. The projector 600 can project an illuminated image 630 (FIG. 19) against a surface near the diffuser 10, such as, for example, a portion of a wall near an electrical outlet into which the diffuser 10 is plugged.

The projector 600 can comprise a light source 602 (e.g., an LED) attached to a PCB 604. The light source can project through a collimating lens 606 to provide light rays extending parallel to each other. The light from the collimating lens 606 can pass through a film 608. The film can comprise a print of a negative distorted image. The film 608 can be encased in a lower housing film holder 610 and an upper housing film holder 612. The film 608 can be positioned between the collimating lens 606 and a focusing lens 614. From the focusing lens 614, the light can project through an expansion lens 616. The light from the expansion lens 616 can project on the projection surface, such as, for example, the portion of the wall near the outlet.

Each of the PCB 604, collimating lens 606, film 608, upper and lower film holders 610, 612, focusing lens 614 and expansion lens 616 (collectively, the optical components) can be positioned within a housing 620. The housing can comprise a top portion 620A and a bottom portion 620B. The housing 620 can define receptacles 622 that are configured to receive the optical components, thereby spacing the optical components in their respective optimal positions to project a clear, undistorted, positive image of the image printed on the projection surface. The housing 620 can comprise, or attach to, a collar 624 that can encircle or otherwise complementarily engage at least a portion of the diffuser housing 50 to thereby couple to the diffuser housing. For example, the circumference of the dome shaped cover 68 (FIG. 1) can be encircled by, and engage, the collar 624 via a slip fit or an interference fit. Optionally, an adhesive or heat bond can couple the collar to the diffuser housing. Optionally, the dome shaped cover 68 can comprise a key 626 is receivable into a notch 628 in the collar to thereby rotationally lock the collar to the diffuser housing.

In some embodiments, the housing can be configured for emitting a projection at an angle with respect to the horizontal. In this way, the projection surface can be above or below the diffuser 10. In further embodiments, the projection surface can be to the side of the diffuser 10 (i.e., off to the side of a vertical plane that bisects the diffuser 10). Thus, the optical components, including the lenses and film, can comprise distortions that are undistorted when projected at an angle against the projection surface.

Optionally, the diffuser 10 can further comprise an ornament 640. The ornament 640 can optionally attach to the collar 624 to thereby couple the ornament to the diffuser housing. For example, it is contemplated that the collar 624 can define at least one arm that is configured to engage a complementary portion (e.g., a projection) of a rear portion of the ornament 640. Optionally, it is contemplated that the collar 624 can define opposing arms that define respective openings that are configured to receive complementary projections defined by the rear portion of the ornament. The ornament 640 can comprise lights (e.g., LEDs) that are configured to illuminate at least portions of the ornament (e.g., through translucent portions of the ornament) or emit light from the ornament (e.g., through transparent portions of the ornament).

In some optional embodiments, the ornament 640 can comprise an on-board circuit. The on-board circuit can be configured to control lighting effects, sound, timers, etc. In some embodiments, the on-board circuit can comprise a processor that is configured to control said lighting effects, sound, timers, etc. According to some aspects, the processor of the on-board circuit can be in communication with one of the controller 100, the controller 402, or the computing device 1001. In this way, the control of the ornament 640 can be controlled remotely and be coordinated with other aspects of the diffuser 10. For example, the diffuser can be configured to dispense a fragrance upon sensing an individual in a room, and the ornament can be illuminated only when the diffuser is dispensing fragrance.

Figure 19:
FIG. 19 is a top perspective view of a diffuser having a projector and an ornament attached thereto.
Figure 22:
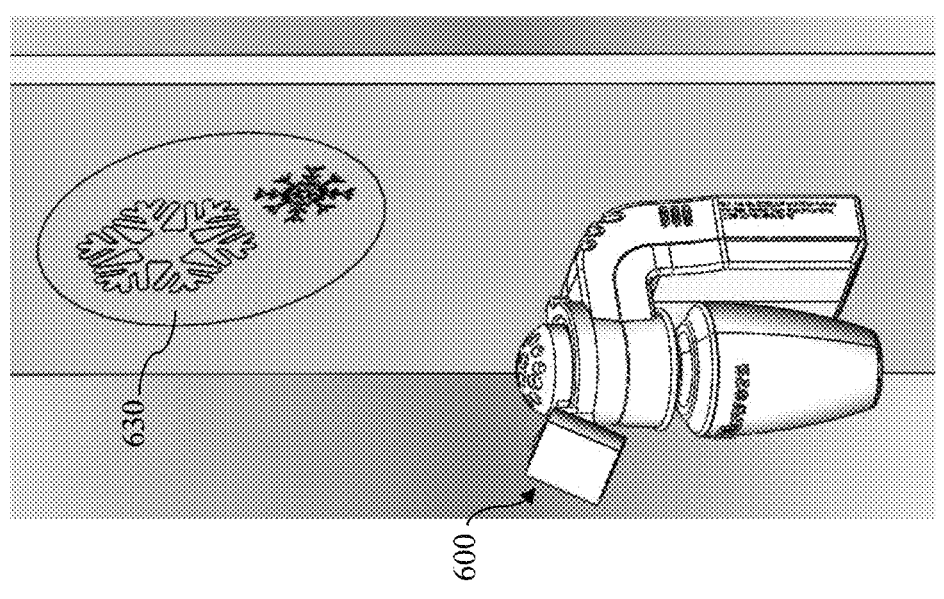
FIG. 22 is an assembled view of the embodiment of FIG. 21.
Figure 21:
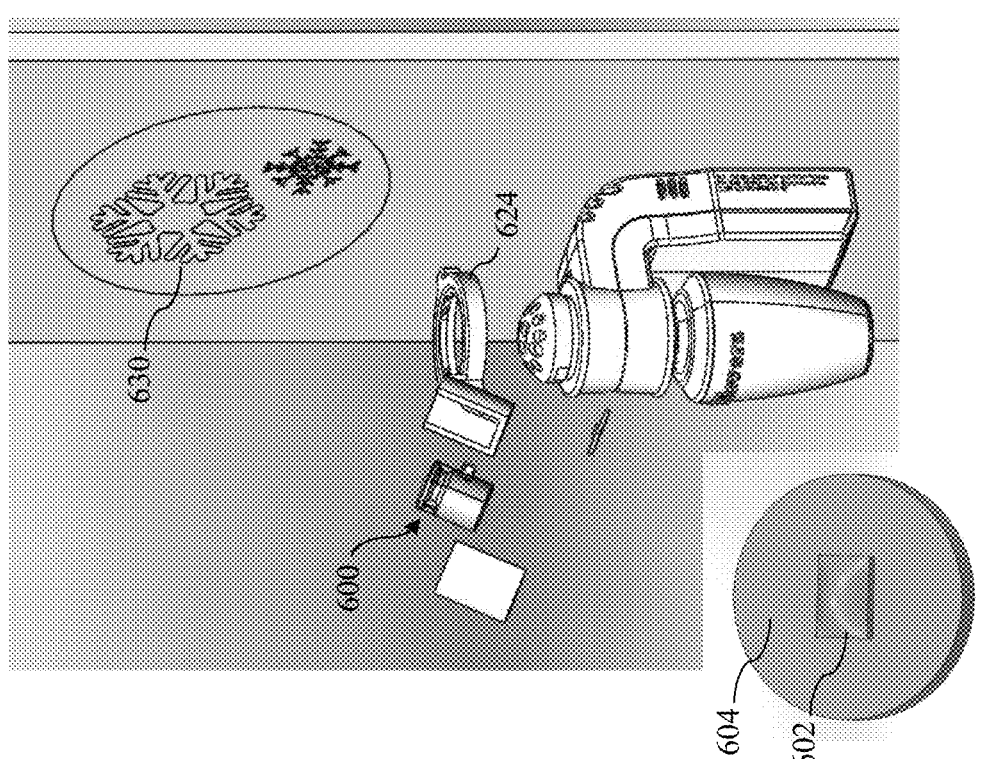
FIG. 21 is an exploded view of an embodiment of a diffusing having a projector thereon.
Figure 24:
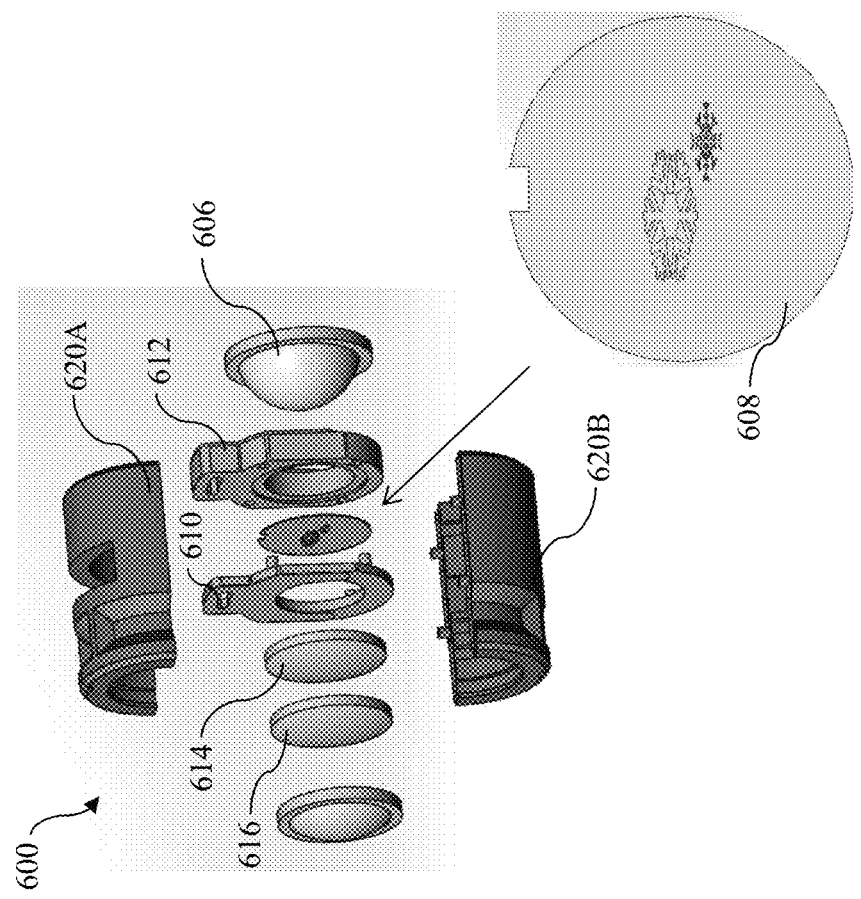
FIG. 24 is an exploded view of the projector of FIG. 21, further showing film of the projector.
Figure 23:
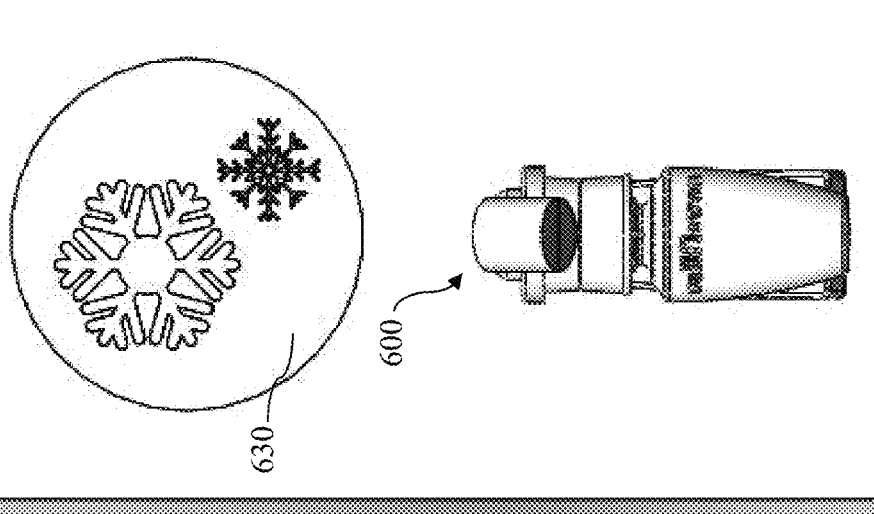
FIG. 23 is a front view of the embodiment of FIG. 22.
Figures 25A, 25B, 25C, 25D:
FIG. 25A is a top view of a diffuser having a glow cuff.
FIG. 25B is the top view of the diffuser as in FIG. 25A with a ruler as a size reference.
FIG. 25C is an underside view of the diffuser as in FIG. 25A.
FIG. 25D is a side view of the diffuser as in FIG. 25A.
Figures 26, 27:
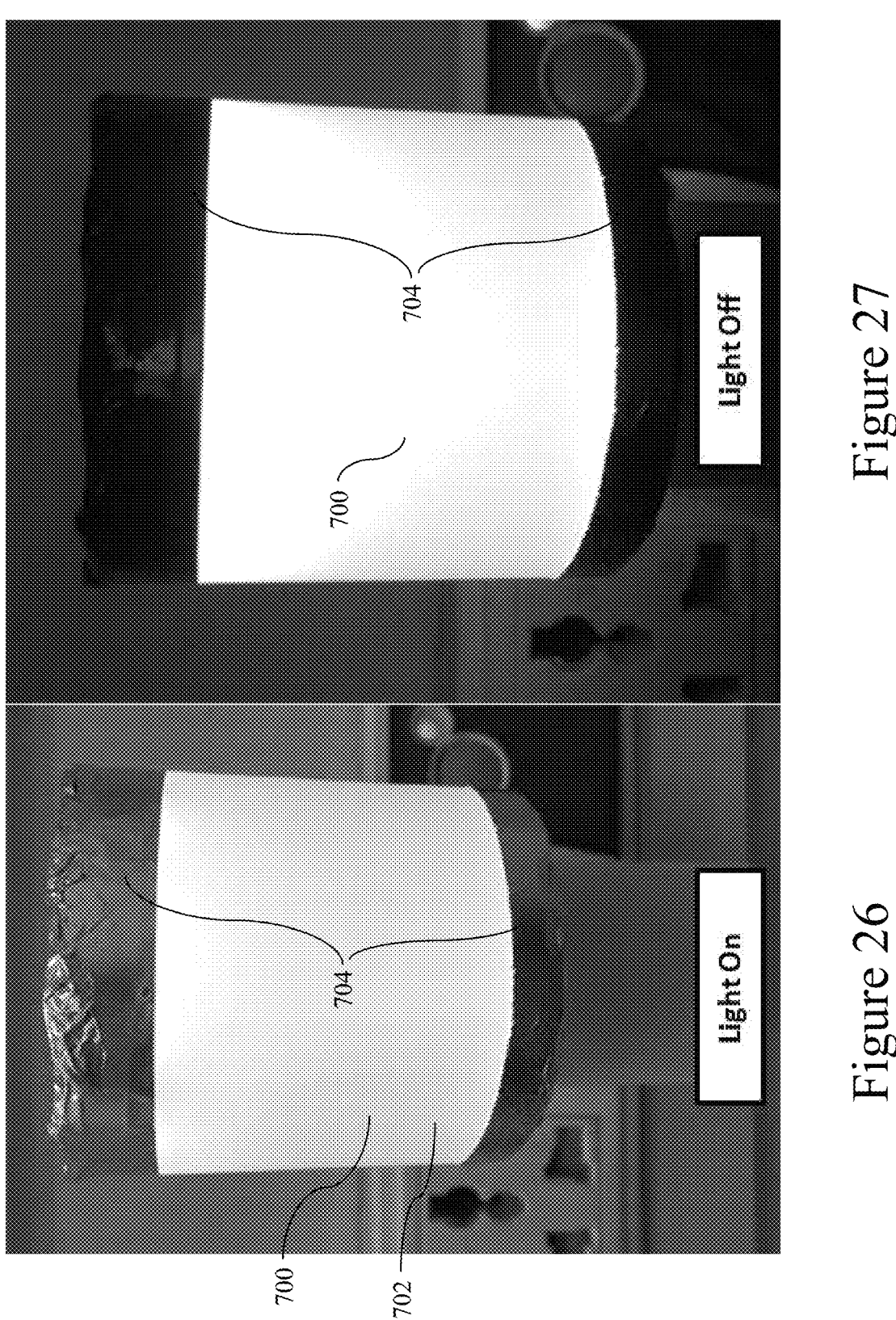
FIG. 26 is a front view of a diffuser with a glow cuff.
FIG. 27 is another front view of the diffuser of FIG. 26 without the cuff being illuminated.

Optionally, the ornament 640 and the image 630 can have a consistent theme and thereby cooperate to define a display 650. For example, as shown in FIG. 19, the ornament 640 and the image 630 can provide visual representations that are associated with a single holiday theme (such as an ornament with a snowman and a house decorated for Christmas and an image depicting Santa Claus on a sleigh being pulled by his reindeer).

Figure 34:
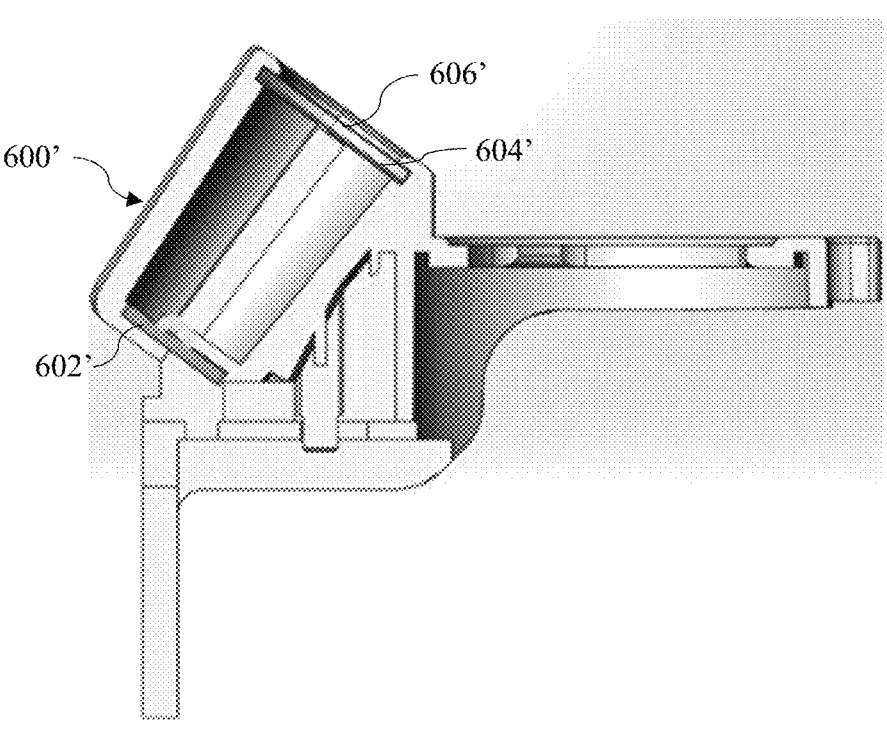
FIG. 34 is a cross sectional view of a diffuser having a projector, in accordance with the present disclosure.
Figure 35:
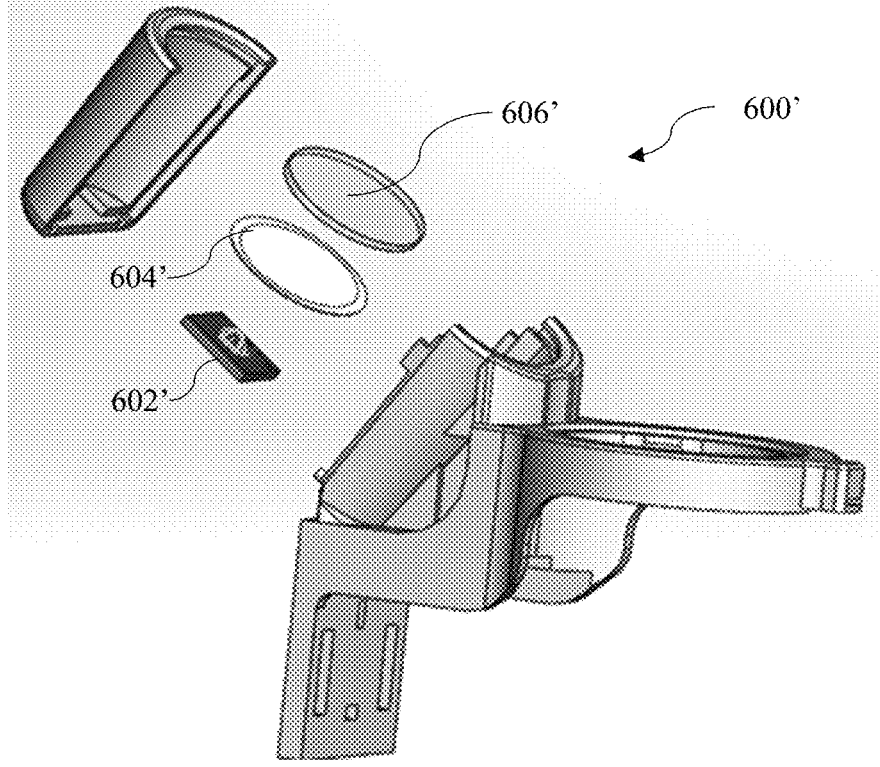
FIG. 35 is an exploded view of the diffuser of FIG. 34.
Figure 36:
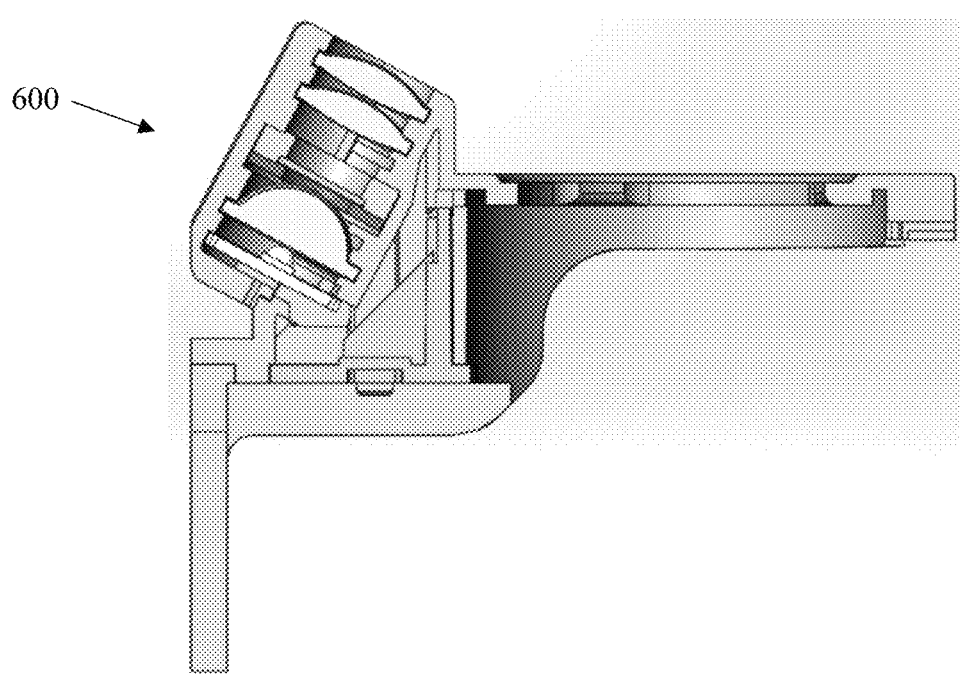
FIG. 36 is a cross section of a diffuser having another projector, in accordance with the present disclosure.
Figure 37:
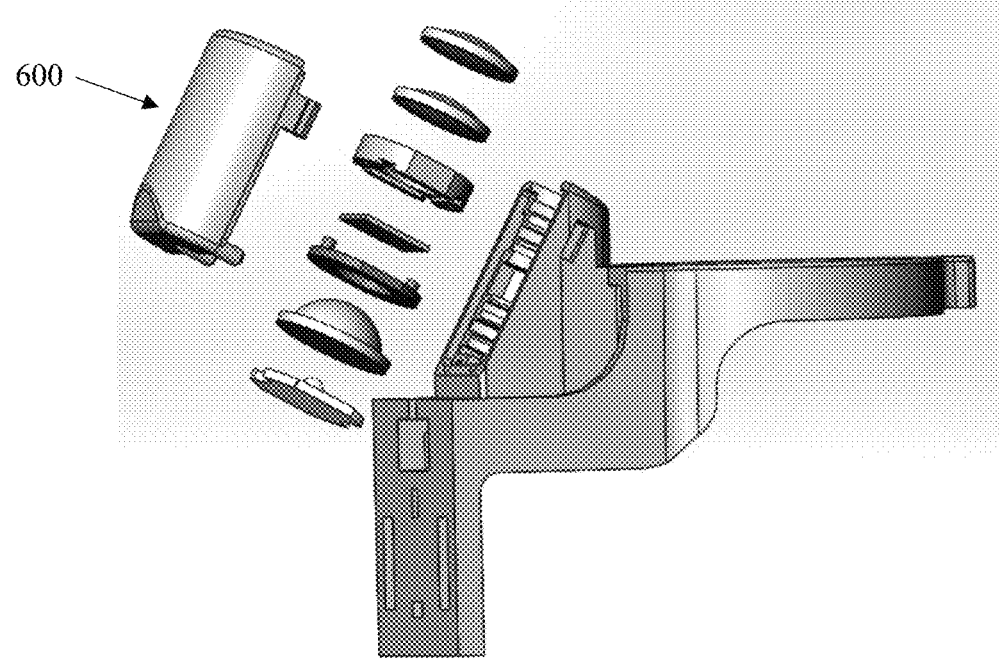
FIG. 37 is an exploded view of the diffuser of FIG. 36.

Referring to FIGS. 34-35, in further aspects, a projector 600' can comprise a light source 602', a film 604', and a lens 606' (optionally, a single lens). The projector can be configured to output an image or pattern based on the image or pattern on the film. The pattern can optionally be, for example, a butterfly, a rainbow, a wave, or an abstract pattern. In some optional aspects, the projector 600' can desirably project an image or pattern having blurred edges. In some aspects, the film can have a colored pattern, and the projector 600' can project a colored pattern based on the colored pattern of the film. The light source 602' can be a white or colored light source, such as, for example, a white, red, green, or blue LED, or combinations thereof. Optionally, the pattern can be a translucent pattern, an opaque pattern, or a combination thereof. Optionally, the film can comprise a textured pattern (e.g., a wavy pattern) that can optionally be provided in an aluminum tool. In further optional aspects, the pattern can be a blue pattern (e.g., a blue butterfly), and the light source can be a blue light (e.g., a blue LED). In still further optional aspects, the pattern can be a purple pattern (e.g., a purple butterfly), and the light source can comprise a blue light and a green light (e.g., a blue LED and a green LED).

Illuminated Cuff

Referring to FIGS. 25A-29, in some embodiments, the diffuser 10 can comprise an illuminated cuff 700. As disclosed herein, an "illuminated cuff" should be understood to be a cuff that is configured to be illuminated, rather than a cuff that is necessarily illuminated at any given time. Thus, a diffuser can have an "illuminated cuff" even when the lights therein are not presently powered. The cuff can optionally comprise one or more sheets of material 702 that extend around at least a portion of the circumference of the diffuser housing 50 (FIG. 1). Optionally, the cuff can at least partially surround the portion of the diffuser housing including the socket portion 51 and the dome shaped cover 68. In further embodiments, shown in FIGS. 28 and 29, the cuff can surround at least a portion of the fragrance bottle 60. The cuff can have cylindrical or otherwise curved surface. The cuff 700 can define an interior and comprise one or more lights within the interior. The one or more sheets of material 702 can comprise a transparent or translucent material that can be illuminated by the lights within the interior. In further embodiments, the cuff 700 can have one or more lights positioned at the upper and/or lower rim of the cuff 700. Optionally, the cuff 700 can have a plurality of lights spaced around the circumference of the upper rim of the cuff 700 and a plurality of lights spaced around the circumference of the lower rim of the cuff 700. In this way, light can travel through the cuff material, between an inner and outer surface of the cuff 700. The light can be partially internally reflected and partially transmitted at the boundary between the outer surface and the surrounding air.

In exemplary aspects, the cuff 700, apart from its shape, can have a structure that is consistent with the illuminated panel 500 as disclosed above. For example, the cuff can have a curved transparent plate having an inner surface and an outer surface. A first reflective surface can be applied to (e.g., printed on or positioned against) the inner surface of the curved transparent plate. The first reflective surface can comprise a pattern of dots that can have features corresponding to or similar to that of the reflective back surface 504 of the illuminating panel 500, disclosed herein. For example, the pattern of dots can cover a smaller surface area closer to the plurality of lights (e.g., LEDs) and cover a larger surface area farther from the plurality of lights (e.g., LEDs). In some aspects, the dots can be larger and/or be more concentrated per given area in locations close to the lighting (e.g., LEDs) and can be smaller and/or be less concentrated per given area in locations farther from the lighting (e.g., LEDs). A second reflective surface (e.g., a reflective film) can be positioned behind the first reflective back surface. The outer surface of the curved plate can have a diffusion film. In further aspects, the outer surface of the curved transparent plate can have a frosted texture or a diffusion coating to provide a surface that diffuses the light as it is emitted therefrom.

Optionally, upper and/or lower edges of the cuff 700 can be covered with a rim cover 704 comprising a reflective or opaque material. The rim cover(s) 704 can optionally cover the lights positioned at the rims to block light emitted directly therefrom and direct the light into the material of the cuff 700. The rim cover 704 can optionally have an aesthetic pattern, such as a wavy profile.

Figure 29:
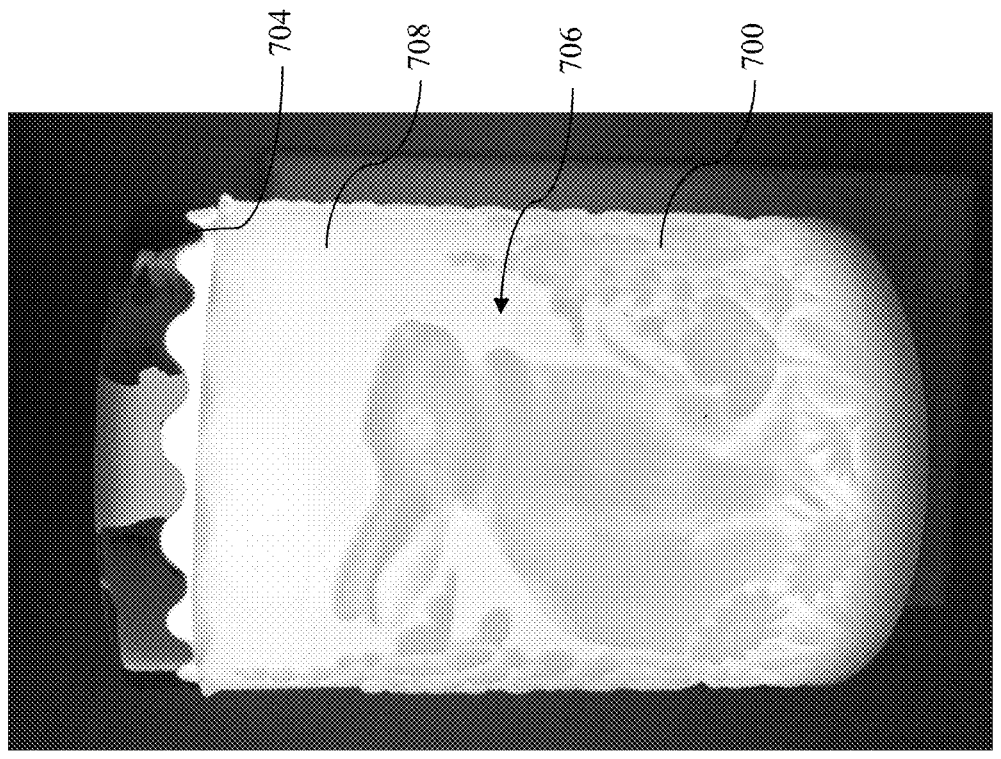
FIG. 29 is a perspective view of a diffuser having a glow cuff and a pattern thereon.
Figure 28:
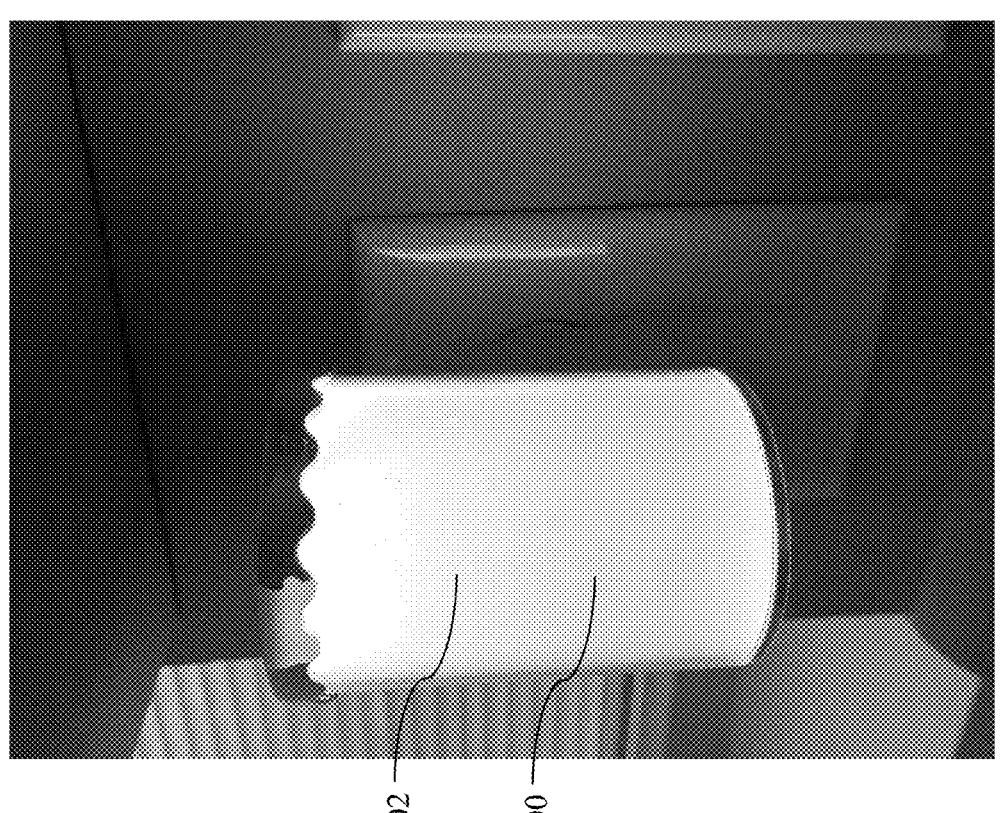
FIG. 28 is a perspective view of a diffuser having another glow cuff.

As shown in FIG. 29, the cuff 700 can further define a pattern 706 that produces a desired visual effect when illuminated. In some aspects, the pattern 706 is on the one or more sheets of material 702. In further aspects, the pattern 706 is on a second material 708 that surrounds the one or more sheets of material 702. The second material 708 can optionally be transparent or translucent. In some aspects, the pattern 706 can be defined by a contour on one of the cover and the second material 708. Optionally, the pattern can form an artistic scene, such as a nature scene as shown in FIG. 29. However, it is contemplated that the pattern can provide any desired visual representation or effect, including those having letters, numbers, words, color patterns, artistic scenes (including characters, animals, places, nature scenes, buildings, and the like), and combinations thereof.

Control of the Illuminating Panel, Projector, and Illuminated Cuff

As disclosed herein, according to various embodiments, each of the illuminating panel 500, projector 600, and cuff 700 can be remotely controlled via an on-board controller or a remote controller. For example, in some embodiments, the light source (e.g., LEDs 510 and light source 602) can be controlled to, for example, turn on/off, change color, or vary intensity. The light source can be controlled according to various conditions, such as, for example, when the diffuser detects the presence of an individual in a room, at a programmed time of day, when the diffuser receives a user input via smartphone, when the diffuser heater is turned on, or any other conditions as disclosed herein or apparent to one skilled in the art.

Optionally, in some aspects, the illuminating panel 500, the projector 600, and/or the illuminated cuff 700 can be electrically or communicatively coupled to a controller 100 and/or a controller 402 as further disclosed herein. In some embodiments, the controller 100 can simultaneously modulate the pulse width to the heater and the LEDs 508 so that the intensity of the illuminating panel 500 can vary with the output of the diffuser 10. Optionally, the heater and the LEDs can be connected in series so that modulation of power to the heater correspondingly modulates power to the LEDs, thereby varying the intensity of the illuminating panel with the intensity of the fragrance output. Similarly, in some embodiments, the controller 100 can simultaneously modulate the pulse width to the heater and lights in the interior of the illuminated cuff so that the intensity of the illuminated cuff 700 can vary with the output of the diffuser 10. In some embodiments, the illuminated cuff 700 and heater can be connected in series. In still further embodiments, at least one of the illuminating panel 500, the projector 600, and the illuminated cuff 700 can turn on or off or change color/intensity based on the duty cycle of the PWM signal passing a threshold. In still further embodiments, the lights of the projector 600 and/or the ornament 640 can change with the PWM duty cycle of the heater. For example, if the duty cycle is above 50%, the lights of the illuminating panel 500, the projector 600, and/or the illuminated cuff 700 can be illuminated, and below 50%, the lights can be off. In still further embodiments, at least one of the illuminating panel 500, the projector 600, and the illuminated cuff 700 can change in response to the sensed level of the liquid 62 (FIG. 1). For example, the lights of the illuminating panel 500, the projector 600, and/or the illuminated cuff 700 can change color, intensity, or turn on/off in response to the liquid 62 level passing a threshold.

Dynamic Fragrance Control

Conventional fragrance diffusers have a constant heat setting, which is typically defined by the manufacturer. It has been found that, for constant heat settings, individuals notice the fragrance less and less over time. These constant heat settings produce continuous fragrance dispersion rates, which can cause anosmia, whereby the individuals stop noticing the fragrance as their senses adjust to the scent. Disclosed herein are fragrance diffusers that are configured to provide a fragrance output that remains noticeable at a desired level over time.

Figure 30:
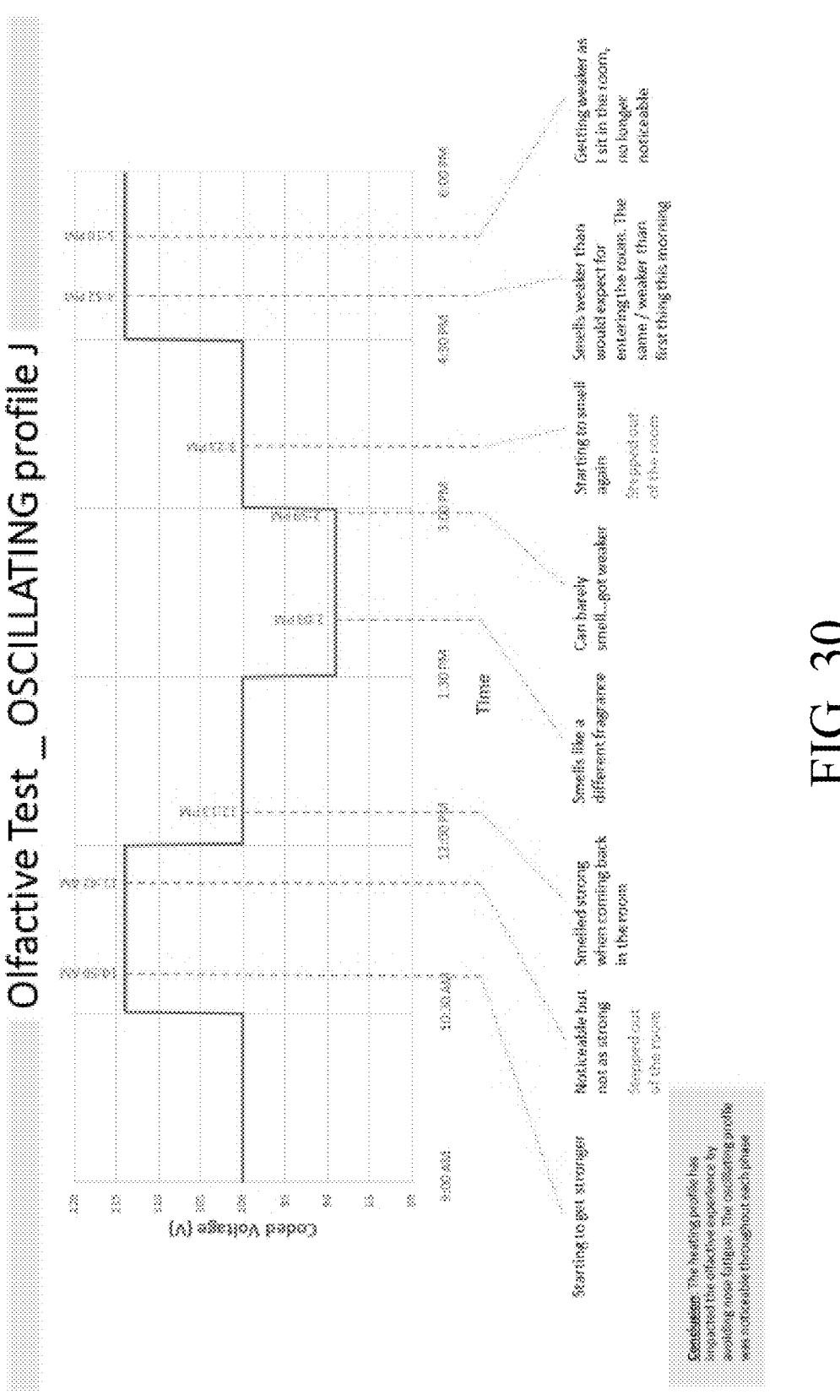
FIG. 30 is a plot showing results of a test for noticing a fragrance output for a diffuser employing an exemplary variable output sequence as disclosed herein.

Referring to FIGS. 1, 6, and 30, in some aspects, the controller 100 of the dispenser 10 can be configured to vary the power output of the heater in accordance with a heat profile. The heat profile can comprise a plurality of power outputs of the heater, corresponding with different fragrance dispersion rates. In this way, it is contemplated that individuals in the vicinity of the dispenser can continue to notice and appreciate the fragrance. FIG. 30 illustrates an olfactive test indicating that sustained fragrance can cause a lesser fragrance detection, whereas a varied fragrance dispersion rate can enable an individual to continue to notice the fragrance throughout the duration of use.

In some aspects, the heat profile can comprise a first power output, a second power output that is greater than the first power output, and a third power output that is greater than the first and second power outputs. Although disclosed herein as "first," "second," and "third" power outputs, it is understood that these terms do not require a particular order of power outputs; rather, these terms are meant to indicate temporally distinct power outputs. It is contemplated that the heat profile can comprise any number of power outputs. For example, it is contemplated that the heat profile can comprise 4, 5, 6, 7, 8, 9, 10, 11, 12, 13, 14, 15, 16, 17, 18, 19, 20, or up to 134 power outputs. In exemplary aspects, the number of power outputs can range from about 2 to about 20 or from about 3 to about 10. In further exemplary aspects, it is contemplated that the heat profile can have at least 2, at least 3, or at least 4 power outputs that are different from one another.

Each of the first, second, and third power outputs can be sustained for a duration ranging from 73 minutes to one week. In further aspects, each of the first, second, and third power outputs can be sustained for a duration ranging from 75 minutes to twelve hours. In still further aspects, each of the first, second, and third power outputs can be sustained for a duration ranging from 90 minutes to four hours. In some aspects, each of the first, second, and third power outputs can be sustained for equal durations. In some aspects, the equal duration can be ninety minutes. In further aspects, it is contemplated that the duration of at least two of the power outputs can be different. It is contemplated that, for any number of different power outputs, the duration of each power output of the different power outputs can be the same as, or different from, any or all of the other power outputs.

In some aspects, the heat profile can include a pattern sequence. In some aspects, the pattern sequence can be repeated. For example, in one optional embodiment, a first pattern sequence can be the second power output, the third power output, the second power output, and the first power output. The first pattern sequence can optionally be repeated. In another optional embodiment, a second pattern sequence can comprise the third power output, the second power output, the first power output, and the second power output. The second pattern sequence can optionally be repeated. In another embodiment, a third pattern sequence can be the first power output followed by the third power output, and the third pattern sequence can optionally repeat. In another embodiment, a fourth pattern sequence can be the third power output, the second power output, and then the first power output, and the fourth pattern sequence can optionally repeat. In another embodiment, a fifth pattern sequence can be the first power output followed by the second power output, and the fifth pattern sequence can optionally repeat. In another embodiment, a sixth pattern sequence can be the first power output, the second power output, and then the third power output, and the sixth pattern sequence can optionally repeat. In various aspects, it is contemplated that the pattern sequence can be selectively modified by a user to make use of any number of different power outputs. More generally, it is contemplated that the pattern sequence can comprise, starting from an initial power output, a sequence of an increased power output followed by a decreased power output (with repeats producing an up and down pattern).

Similarly, it is contemplated that the pattern sequence can comprise, starting from an initial power output, a sequence of a decreased power output followed by an increased power output (with repeats producing a down and up pattern).

One exemplary heat profile is reflected in FIG. 30, which explains the impact of the voltage/power output on the user's experience with the fragrance provided by the diffuser. As shown, the initial power output was an intermediate level (like the second power output described herein). After the initial duration of the intermediate power output, the voltage shifted to a high power output (like the third power output described herein). This change in intensity was readily perceived by the user. Toward the end of the duration of the high power output, the scent was less noticeable, and the user left the room. While the user was away from the room, the diffuser transitioned back to the intermediate power output. When the user returned to the room, the fragrance was strong and easily detectable. At the end of this power output, the diffuser transitioned to a low power output (like the third power output described herein). At this point, the user indicated that the fragrance seemed to change, and the fragrance got progressively weaker during the duration of the low power output. However, as the diffuser transitioned to the intermediate power output, the fragrance became noticeable again. At this point, the user left the room. While the user was out of the room, the diffuser transitioned to the high power output. When the user returned, the fragrance was noticeable, but became less noticeable throughout the duration of the high power output. Overall, this heat profile revealed an ability of a diffuser as disclosed herein to avoid anosmia through changes in the power output.

In some aspects, the heat profile can have an inactive cycle during which the controller provides a minimum value of voltage to the heater. For example, the minimum value can be zero. In further aspects, the minimum value of voltage can be nonzero (for example, less than one volt or less than five volts).

Optionally, in some aspects, and as further disclosed herein, the controller can be configured to vary the power output of the heater by delivering a pulse-width-modulated electrical voltage to the heater. The first power output can be caused by delivering to the heater the pulse-width-modulated voltage having a first duty cycle. The second power output can be caused by delivering to the heater the pulse-width-modulated voltage having a second duty cycle that is greater than the first duty cycle. The third power output can be caused by delivering to the heater the pulse-width-modulated voltage having a third duty cycle that is greater than the first duty cycle and the second duty cycle.

In some optional aspects, the first power output can range from about 1 W to about 2.5 W or from about 1.5 W to about 2.0 W. Optionally, the second power output can range from about 1.4 W to about 3.0 W or from about 2.0 W to about 2.4 W. Optionally, the third power output can range from about 2.0 W to about 3.5 W or from about 2.4 W to about 3.0 W. For embodiments for which the power output of the heater is caused by delivering to the heater a pulse-width-modulated electrical voltage, optionally, the first duty cycle can range from about 5% to about 60% or from about 10% to about 40%, the second duty cycle can range from about 20% to about 90% or from about 35% to about 75%, and the third duty cycle can range from about 50% to about 100% or from about 70% to about 100%.

In further optional aspects, the power to the heater can generally be varied via analog control (as opposed to using pulse-width-modulated control). For example, it is contemplated that the power output of the heater can be selected or modified by selecting the voltage provided to the heater, wherein each power output corresponds to a different select, constant voltage. For example, the controller (e.g., an analog controller) can cause a first voltage to be applied to the heater to provide the first power output of the heater; the controller can cause a second voltage to be applied to the heater to provide the second power output of the heater; and the controller can cause a third voltage to be applied to the heater to provide the third power output of the heater. In further aspects, the controller can provide a select current across the heater to provide the select first, second, and third power outputs.

In still further optional aspects, other characteristics of the diffuser can be adjusted to vary diffusion rate, such as physical changes. For example, optionally, a number or size of holes through which the fragrance can diffuse can be varied. For example, some or all of the holes can be selectively opened and closed (e.g., blocked) or have an adjustable orifice size. As another optional example, the spacing between the wick and the heater can be varied to adjust the diffusion rate. Optionally, in exemplary aspects, it is contemplated that the controller can be configured to selectively adjust these mechanical properties of the diffuser (such as, for example, through the use of actuators in communication with the controller). In still further optional aspects, it is contemplated that modification of these mechanical properties of the diffuser can be used in combination with (e.g., in sequence with or concurrent with) modification of voltage and/or power properties as further disclosed herein.

According to some optional aspects, the power output of the dispenser can be controllable with a user input device. The user input device can be configured to modify the heat profile. The user input device can be, for example, the momentary switch 104 (FIG. 5) that is actuatable via the button 102. The user input device can be in communication with the controller 100. Upon receiving a user input from the user input device, the input device can cause the controller to modify the heat profile (e.g., optionally, by varying the duty cycle of the voltage delivered to the heater).

Referring also to FIGS. 7A and 8, according to some optional aspects, and as further described herein, the power output of the dispenser 10 can be controllable with a remote device (e.g., a smartphone or other computing device 1001). The user remote device can be in communication with the controller 100 via the transceiver 130. The user remote device can receive an input from a user and, in response, send a signal to the controller 100. In response to receiving the signal from the remote device, the controller 100 can change the power output (e.g., optionally, by varying the duty cycle of the voltage delivered to the heater).

In some aspects, and as further disclosed herein, the heat profile can be selected based on schedules (e.g., select times of day or days of the week) or conditions (e.g., motion detection). For example, the heat profile can include a higher output when the user (or other person in proximity to the diffuser) is present and a lower (or zero) output when the user (or other person in proximity to the diffuser) is not present (e.g., at work). Further, the heat profile can be loaded based on the fragrance characteristics to optimize an individual's experience of the fragrance.

In various aspects, it is contemplated that the disclosed heat profile can be selectively (optionally, manually) adjusted by a user. For example, if the user determines that he or she prefers a particular sequence of power outputs with particular durations or timings, then the heat profile can be modified to reflect those preferences. Optionally, the adjustments can be entered through a user interface and/or a remote device as further disclosed herein.

In exemplary aspects, it is contemplated that the disclosed heat profile and associated components can be incorporated into or combined with any of the diffuser embodiments disclosed herein.

It is contemplated that the dispenser can comprise a plurality of selectable fragrance profiles. Each fragrance profile can be associated with a corresponding heat profile. In some aspects, the dispenser can switch between two different fragrance profiles of the plurality of selectable fragrance profiles. Changing between fragrance profiles can be used to overcome olfactory fatigue.

In further aspects, wattage profiles of the heater can be created by changing an analog wattage value of the heater by using pulses of various amplitude and duration to produce desired effects. Optionally, for analog wattage variation, the pulses can be varied over the course of a duration between one minute and one day (typically on the order of minutes or hours).

Consistent Output

Referring to FIGS. 1 and 6, in some circumstances, with all other factors kept equal (e.g., diffuser heater power output), the fragrance output rate of the diffuser can decline as the fragrance/liquid 62 within the reservoir/bottle 60 becomes depleted. Accordingly, it is contemplated that the heater output for a given output setting (e.g., low, medium, or high) can be increased over the duration of the use of a given reservoir/bottle 60 to compensate for the otherwise declining fragrance output rate. For example, the controller 100 of the diffuser 10 can comprise instructions that increase the power output of the dispenser over the course of the lifetime of the reservoir/bottle 60. That is, the controller 100 can accommodate for the otherwise decreasing diffusion rate by increasing the power output based on the quantity of fragrance remaining in the bottle 60. For example, for a pulse-width-modulated heater with a medium output setting that, at the beginning of the life of the fragrance bottle 60, has a duty cycle of 50%, the medium output setting can increase (e.g., linearly, quadratically, etc. to about 55%, to about 60%, or to about 65%) near the end of the life of the fragrance bottle.

To maintain a consistent output, the quantity of fragrance in the bottle can be determined or approximated, and the output at the different quantities for a given heater power output can be known. The controller can then use a matrix of diffusion rates at select power outputs for select quantities of remaining liquid to calibrate the power output for a desired diffusion rate. For example, a diffusion rate (e.g., mass/time or volume/time) can be empirically or theoretically determined for particular heater power outputs at various stages (e.g., 75% full, 50% full, and 25% full) along the lifetime of a given fragrance bottle 60. Optionally, diffusion rates between empirically determined rates can be determined via interpolation. As disclosed herein, it is further contemplated that the diffusion rate can vary based on the specific fragrance as well. Thus, optionally, the controller can further account for the relative diffusion rate for the specific fragrance.

Accordingly, the controller 100 can determine (e.g., via approximation) the amount of fragrance remaining in the bottle. For example, the controller can do so by estimating an amount of liquid used based on a diffusion rate and a duration of use at said diffusion rate and subtracting the liquid used from the quantity of liquid in a full bottle. Thus, in some aspects, the controller can initially determine that a bottle 60 is full. For example, optionally, after replacing the diffuser 10 with a full bottle 60, a user can provide a user input (e.g., activation of a momentary switch) to cause the controller to reset to the beginning of the life of the bottle. In further optional aspects, a user can communicate with the controller 100 (e.g., with a smartphone, as disclosed herein) to specify the particular bottle size, fragrance, percentage of liquid remaining, etc. The controller can further approximate to the quantity of fragrance used based on the power level, duration of use, etc. The controller can then, based on the quantity of fragrance remaining in the bottle and the desired output setting, calibrate the heater power output to provide a consistent power output over the course of the life of the bottle.

Exemplary Embodiments for Providing Consistent Output

Figure 31:
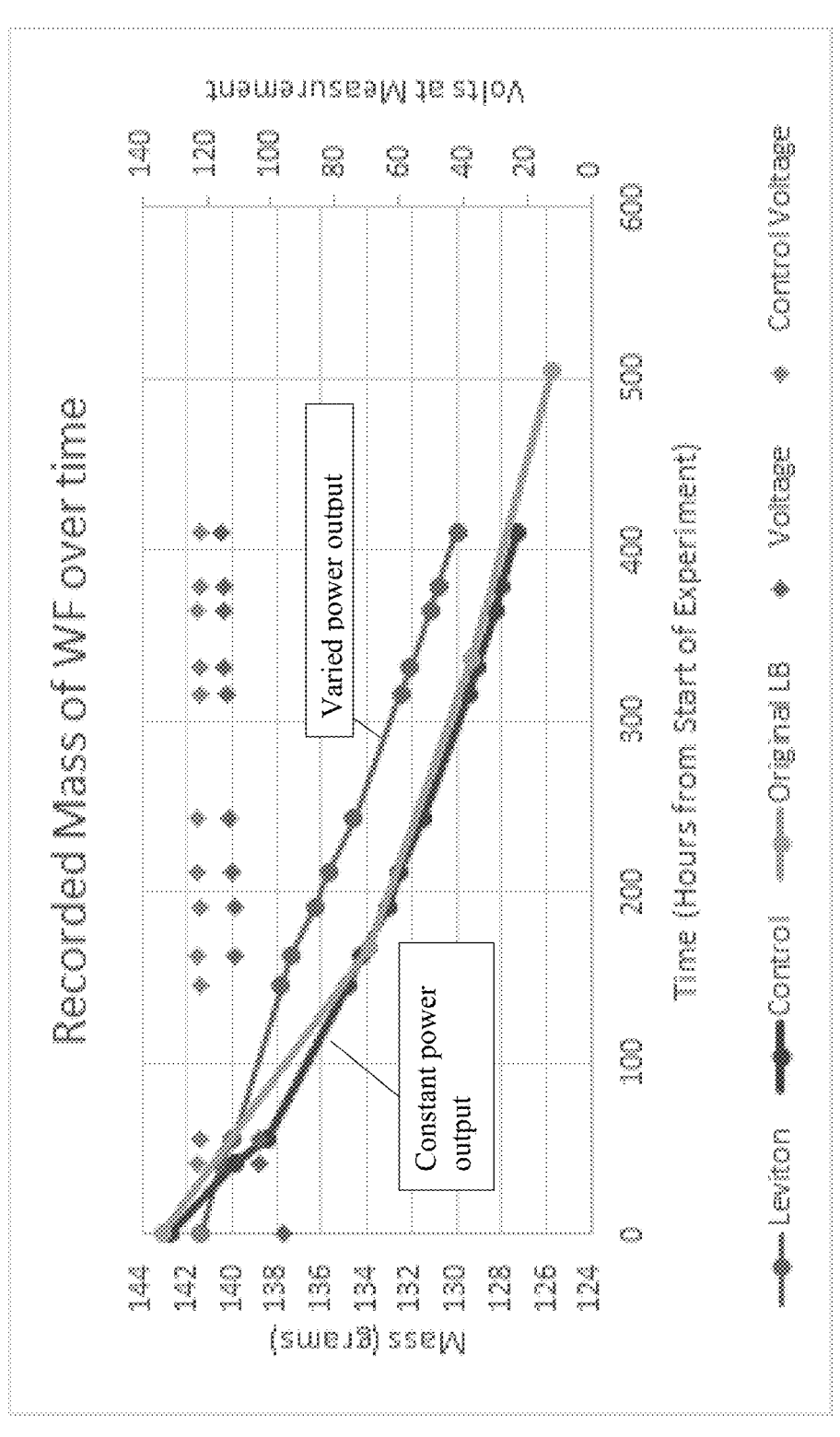
FIG. 31 illustrates a plot of mass of the fragrance over time, showing a comparison between a constant power output and a variable power output over the lifetime of the fragrance bottle.
Figure 32:
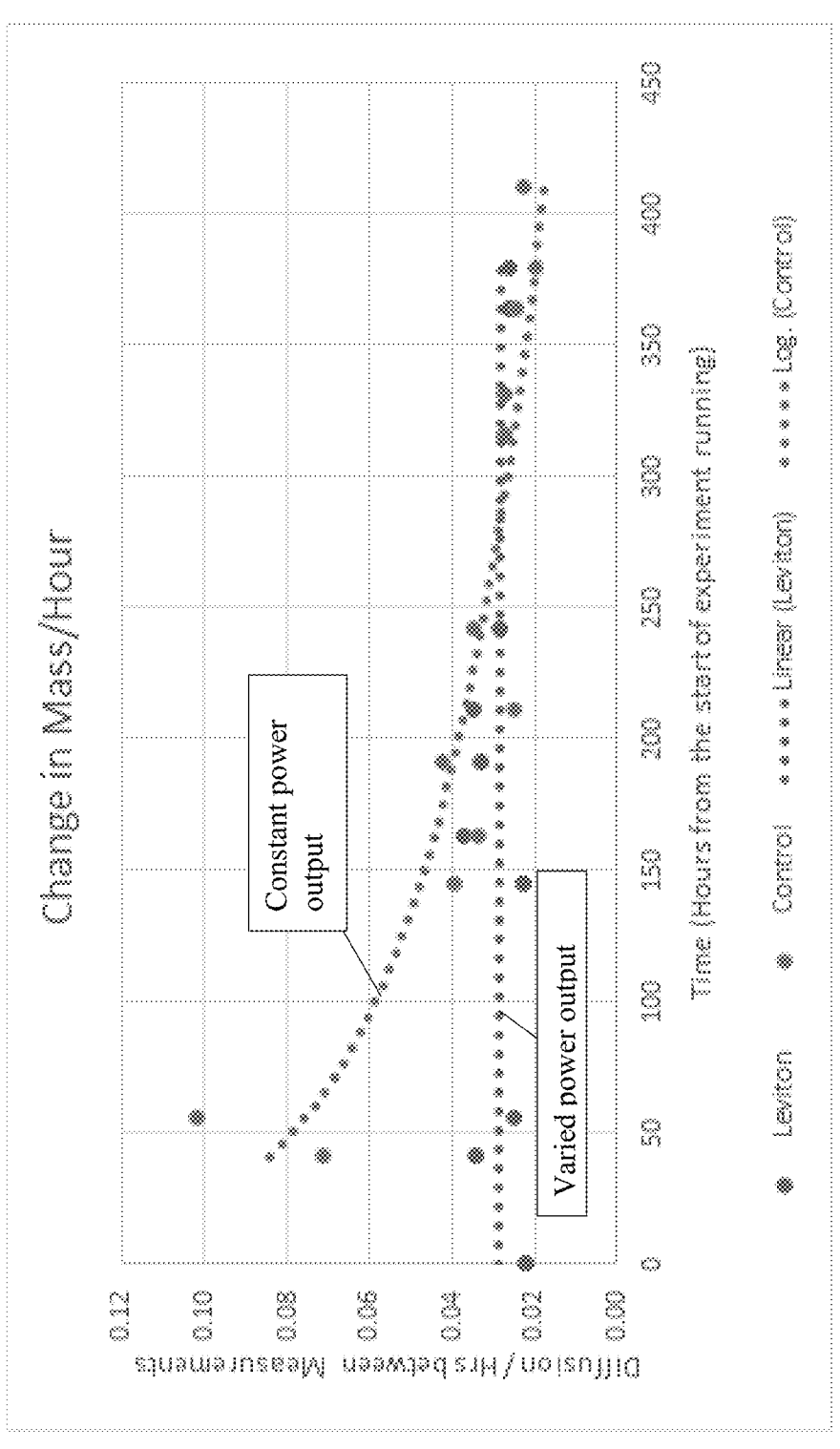
FIG. 32 illustrates a plot of mass dispensing rate of the fragrance over time, showing a comparison between a constant power output and a variable power output over the lifetime of the fragrance bottle.
Figure 33:
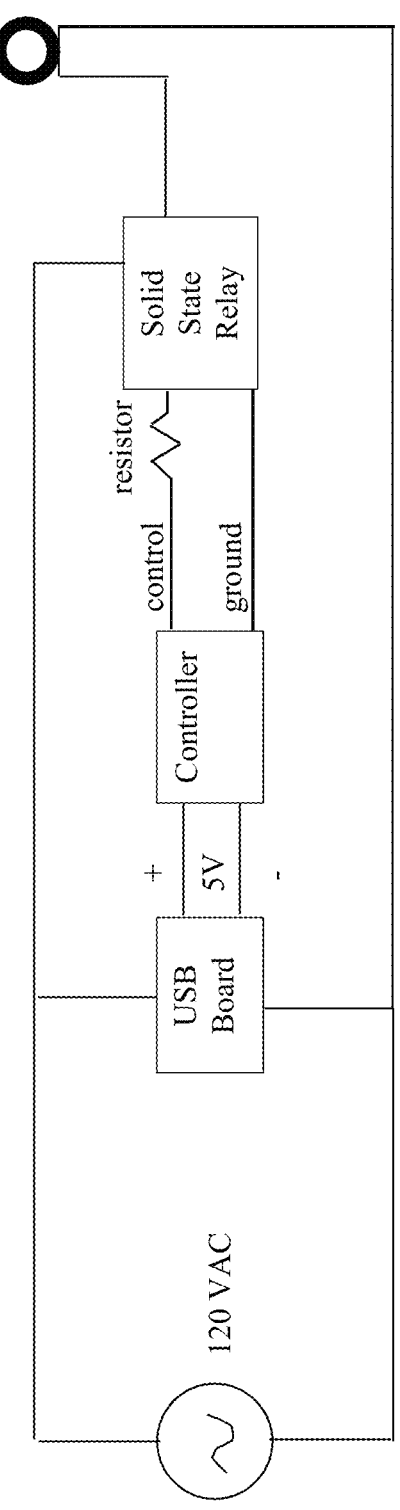
FIG. 33 illustrates an exemplary circuit for varying the power output of the diffuser over the life of the fragrance bottle.

FIG. 33 illustrates a circuit diagram for enabling a controller (e.g., optionally, an additional computing device that serves as the controller) to vary the power output of the diffuser over the lifetime of the fragrance bottle. FIG. 31 is a plot illustrating a comparison between the mass of the dispenser over time for a diffuser providing a constant power output and a diffuser providing an increasing power output over the lifetime of the fragrance bottle. The changing slope of the constant power output sample indicates a change in dispensing rate, whereas the constant slope of the varying power output sample indicates a constant dispensing rate. FIG. 32 is a plot of mass dispensing rate over time, showing a comparison between the diffuser providing the constant power output and the diffuser providing the increasing power output over the lifetime of the fragrance bottle. As shown by the linear line of best fit, the diffuser providing the increasing power output over the lifetime of the fragrance bottle maintains a consistent mass dispensing rate, while the dispensing rate drops off on the constant power output.

Control Based on Chemical Makeup of Fragrance

In some aspects, the controller is configured to vary the heater power to accommodate for a chemical makeup of the fragrance-producing liquid. For example, the heater power can be selected for a specific fragrance in order to optimize the diffusion of the specific fragrance based on the chemical makeup of the specific fragrance (e.g., based on the concentration of one or more chemical components). For example, in some aspects, a first power profile can be preferable for a first fragrance, and a second power profile that is higher or lower than the first power profile can be preferable for a second fragrance. In these aspects, it is contemplated that the controller can be configured to receive or determine an identification of the specific fragrance as further disclosed herein. After receiving or determining the identification of the specific fragrance, the controller can be configured to access a look-up table that associates an optimal power profile for the specific fragrance, and the controller can then cause the diffuser to generate power in accordance with the optimal power profile. This process can be repeated for each fragrance.

Exemplary Aspects

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1A: A fragrance dispenser comprising: a housing having a socket portion and defining a receptacle configured to receive a bottle having a fragrance-producing liquid therein and a wick extending therefrom; a heater disposed proximate to the receptacle so that, when the bottle is received within the receptacle, the heater is disposed proximate to the wick; a controller in electrical communication with the heater, wherein the controller is configured to deliver pulse-width-modulated electrical voltage to the heater, wherein the pulse-width-modulated electrical voltage has a duty cycle; a user input device in communication with the controller, wherein the user input device, upon receiving an input from a user, causes the controller to change the duty cycle of the pulse-width-modulated electrical voltage; and a plurality of lights in communication with the controller, wherein the controller is configured to illuminate one or more lights of the plurality of lights based on the duty cycle of the pulse-width-modulated electrical voltage.

Aspect 2A: The fragrance dispenser of aspect 1A, wherein the user input device is a momentary switch that is actuatable via a button.

Aspect 3A: The fragrance dispenser of aspect 1A or aspect 2A, wherein the controller is configured to output the pulse-width-modulated electrical voltage with a first duty cycle and a second duty cycle that is greater than the first duty cycle, wherein the controller is configured to illuminate a first number of lights of the plurality of lights as the controller outputs the pulse-width-modulated electrical voltage with the first duty cycle, wherein the controller is configured to illuminate a second number of lights of the plurality of lights as the controller outputs the pulse-width-modulated electrical voltage with the second duty cycle, and wherein the second number of lights is greater than the first number of lights.

Aspect 4A: The fragrance dispenser of aspect 3A, wherein the controller is configured to output the pulse-width-modulated electrical voltage with a third duty cycle that is greater than the second duty cycle, wherein the controller is configured to illuminate a third number of lights of the plurality of lights as the controller outputs the pulse-width-modulated electrical voltage with the third duty cycle, wherein the third number of lights is greater than the second number of lights.

Aspect 5A: The fragrance dispenser of any of the preceding aspects, wherein the lights are LEDs.

Aspect 6A: The fragrance dispenser of aspect 5A, wherein the housing has a status display portion that defines a plurality of apertures, and each of the plurality of lights is disposed in alignment with a respective aperture so that light from each of the plurality of lights passes through the respective aperture.

Aspect 7A: The fragrance dispenser of aspect 6A, wherein the plurality of apertures are aligned along an axis from a first end to a second end of the status display portion of the housing, and wherein the controller is configured to illuminate the lights in sequence along the axis from the first end to the second end.

Aspect 8A: The fragrance dispenser of aspect 7A, wherein each of the plurality of apertures has an opening area, wherein the plurality of apertures are arranged in order of increasing opening areas from the first end to the second end of the status display portion of the housing.

Aspect 9A: The fragrance dispenser of any of aspects 6A-8A, further comprising a printed circuit board, wherein the LEDs are disposed on the printed circuit board, wherein the fragrance dispenser further comprises a plurality of light pipes that extend between the LEDs and respective apertures.

Aspect 10A: The fragrance dispenser of any of the preceding aspects, further comprising the bottle having the fragrance-producing liquid therein and the wick extending therefrom.

Aspect 11A: The fragrance dispenser of any of the preceding aspects, further comprising a transceiver in communication with the controller and configured to communicate with a remote computing device.

Aspect 12A: The fragrance dispenser of aspect 11A, wherein the fragrance dispenser is configured to receive a signal from the remote computing device and, in response to receiving the signal, change the duty cycle of the pulse-width-modulated electrical voltage.

Aspect 13A: The fragrance dispenser of aspect 12A, further comprising the bottle having the fragrance-producing liquid therein and the wick extending therefrom, wherein the controller is configured to determine a quantity of the fragrance-producing liquid in the bottle.

Aspect 14A: The fragrance dispenser of aspect 13A, further comprising a level sensor, wherein the controller is configured to determine the quantity of fragrance-producing liquid in the bottle based on a signal from the level sensor.

Aspect 15A: The fragrance dispenser of aspect 13A, wherein the controller is configured to determine the quantity of fragrance in the bottle based on a duration of use of the bottle.

Aspect 16A: The fragrance dispenser of aspect 14A or aspect 15A, wherein the controller is configured to account for a type of fragrance-producing liquid in the bottle in order to determine the quantity of fragrance-producing liquid in the bottle.

Aspect 17A: The fragrance dispenser of aspect 16A, wherein the controller is configured to receive an input indicative of the type of fragrance-producing liquid.

Aspect 18A: The fragrance dispenser of any of the preceding aspects, further comprising a foul odor sensor that is configured to provide a signal to the controller upon sensing a foul odor, wherein the controller is configured to increase the duty cycle of the pulse-width-modulated electrical voltage upon receiving the signal from the foul odor sensor.

Aspect 19A: The fragrance dispenser of any of the preceding aspects, wherein at least one light of the plurality of lights in communication with the controller connected in series with the heater so that a change in the duty cycle changes an intensity of the at least one light.

Aspect 20A: The fragrance dispenser of any of the preceding aspects, wherein the plurality of lights in communication with the controller comprises a plurality of status lights and at least one nightlight, wherein the plurality of status lights comprises a plurality of LEDs, wherein the housing has a status display portion that defines a plurality of apertures, and each of the plurality of status lights is disposed in alignment with a respective aperture so that light from each of the plurality of status lights passes through the respective aperture, wherein the plurality of apertures are aligned along an axis from a first end to a second end of the status display portion of the housing, and wherein the controller is configured to illuminate the lights in sequence along the axis from the first end to the second end, and wherein the at least one nightlight is connected in series with the heater so that a change in the duty cycle changes an intensity of the at least one nightlight.

Aspect 21A: A system comprising: a fragrance dispenser as in any one of aspects 1A-20A; a camera; and processor in communication with the camera and the controller, wherein the processor is configured to receive from the camera an image of an identifier that is associated with the bottle, and wherein the identifier is indicative of the type of fragrance-producing liquid in the bottle.

Aspect 22A: A system comprising: a first fragrance dispenser having a output rate of a first fragrance; a second fragrance dispenser having a output rate of a second fragrance; and a controller in communication with the first fragrance dispenser and the second fragrance dispenser, wherein the controller is configured to control the output rate of the first fragrance dispenser based on the output rate of the second fragrance dispenser.

Aspect 23A: The system of aspect 22A, wherein the controller is configured to modify the output rate of the first fragrance dispenser based at least in part on a distance between the first fragrance dispenser and the second fragrance dispenser.

Aspect 24A: The system of aspect 22A or aspect 23A, wherein the controller is configured to control the output rate of the second fragrance dispenser based on a change in output of the first fragrance dispenser.

Aspect 25A: The system of aspect 24A, wherein the first fragrance dispenser has a fragrance supply, wherein the controller is configured to determine a depletion of the fragrance supply of the first fragrance dispenser, wherein the change in output of the first fragrance dispenser is caused by the depletion of the fragrance supply of the first fragrance dispenser.

Aspect 26A: The system of aspect 25A, wherein the controller is configured to increase the output rate of the first fragrance dispenser based on the depletion of the first fragrance supply of the first fragrance dispenser.

Aspect 27A: The system of any of aspects 22A-26A, wherein the first fragrance dispenser contains a first liquid configured to produce a first fragrance, wherein the second fragrance dispenser contains a second liquid configured to produce a second fragrance that is different from the first fragrance, wherein the controller is configured to determine the first liquid and the second liquid, wherein the controller is configured to control the output rate of the first fragrance dispenser and the output rate of the second fragrance dispenser to create a combined fragrance output having a set proportion of the first fragrance and the second fragrance.

Aspect 28A: The system of aspect 27A, wherein the set proportion is input by a user.

Aspect 29A: The system of aspect 27A, wherein the set proportion is received via instructions that are downloaded from a server.

Aspect 30A: The system of aspect 27A, wherein the controller is configured to determine the first fragrance based on an input from a user.

Aspect 31A: The system of aspect 27A, wherein the controller is configured to determine the first liquid based on image recognition of an identifier of a fragrance bottle.

Aspect 32A: The system of aspect 31A, wherein the identifier of the fragrance bottle is one of a barcode, a QR code, a string of characters, a shape of the bottle, and a unique pattern.

Aspect 33A: The system of any of aspects 22A-32A, wherein the controller is coupled to the first fragrance dispenser, wherein the first fragrance dispenser and second fragrance dispenser are configured in a primary-secondary configuration.

Aspect 34A: The system of any of aspects 22A-33A, wherein the controller is a remote hub that is independent of the first fragrance dispenser and the second fragrance dispenser.

Aspect 35A: The system of aspect 34A, wherein the remote hub is a smartphone.

Aspect 36A: The system of any of aspects 22A-35A, wherein at least one of the first and second fragrance dispensers is a fragrance dispenser as recited in any one of aspects 1-20.

Aspect 37A: A system comprising: at least one diffuser; and a remote computing device in communication with the at least one diffuser, wherein the remote device is configured to: provide a user interface to a user, receive input from the user via the user interface, and in response to receiving the input from the user, perform an operation selected from the group of: adjusting a fragrance diffusion rate of the at least one diffuser, turning on the at least one diffuser, turning off the at least one diffuser.

Aspect 38A: The system of aspect 37A, wherein the at least one diffuser is further operative to: detect a presence of a person, and turn on the diffuser in response to detecting the presence of the person, and detect an absence of a person, and turn off the diffuser in response to detecting the absence of the person.

Aspect 39A: The system of aspect 37A or aspect 38A, wherein the at least one diffuser is further operative to detect an unpleasant odor, and turn on the diffuser in response to detecting the unpleasant odor.

Aspect 40A: The system of any of aspects 37A-39A, further comprising a remote server, wherein the at least one diffuser is in communication with the remote server, and wherein the at least one diffuser is configured to provide to the remote server at least one of the following: a number of the at least one diffusers in a given household; a type of the at least one diffuser; and a type of fragrance associated with the at least one diffuser.

Aspect 41A: The system of aspect 40A, wherein the system is further operative to detect a low quantity of fragrance-producing liquid in a bottle associated with the at least one diffuser, and in response to detecting the low quantity of fragrance-producing liquid in the bottle associated with the at least one diffuser, providing on the user interface a shopping portal to reorder a replacement bottle.

Aspect 42A: The system of aspect 41A, wherein providing on the user interface the shopping portal to reorder the replacement bottle comprises at least one of: providing a recommendation for a replacement bottle having therein a fragrance-producing liquid that is identical to the fragrance-producing liquid in the bottle associated with the at least one diffuser; providing a recommendation for a replacement bottle based on a previous purchase; and providing a recommendation of a replacement bottle based on a time of year.

Aspect 43A: The system of any of aspects 40A-43A, wherein the remote server is configured to determine metrics for a given user or group of users, wherein the metrics comprise data associated with at least one of: the type of the at least one diffuser; and the type of fragrance associated with the at least one diffuser.

Aspect 44A: The system of aspect 43A, wherein the group of users is a group of users in a given region.

Aspect 45A: The fragrance diffuser as in any one of aspects 1A-20A, further comprising an illuminating panel comprising: a transparent plate having a front surface, a back surface, and at least one edge; at least one light source that is configured to illuminate the at least one edge of the transparent plate; a reflective back surface positioned at the back surface of the transparent plate; and a diffusion film positioned at the front surface of the transparent plate.

Aspect 46A: The fragrance diffuser of aspect 45A, further comprising a second reflective surface positioned behind the reflective back surface.

Aspect 47A: The fragrance diffuser of aspect 45A or aspect 46A, wherein the reflective back surface comprises a pattern of dots having a first concentration proximate to the at least one light source and a second concentration that is positioned further from the at least one light source than the first concentration, wherein the second concentration is less than the first concentration.

Aspect 48A: The fragrance diffuser of any one of aspects 45A-47A further comprising a pattern disposed in front of the illuminating panel.

Aspect 49A: The fragrance diffuser of any one of aspects 45A-48A, wherein the illuminating panel is curved and surrounds at least a portion of the housing to provide an illuminated cuff.

Aspect 50A: The fragrance diffuser of aspect 49A, further comprising a pattern on an exterior of the illuminated cuff.

Aspect 51A: The fragrance diffuser of aspect 49A or aspect 50A, wherein the transparent material defines an upper edge and a lower edge, wherein the illuminated cuff further comprises at least one rim cover extending across at least one of an upper edge and a lower edge of the transparent plate.

Aspect 52A: The fragrance diffuser as in any one of aspects 1A-20A or 45A-51A, further comprising a projector, the projector comprising: a light source; a lens that is configured to direct light from the light source to a projection surface; and a film having at least one of an image or a pattern thereon, wherein the lens and the film are positioned with respect to each other so that either: the lens is disposed between the light source and the film; or the film is disposed between the light source and the lens.

Aspect 53A: The fragrance diffuser of aspects 52A, wherein the lens is a collimating lens that is disposed between the light source and the film, the fragrance diffuser further comprising: a focusing lens, wherein the film is disposed between the collimating lens and the focusing lens; and an expansion lens, wherein the focusing lens is disposed between the film and the expansion lens.

Aspect 54A: The fragrance diffuser as in any one of aspects 1A-20A or 45A-48A, further comprising an illuminated cuff, the illuminated cuff comprising: a transparent material extending around at least a portion of a circumference of the housing of the diffuser, wherein the transparent material defines an interior volume; and a light source disposed within the interior volume of the illuminated cuff.

Aspect 55A: A fragrance dispenser comprising: a housing having a socket portion and defining a receptacle configured to receive a bottle having a fragrance-producing liquid therein and a wick extending therefrom; a heater disposed proximate to the receptacle so that, when the bottle is received within the receptacle, the heater is disposed proximate to the wick; and an illuminating panel coupled to the housing, the illuminating panel comprising: a transparent plate having a front surface, a back surface, and at least one edge, at least one light source that is configured to illuminate the at least one edge of the transparent plate, a reflective back surface positioned at the back surface of the transparent plate, and a diffusion film positioned at the front surface of the transparent plate.

Aspect 56A: The fragrance dispenser of aspect 55A, wherein the illuminating panel is curved and surrounds at least a portion of the housing.

Aspect 57A: A fragrance dispenser comprising: a housing having a socket portion and defining a receptacle configured to receive a bottle having a fragrance-producing liquid therein and a wick extending therefrom; a heater disposed proximate to the receptacle so that, when the bottle is received within the receptacle, the heater is disposed proximate to the wick; and a projector coupled to the housing, the projector comprising: a light source; a lens that is configured to direct light from the light source to a projection surface; and a film having at least one of an image or a pattern thereon, wherein the lens and the film are positioned with respect to each other so that either: the lens is disposed between the light source and the film; or the film is disposed between the light source and the lens.

Aspect 58A: The fragrance diffuser of aspects 57A, wherein the lens is a collimating lens that is disposed between the light source and the film, the fragrance diffuser further comprising: a focusing lens, wherein the film is disposed between the collimating lens and the focusing lens; and an expansion lens, wherein the focusing lens is disposed between the film and the expansion lens.

Aspect 59A: A fragrance dispenser comprising: a housing having a socket portion and defining a receptacle configured to receive a bottle having a fragrance-producing liquid therein and a wick extending therefrom; a heater disposed proximate to the receptacle so that, when the bottle is received within the receptacle, the heater is disposed proximate to the wick; and an illuminated cuff coupled to the housing, the illuminated cuff comprising: a transparent material extending around at least a portion of a circumference of the housing of the diffuser, wherein the transparent material defines an interior volume, and a light source disposed within the interior volume of the illuminated cuff.

Aspect 60A: The fragrance diffuser of aspect 3A, wherein the second number of lights is greater than the first number of lights.

Aspect 61A: The fragrance diffuser of aspect 3A, wherein the second number of lights is less than the first number of lights.

Aspect 62A: The fragrance diffuser of aspect 3A, wherein the second number of lights is equal to the first number of lights.

Aspect 63A: The fragrance diffuser of aspect 4A, wherein the third number of lights is greater than the second number of lights.

Aspect 64A: The fragrance diffuser of aspect 4A, wherein the third number of lights is less than the second number of lights.

Aspect 65A: The fragrance diffuser of aspect 4A, wherein the third number of lights is equal to the second number of lights.

Aspect 66A: The fragrance diffuser of any one of aspects 45A-51A, wherein the at least one light source is configured to vary in intensity based on the duty cycle of the pulse-width-modulated electrical voltage.

Aspect 67A: The fragrance diffuser of aspect 52A or aspect 53A, wherein the light source is configured to vary in intensity based on the duty cycle of the pulse-width-modulated electrical voltage.

Aspect 68A: The fragrance diffuser of aspect 46A, wherein the second reflective surface is defined by a reflective film, wherein the reflective surface is disposed between the second reflective film and the transparent plate.

Aspect 1B: A fragrance dispenser comprising: a housing having a socket portion and defining a receptacle configured to receive a bottle having a fragrance-producing liquid therein and a wick extending therefrom; a heater disposed proximate to the receptacle so that, when the bottle is received within the receptacle, the heater is disposed proximate to the wick, wherein the heater has a variable power output; and a controller in electrical communication with the heater, wherein the controller is configured to control the power output of the heater in accordance with a heat profile, the heat profile comprising a first power output, a second power output that is greater than the first power output, and a third power output that is greater than the first and second power outputs, wherein each of the first, second, and third power outputs has a duration ranging from 73 minutes to one week.

Aspect 2B: The fragrance dispenser of aspect 1B, wherein each of the first, second, and third power outputs has a duration ranging from 75 minutes to 12 hours.

Aspect 3B: The fragrance dispenser of aspect 2B, wherein each of the first, second, and third power outputs has a duration ranging from 90 minutes to four hours.

Aspect 4B: The fragrance dispenser of any one of aspects 1B-3B, wherein each of the first, second, and third power outputs has an equal duration.

Aspect 5B: The fragrance dispenser of aspect 4B, wherein the equal duration is 90 minutes.

Aspect 6B: The fragrance dispenser of any one of aspects 1B-5B, wherein the heat profile includes a pattern sequence.

Aspect 7B: The fragrance dispenser of aspect 6B, wherein the pattern sequence is: the second power output; the third power output; the second power output; and the first power output.

Aspect 8B: The fragrance dispenser of aspect 7B, wherein the heat profile comprises at least one repeat of the pattern sequence.

Aspect 9B: The fragrance dispenser of aspect 6B, wherein the pattern sequence is: the third power output; the second power output; the first power output; and the second power output.

Aspect 10B: The fragrance dispenser of aspect 9B, wherein the heat profile comprises at least one repeat of the pattern sequence.

Aspect 11B: The fragrance dispenser of any one of aspects 1B-10B, wherein the first power output ranges from 1.5 W to 2.0 W, wherein the second power output ranges from 2.0 W to 2.4 W, and wherein the third power output ranges from 2.4 W to 3.0 W.

Aspect 12B: The fragrance dispenser of any one of aspects 1B-11B, wherein the heat profile has an inactive cycle during which the controller provides a minimum value of voltage to the heater.

Aspect 13B: The fragrance dispenser of aspect 12B, wherein the minimum value of voltage is zero.

Aspect 14B: The fragrance dispenser of any one of aspects 1B-13B, further comprising a user input device in communication with the controller, wherein the user input device, upon receiving an input from a user, causes the controller to modify the heat profile.

Aspect 15B: The fragrance dispenser of aspect 14B, wherein the user input device, upon receiving the input from the user, causes the controller to change the power output of the heater.

Aspect 16B: The fragrance dispenser of aspect 14B or aspect 15B, wherein the user input device is a momentary switch that is actuatable via a button.

Aspect 17B: The fragrance dispenser of any one of aspects 1B-16B, further comprising a transceiver in communication with the controller and configured to communicate with a remote computing device.

Aspect 18B: The fragrance dispenser of aspect 17B, wherein the fragrance dispenser is configured to receive a signal from the remote computing device and, in response to receiving the signal, modify the heat profile.

Aspect 19B: The fragrance dispenser of aspect 18B, wherein in response to receiving the signal, the fragrance dispenser is configured to change the power output of the heater.

Aspect 20B: The fragrance dispenser of any one of aspects 1B-19B, further comprising the bottle having the fragrance-producing liquid therein and the wick extending therefrom.

Aspect 21B: The fragrance dispenser of aspect 20B, wherein the bottle consists of a single bottle.

Aspect 22B: The fragrance dispenser of any one of aspects 1B-21B, wherein the controller is configured to vary the power output of the heater by delivering a pulse-width-modulated electrical voltage to the heater, wherein the first power output is caused by delivering to the heater the pulse-width-modulated electrical voltage having a first duty cycle, wherein the second power output is caused by delivering to the heater the pulse-width-modulated electrical voltage having a second duty cycle that is greater than the first duty cycle, and wherein the third power output is caused by delivering to the heater the pulse-width-modulated electrical voltage having a third duty cycle that is greater than the first and second duty cycles.

Aspect 23B: The fragrance dispenser of as aspect 22B, wherein the first duty cycle ranges from about 5% to about 40%, the second duty cycle ranges from about 35% to about 75%, and the third duty cycle ranges from about 70% to about 100%.

Aspect 24B: A fragrance dispenser comprising: a housing having a socket portion and defining a receptacle configured to receive a bottle having a fragrance-producing liquid therein and a wick extending therefrom; a heater disposed proximate to the receptacle so that, when the bottle is received within the receptacle, the heater is disposed proximate to the wick, wherein the heater has a variable power output; and a controller in electrical communication with the heater, wherein the controller is configured to control the power output of the heater.

Aspect 25B: The fragrance dispenser of aspect 24B, wherein the controller is configured to increase the heater power over time in order to maintain a constant dispensing rate.

Aspect 26B: The fragrance dispenser of aspect 24B or aspect 25B, wherein the controller is configured to vary the heater power to accommodate for (or based on) a chemical makeup of the fragrance-producing liquid.

Aspect 27B: The fragrance dispenser of any one of aspects 24B-26B, wherein the chemical makeup of the fragrance-producing liquid changes over an amount of use and the controller is configured to vary the heater power to accommodate for (or based on) a change in the chemical makeup of the fragrance-producing liquid.

Aspect 28B: The fragrance dispenser of any one of aspects 24B-27B, wherein the controller is configured to control the power output of the heater via analog wattage modulation.

Aspect 29B: The fragrance dispenser of any one of aspects 24B-28B, wherein the controller is configured to control the power output of the heater via pulse-width wattage modulation.

Aspect 30B: The fragrance controller of any one of aspects 24B-29B, further comprising a receiver in communication with the controller, wherein the receiver is configured to receive a signal from a remote device and the controller is configured to change the power output of the heater based on the signal from the remote device.

Aspect 31B: The fragrance dispenser of any one of aspects 24B-30B, wherein the controller is configured to control the power output of the heater based on a time of day.

Aspect 32B: The fragrance dispenser of any one of aspects 24B-31B, wherein the controller is configured to track a quantity of use of the fragrance-dispensing liquid.

Aspect 33B: The fragrance dispenser of aspect 32B, wherein the controller is configured to: determine when the fragrance-dispensing liquid is below a threshold; and output a signal indicating that the fragrance-dispensing liquid is below the threshold.

Aspect 34B: A method of dispensing fragrance using the fragrance dispenser of any one of the preceding aspects.

Aspect 1C: A fragrance dispenser comprising: a housing having a socket portion and defining a receptacle configured to receive a bottle having a fragrance-producing liquid therein and a wick extending therefrom; a heater disposed proximate to the receptacle so that, when the bottle is received within the receptacle, the heater is disposed proximate to the wick; and a controller in electrical communication with the heater.

Aspect 2C: The fragrance dispenser of aspect 1C, wherein the controller is configured to determine a quantity of the fragrance-producing liquid in the bottle based on a duration of use of the bottle.

Aspect 3C: The fragrance dispenser of aspect 1C or aspect 2C, further comprising the bottle having the fragrance-producing liquid therein and the wick extending therefrom.

Aspect 4C: The fragrance dispenser of aspect 2C or aspect 3C, wherein the controller is configured to account for a type of fragrance-producing liquid in the bottle in order to determine the quantity of fragrance-producing liquid in the bottle.

Aspect 5C: The fragrance dispenser of any one of aspects 1C-4C, wherein the controller is configured to deliver pulse-width-modulated electrical voltage to the heater, wherein the pulse-width-modulated electrical voltage has a duty cycle, the fragrance dispenser further comprising: a user input device in communication with the controller, wherein the user input device, upon receiving an input from a user, causes the controller to change the duty cycle of the pulse-width-modulated electrical voltage; and a plurality of lights in communication with the controller, wherein the controller is configured to illuminate one or more lights of the plurality of lights at an intensity based on the duty cycle of the pulse-width-modulated electrical voltage.

Aspect 6C: The fragrance dispenser of aspect 5C, wherein at least one light of the plurality of lights in communication with the controller is connected in series with the heater so that a change in the duty cycle changes an intensity of the at least one light.

Aspect 7C: The fragrance dispenser of any one of aspects 1C-6C, further comprising a projector, the projector comprising: a light source; a lens that is configured to direct light from the light source to a projection surface; and a film having at least one of an image or a pattern thereon, wherein the lens and the film are positioned with respect to each other so that either: the lens is disposed between the light source and the film; or the film is disposed between the light source and the lens.

Aspect 8C: The fragrance dispenser of any one of aspects 1C-7C, wherein the controller is configured to determine a size of a room in which the dispenser is located, and, control the power output of the heater based at least in part on the size of the room.

Aspect 9C: A system comprising: a first fragrance dispenser; a second fragrance dispenser, wherein each of the first fragrance dispenser and the second fragrance dispenser comprises: a housing having a socket portion and defining a receptacle configured to receive a bottle having a fragrance-producing liquid therein and a wick extending therefrom; a heater disposed proximate to the receptacle so that, when the bottle is received within the receptacle, the heater is disposed proximate to the wick; and a controller in electrical communication with the heater; and a coordinating controller in communication with the first fragrance dispenser and the second fragrance dispenser, wherein the coordinating controller is configured to control a fragrance output rate of the first fragrance dispenser based on a fragrance output rate of the second fragrance dispenser.

Aspect 10C: The system of aspect 9C, wherein the coordinating controller is the controller of the first fragrance dispenser.

Aspect 11C: The system of aspect 9C, wherein the coordinating controller is a hub that is in communication with each of the controller of the first fragrance dispenser and the controller of the second fragrance dispenser.

Aspect 12C: The system of any one of aspects 9C-11C, wherein the coordinating controller is configured to control the fragrance output rate of the first fragrance dispenser based on a change in fragrance output of the first fragrance dispenser.

Aspect 13C: The system of aspect 12C, wherein the first fragrance dispenser has a fragrance supply, wherein the controller is configured to determine a depletion of the fragrance supply of the first fragrance dispenser, wherein the change in fragrance output of the first fragrance dispenser is caused by the depletion of the fragrance supply of the first fragrance dispenser.

Aspect 14C: The system of any one of aspects 9C-13C, wherein the first fragrance dispenser contains a first liquid configured to produce a first fragrance, wherein the second fragrance dispenser contains a second liquid configured to produce a second fragrance that is different from the first fragrance, wherein the controller is configured to determine the first liquid and the second liquid, wherein the controller is configured to control the output rate of the first fragrance dispenser and the output rate of the second fragrance dispenser to create a combined fragrance output having a set proportion of the first fragrance and the second fragrance.

Aspect 15C: The system of any one of aspects 9C-14C, wherein the coordinating controller is configured to determine a spacing between the first fragrance dispenser and the second fragrance dispenser, wherein the coordinating controller is further configured to control the heater of at least one of the first fragrance dispenser and the second fragrance dispenser based on the spacing between the first fragrance dispenser and the second fragrance dispenser.

Aspect 16C: The system of any one of aspects 9C-15C, wherein the coordinating controller is configured to change the fragrance output of at least one of the first diffuser and the second diffuser based on a proximity of a person.

Aspect 17C: A system comprising: at least one fragrance diffuser, each fragrance diffuser comprising: a housing having a socket portion and defining a receptacle configured to receive a bottle having a fragrance-producing liquid therein and a wick extending therefrom; a heater disposed proximate to the receptacle so that, when the bottle is received within the receptacle, the heater is disposed proximate to the wick; and a controller in electrical communication with the heater; and a remote computing device in communication with controller of each fragrance diffuser of the at least one fragrance diffuser, wherein the remote computing device is configured to: provide a user interface to a user, receive input from the user via the user interface, and in response to receiving the input from the user, perform an operation selected from the group of: adjusting a fragrance diffusion rate of the at least one diffuser, turning on the at least one diffuser, turning off the at least one diffuser.

Aspect 18C: The system of aspect 17C, wherein the at least one fragrance diffuser is further operative to: detect a presence of a person, and turn on the diffuser in response to detecting the presence of the person; and detect an absence of a person, and turn off the diffuser in response to detecting the absence of the person.

Aspect 19C: The system of aspect 17C or aspect 18C, wherein the remote computing device is in communication with at least one other Internet of things device, wherein, in response to the at least one other Internet of things device changing a status, the remote computing device is configured to cause the at least one fragrance diffuser to change the fragrance diffusion rate, turn on, or turn off.

Aspect 20C: The system of aspect 19C, wherein the at least one Internet of things device comprises a smart thermostat, a smart lighting device, or combinations thereof.

Aspect 21C: The system of aspect 19C or aspect 20C, wherein the remote computing device is configured to determine an occupancy mode that is one of an at home mode and an away mode, wherein the computing device is configured to, in response to determining a change in the occupancy mode, perform an operation comprising: adjusting a fragrance diffusion rate of the at least one fragrance diffuser, turning on the at least one fragrance diffuser, or turning off the at least one fragrance diffuser.

Aspect 22C: The system of any one of aspects 19C-21C, wherein the remote computing device is configured to, based on a scheduled routine, perform an operation selected from the group of: adjusting a fragrance diffusion rate of the at least one diffuser, turning on the at least one diffuser, turning off the at least one diffuser.

Although the foregoing invention has been described in some detail by way of illustration and example for purposes of clarity of understanding, certain changes and modifications may be practiced within the scope of the appended claims.

The invention claimed is:

1. A fragrance dispenser comprising:
a housing having a socket portion and defining a receptacle configured to receive a bottle having a fragrance-producing liquid therein and a wick extending therefrom;
a single heater disposed within the housing so that, when the bottle is received within the receptacle, the single heater is configured to heat a portion of the wick;
a controller in electrical communication with the single heater, wherein the controller is configured to control an output setting of the single heater;
a user input device in communication with the controller, wherein the user input device, upon receiving an input from a user, causes the controller to change the output setting of the single heater; and
at least one light in communication with the controller;
wherein the at least one light comprises a plurality of status lights and wherein the controller is configured to illuminate one or more status lights in the plurality of status lights in accordance with the output setting of the single heater;
wherein the housing has a status display portion that defines a plurality of apertures, wherein the plurality of status lights comprises a plurality of LEDs that are configured to emit light into respective light pipes disposed in the housing, and wherein the light pipes are configured to deliver light from the LEDs through respective apertures of the plurality of apertures; and wherein the output setting of the single heater comprises at least a low output setting of the single heater, a medium output setting of the single heater, and a high output setting of the single heater, wherein the controller is configured to illuminate only one of the status lights in the plurality of status lights in accordance with the low output setting of the single heater, wherein the controller is configured to illuminate only two of the status lights in the plurality of status lights in accordance with the medium output setting of the single heater, and wherein the controller is configured to illuminate at least three of the status lights in the plurality of status lights in accordance with the high output setting of the single heater.

2. The fragrance dispenser of claim 1, further comprising the bottle having the fragrance-producing liquid therein and the wick extending therefrom.

3. The fragrance dispenser of claim 1, wherein the controller is configured to deliver pulse-width-modulated electrical voltage to the single heater to control the output setting of the single heater, wherein the pulse-width-modulated electrical voltage has a duty cycle, and wherein at least a first light of the at least one light is connected in series with the single heater so that a change in the duty cycle changes an intensity of the first light.

4. The fragrance dispenser of claim 1, further comprising a projector, the projector comprising:
   a light source;
   a lens that is configured to direct light from the light source to a projection surface; and
   a film having at least one of an image or a pattern thereon, wherein the lens and the film are positioned with respect to each other so that either:
      the lens is disposed between the light source and the film; or
      the film is disposed between the light source and the lens.

5. The fragrance dispenser of claim 1, wherein the controller is configured to determine a quantity of the fragrance-producing liquid in the bottle based on a duration of use of the bottle.

6. The fragrance dispenser of claim 1, wherein the controller is configured to deliver pulse-width-modulated electrical voltage to the single heater to control the output setting of the single heater, wherein the pulse-width-modulated electrical voltage has a duty cycle, wherein the at least one light comprises a nightlight that emits light through an opening in the housing, wherein the nightlight has an intensity that varies based on the duty cycle of the pulse-width-modulated electrical voltage, and wherein the nightlight is connected in series with a resistor of the single heater.

7. The fragrance dispenser of claim 5, wherein the controller is configured to account for a particular fragrance-producing liquid in the bottle in order to determine the quantity of fragrance-producing liquid in the bottle.

* * * * *